(12) United States Patent
Oas et al.

(10) Patent No.: US 7,413,906 B2
(45) Date of Patent: Aug. 19, 2008

(54) QUANTITATIVE, HIGH-THROUGHPUT SCREENING METHOD FOR PROTEIN STABILITY

(75) Inventors: Terence G. Oas, Durham, NC (US); Sina Ghaemmaghami, Durham, NC (US); Kendall D. Powell, Durham, NC (US); Michael C. Fitzgerald, Durham, NC (US)

(73) Assignee: Duke University, Durham, NC (US)

( * ) Notice: Subject to any disclaimer, the term of this patent is extended or adjusted under 35 U.S.C. 154(b) by 71 days.

(21) Appl. No.: 11/634,019

(22) Filed: Dec. 5, 2006

(65) Prior Publication Data

US 2007/0099305 A1 May 3, 2007

Related U.S. Application Data

(62) Division of application No. 10/807,034, filed on Mar. 18, 2004, now Pat. No. 7,148,071, which is a division of application No. 09/845,363, filed on Apr. 30, 2001, now Pat. No. 6,734,023.

(60) Provisional application No. 60/200,311, filed on Apr. 28, 2000.

(51) Int. Cl.
*G01N 1/00* (2006.01)
(52) U.S. Cl. .............................. 436/63; 436/86; 436/89; 436/173; 436/501; 436/518; 436/811
(58) Field of Classification Search ................... 436/63, 436/86, 89, 173, 501, 518, 811
See application file for complete search history.

(56) References Cited

U.S. PATENT DOCUMENTS

| 5,470,753 A | 11/1995 | Sepetov et al. |
| 5,658,739 A | 8/1997 | Woods et al. |
| 5,679,582 A | 10/1997 | Bowie et al. |

FOREIGN PATENT DOCUMENTS

| WO | WO 99/09204 | 2/1999 |
| WO | WO 00/16100 | 3/2000 |

OTHER PUBLICATIONS

Deng et al. Comparison of Continuous and Pulsed Labeling Amide Hydrogen. *Journal of the American Society for Mass Spectrometry*, vol. 10, No. 5, (1999), pp. 675-684.
Buijs et al. Conformational Stability of Adsorbed Insulin Studied with Mass Spectrometry and Hydrogen Echang. *Analytical Chemistry*, vol. 71, No. 15, (1999), pp. 3219-3225.
Chaurand et al. Direct Profiling of Proteins in Biological Tissue Sections by MALDI Mass Spectrometry. *Analytical Chemistry*, vol. 71, No. 23, (1999), p. 5263-5270.
Deng et al. Comparison of continuous and pulsed labeling amide hydrogen exchange/mass spectrometry for studies of protein dynamics *Journal of the American Society for Mass Spectrometry*, vol. 10, No. 5, (1999), pp. 675-684.

Deng et al. Identification of Unfolding Domains in Large Proteins by Their Unfolding Rates. *Biochemistry*, vol. 37, No. 180, (1998), p. 6256-6262.
Deng et al. Rate and Equilibrium Contants for Protein Unfolding and Refolding Determined by Hydrogen-Mass Spectrometry. *Analytical Biochemistry*, vol. 276, No. 2, (1999), pp. 150-160.
Ehring et al. Analytical Biochemistry, vol. 267, (1999), p. 252.
European Patent Office Communication for corresponding PCT/EP Appl. No. EP 01 92 8981 dated Oct. 13, 2004.
European Patent Office Communication for corresponding PCT/EP Appl. No. EP 01 92 8981 dated Aug. 14, 2006.
Keller et al. Discerning Matraix-Cluster Peaks in Matrix-Assisted Laser Desorption/Ionization Time-of-Flight Mass Spectra of Dilute Peptide Mixtures. *Journal of the American Society of Mass Spectrometry*, vol. 11, No. 1, (2000), p. 88-93.
Mandell et al. Measurement of Amide Hydrogen Exchange by MALDI-TOF Mass Spectrometry. *Analytical Chemistry*, vol. 70, (1998), pp. 3987-3995.
Ragona et al. Unfolding and Refolding of Bovine β-Lactoglobulin Monitored by Hydrogen Exchange Measurements, *J. Mol. Biol.* 293,:953-969 (1999).
Rosenbaum et al. Screening Combinatorial Libraries of de Novo Proteins by Hydrogen-Deuterium Exchange and Electrospray Mass Spectrometry. *Journal of American Chemical Society*, vol. 121, (1999), pp. 9509-9951.
Smith et al. *Biochemistry*, vol. 63, (1998), p. 285.
Villanueva et al. Hydrogen exchange monitored by MALDI-TOF mass spectrometry for rapid characterization of the stability and conformation of proteins. *Federation of European Biochemical Societies*, vol. 472, (2000), pp. 27-33.
Walker et al. Effects of Protein Surface Interactions on Protein Ion Signals in MALDI Mass Spectrometry. *Analytical Biochemistry*, vol. 71, No. 1, (1999), pp. 268-272.
Office Communication corresponding to an EP application Serial No. 01928981.8-1223 dated Apr. 10, 2007.

*Primary Examiner*—Long V. Le
*Assistant Examiner*—Changhwa J Cheu
(74) *Attorney, Agent, or Firm*—Jenkins, Wilson, Taylor & Hunt, P.A.

(57) ABSTRACT

In proteomic research, it is often necessary to screen a large number of polypeptides for the presence of stable structure. Described herein are methods (referred to as MALDI MS-HX and SUPREX) for measuring the stability of proteins in a rapid, high-throughput fashion. The method employs hydrogen exchange to estimate the stability of quantities of unpurified protein extracts, using matrix-assisted laser desorption/ionization (MALDI) mass spectrometry. A method of quantitatively determining the stability of a test protein under native conditions is disclosed. The method includes the steps (a) providing a test protein; (b) contacting the protein with an exchange buffer comprising a denaturant and deuterium, the exchange buffer having a denaturant concentration; (c) contacting the test protein with a mass spectrometry matrix medium; (d) determining a change in mass of the test protein by mass spectrometry; (e) varying the denaturant concentration of the exchange buffer; (f) repeating steps (a)-(e) a desired number of times; and (g) quantitatively determining protein stability based on the change in mass of the test protein as a function of denaturant concentration, whereby the stability of a test protein under native conditions is quantitatively determined.

20 Claims, 20 Drawing Sheets

SEQUENCE LISTING

<160> NUMBER OF SEQ ID NOS: 1

<210> SEQ ID NO 1
<211> LENGTH: 27
<212> TYPE: DNA
<213> ORGANISM: Artificial
<220> FEATURE:
<223> OTHER INFORMATION: Arc repressor cognate DNA
<220> FEATURE:
<221> NAME/KEY: protein_bind
<222> LOCATION: (1)..(27)

<400> SEQUENCE: 1
atcgatgata gaagcactct actatcg                    27

QUANTITATIVE, HIGH-THROUGHPUT SCREENING METHOD FOR PROTEIN STABILITY

CROSS REFERENCE TO RELATED APPLICATIONS

This application is a divisional of U.S. patent application Ser. No. 10/807,034, filed Mar. 18, 2004 now U.S. Pat. No. 7,148,071, herein incorporated by reference in its entirety, which is a divisional of U.S. patent application Ser. No. 09/845,363, filed Apr. 30, 2001 now U.S. Pat. No. 6,734,023, herein incorporated by reference in its entirety, which is based on and claims priority to U.S. Provisional Application Ser. No. 60/200,311, filed Apr. 28, 2000, herein incorporated by reference in its entirety.

GRANT STATEMENT

This work was supported by NIH grant GM45322. Thus, the U.S. Government has certain rights in the invention.

TECHNICAL FIELD

The present invention relates generally to a method of screening for protein stability. More particularly, the present invention relates to a quantitative method of screening for protein stability that can be employed in a high throughput setting using relatively small amounts of pure and impure protein samples.

| Table of Abbreviations | |
|---|---|
| BSA | bovine serum albumin |
| CD | circular dichroism |
| DSC | differential scanning calorimetry |
| ESI | electrospray ionization |
| FE | fraction exchanged |
| FIV | feline immunodeficiency virus |
| GdmCl | guanidinium monochloride |
| IPTG | isopropylthio-β-D-galactosidase |
| H/D | hydrogen/deuterium |
| HX | hydrogen exchange |
| $\lambda_{6-85}$ | monomeric λ repressor |
| MALDI | matrix assisted laser desorption/ionization |
| MBP | maltose binding protein |
| MS | mass spectrometry |
| MS-HX | mass spectrometry-hydrogen exchange |
| m/z | mass-to-charge ratio |
| NMR | nuclear magnetic resonance |
| SIV | simian immunodeficiency virus |
| SUPREX | stability of unpurified proteins from rates of H/D exchange |

| Amino Acid Abbreviations | | |
|---|---|---|
| Single-Letter Code | Three-Letter Code | Name |
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

| Functionally Equivalent Codons | | | |
|---|---|---|---|
| Amino Acid | | | Codons |
| Alanine | Ala | A | GCA GCC GCG GCU |
| Cysteine | Gys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Methionine | Met | M | AUG |
| Asparagine | Asn | N | AAC AAU |
| Proline | Pro | P | CCA CCC CCG CCU |
| Glutamine | Gln | Q | CAA CAG |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |
| Leucine | Leu | L | UUA UUG CUA CUC CUG CUU |
| Arginine | Arg | R | AGA AGG CGA CGC CGG CGU |
| Serine | Ser | S | ACG AGU UCA UCC UCG UCU |

BACKGROUND ART

Natural proteins differ from most polymers in that they predominantly populate a single, ordered three-dimensional structure in solution. It has long been recognized that this ordered structure can be transformed to an approximate random chain by changes in temperature, pressure or solvent conditions (Neurath et al., (1944) *Chem. Rev.* 34: 157-265).

The ability to induce protein unfolding, and subsequent refolding, has allowed scientists to analyze the physical chemistry of the folding reaction in vitro (Schellman, (1987) *Annu. Rev. Biophys. Bio.* 16: 115-37). These investigations have shed light on the kinetics and thermodynamics of conformational changes in proteins and are of biological interest for two important reasons. First, they aid in the understanding of how proteins, which start their existence in the cell in a disordered state, manage to rapidly transform into a single, folded, functional conformation. Second, they elucidate the nature of functionally significant structural fluctuations present in proteins once folding equilibrium is reached.

The function of a protein is contingent on the stability of its native conformation. Consequently, in the field of protein biochemistry, stability measurements are frequently performed to establish a polypeptide as a stably folded protein and to study the physical forces that lead to its folding (Schellman, (1987) *Annu. Rev. Biophys. Bio.* 16: 115-37). Stability measurements also provide important biological information; a decrease in stability can be a sign of misfolding, which in some proteins leads to disease (Dobson, (1999) *Trends Biochem. Sci.* 24: 329-32) while an increase in stability can be indicative of ligand binding (Schellman, (1975) *Biopolymers* 14: 999-1018). Despite their utility, stability measurements currently necessitate time-consuming experiments with pure protein samples. In proteomic experiments (Blackstock & Weir, (1999) *Trends Biotechnol.* 17: 121-27), where a large number of polypeptides often need to be analyzed, stability measurements are not practical.

Recent studies have demonstrated that hydrogen exchange coupled with electrospray ionization (ESI) mass spectrometry can qualitatively distinguish native-like proteins from unfolded polypeptides in partially purified samples (Rosenbaum et al., (1999) *J. Am. Chem. Soc.* 121: 9509-13) and can be used to study the kinetics and thermodynamics of folding (Miranker et al., (1996) *FASEB J.* 10: 93-101; Deng & Smith, (1999) *Ana. Biochem.* 276: 150-60). However, these studies did not disclose the quantitative analysis of native-like proteins.

Stability measurements are frequently performed to establish a polypeptide as a stably folded protein and to study the forces that lead to its folding. Conventional denaturation methods used for the analysis of protein stability have at least the following identified experimental limitations: 1) stability can only be measured under conditions where the protein is partially unfolded; 2) the energetics of localized fluctuations can not be easily measured; 3) many proteins cannot be analyzed because they aggregate during the course of denaturation; 4) stability measurements cannot be obtained in complex mixtures, extracts or living cells; 5) relatively large amounts of protein are required for analysis; and 6) denaturation experiments are time-consuming and not amenable to high-throughput analysis. These constraints drastically limit the number of biological problems that can be addressed through stability measurements.

Thermodynamic stability is an important biological property that has evolved to an optimal level to fit the functional needs of proteins. Therefore, investigating the stability of proteins is important not only because it affords information about the physical chemistry of folding, but also because it can provide important biological insights. A proper understanding of protein stability is also useful for technological purposes. The ability to rationally make proteins of high stability, low aggregation or low degradation rates will be valuable for a number of applications. For example, proteins that can resist unfolding can be used in industrial processes that require enzyme catalysis at high temperatures (Van den Burg et al., (1998) *Proc. Natl. Acad. Sci. U.S.A.* 95(5): 2056-60); and the ability to produce proteins with low degradation rates within the cell can help to maximize production of recombinant proteins (Kwon et al., (1996) *Protein Eng.* 9(12): 1197-202).

Stability measurements can also be used as probes of other biological phenomena. The most basic of these phenomena is biological activity. The ability of proteins to populate their native states is a universal requirement for function. Therefore, stability can be used as a convenient, first level assay for function. For example, libraries of polypeptide sequences can be tested for stability in order to select for sequences that fold into stable conformations and might potentially be active (Sandberg et al., (1995) *Biochem.* 34: 11970-78).

Changes in stability can also be used to detect binding. When a ligand binds to the native conformation of a protein, the global stability of a protein is increased (Schellman, (1975) *Biopolymers* 14: 999-1018; Pace & McGrath, (1980) *J. Biol. Chem.* 255: 3862-65; Pace & Grimsley, (1988) *Biochem.* 27: 3242-46). The binding constant can be measured by analyzing the extent of the stability increase. This strategy has been used to analyze the binding of ions and small molecules to a number of proteins (Pace & McGrath, (1980) *J. Biol. Chem.* 255: 3862-65; Pace & Grimsley, (1988) *Biochem.* 27: 3242-46; Schwartz, (1988) *Biochem.* 27: 8429-36; Brandts & Lin, (1990) *Biochem.* 29: 6927-40; Straume & Freire, (1992) *Anal. Biochem.* 203: 259-68; Graziano et al., (1996) *Biochem.* 35: 13386-92; Kanaya et al., (1996) *J. Biol. Chem.* 271: 32729-36).

The linkage between stability and binding has recently been implemented as a method to detect ligand binding (U.S. Pat. No. 5,679,582 to Bowie & Pakula). This method, however, does not take advantage of the high sensitivity available from an analytical technique such as MALDI mass spectrometry, and cannot be employed at the low protein levels that MALDI mass spectrometry can detect. Moreover, proteolytic methods can require additional steps to isolate and analyze proteolytic fragments and cannot be performed in an in vivo setting. Finally, this method cannot be employed to generate quantitative measurements of protein stability.

Thus, there remains substantial room for improvement in existing methods of screening for, quantitatively determining and beneficially employing protein stability measurements. A particularly desirable method would provide for the high throughput quantitative determination of protein stability, would require only very small quantities of sample, would permit in vivo measurement of protein stability and would generate data useful for a variety of stability-based applications. Until the disclosure of the present invention set forth herein, such a method was not available in the art.

SUMMARY OF THE INVENTION

A method of quantitatively determining the stability of a test protein under native conditions is disclosed. In a preferred embodiment, the method comprises: (a) providing a test protein; (b) contacting the protein with an exchange buffer comprising a denaturant and deuterium, the exchange buffer having a denaturant concentration; (c) contacting the test protein with a mass spectrometry matrix medium; (d) determining a change in mass of the test protein by mass spectrometry; (e) varying the denaturant concentration of the exchange buffer; (f) repeating steps (a)-(e) a desired number of times; and (g) quantitatively determining protein stability based on the change in mass of the test protein as a function of denaturant concentration, whereby the stability of a test protein under native conditions is quantitatively determined.

A method of detecting a binding event involving a test protein with a test ligand, is also disclosed. In a preferred embodiment, the method comprises: (a) providing a test protein; (b) providing a test ligand; (c) contacting the test ligand with the test protein to form a test mixture; (d) contacting the test mixture with an exchange buffer comprising a denaturant and deuterium, the exchange buffer having a denaturant concentration; (e) contacting the test mixture with a mass spectrometry matrix medium; (f) determining a change in mass of the test protein by mass spectrometry; (g) varying the denaturant concentration of the exchange buffer; (h) repeating steps (a)-(g) a desired number of times; and (i) analyzing the change in mass of the test protein as a function of denaturant concentration, whereby a binding event involving the test protein and the test ligand is detected.

Additionally, a method of quantitatively determining a change in the stability of a test protein imparted by the association of a test ligand with the test protein. In a preferred embodiment, the method comprises: (a) providing a test protein; (b) providing a test ligand; (c) contacting the test ligand with the test protein to form a test mixture; (d) contacting the test mixture with an exchange buffer comprising a denaturant and deuterium, the exchange buffer having a denaturant concentration; (e) contacting the test mixture with a mass spectrometry matrix medium; (f) determining a change in mass of the test protein by mass spectrometry; (g) varying the denaturant concentration of the exchange buffer; (h) repeating steps (a)-(g) a desired number of times; (i) calculating the stability of the test protein in the presence of the test ligand; and (j) quantitatively comparing the stability of the test protein in the presence of the test ligand with the stability of the protein in the absence of ligand to thereby generate a change in the stability of a test protein imparted by the association of a test ligand with the test protein.

Furthermore, a method of detecting an improperly folded mutant protein is disclosed. In a preferred embodiment, the method comprises: (a) contacting a mutant test protein with an exchange buffer comprising a denaturant and deuterium, the exchange buffer having a denaturant concentration; (b) contacting a mutant test protein with a mass spectrometry matrix medium; (c) determining a change in mass of the mutant test protein by mass spectrometry; (d) varying the denaturant concentration of the exchange buffer; (e) repeating steps (a)-(e) a desired number of times; (f) quantitatively determining protein stability based on the change in mass of the mutant test protein as a function of denaturant concentration; and (g) comparing the stability of the mutant test protein with the stability of a control, non-mutated test protein, a difference in the stabilities being indicative of an improperly folded mutant protein.

A method of detecting a disease characterized by protein misfolding is also disclosed. In a preferred embodiment, the method comprises: (a) providing a test protein suspected of being misfolded; (b) contacting the protein with an exchange buffer comprising a denaturant and deuterium, the exchange buffer having a denaturant concentration; (c) contacting the test protein with a mass spectrometry matrix medium; (d) determining a change in mass of the test protein by mass spectrometry; (e) varying the denaturant concentration of the exchange buffer; (f) repeating steps (a)-(e) a desired number of times; and (g) analyzing the change in mass of the test protein to determine a stability of the test protein; and (h) comparing the stability of the test protein suspected of being misfolded with a known stability of the test protein, wherein a change in stability of the test protein when compared with the known stability of the test protein is indicative of a disease characterized by protein misfolding.

Moreover, a method of identifying a protein that unfolds through one or more stable intermediates is disclosed. The method comprises: (a) providing a test protein suspected of unfolding through one or more intermediates; (b) contacting the test protein with an exchange buffer comprising a denaturant and deuterium, the exchange buffer having a denaturant concentration; (c) contacting the test protein with a mass spectrometry matrix medium; (d) determining a change in mass of the test protein by mass spectrometry; (e) varying the denaturant concentration of the exchange buffer, (f) repeating steps (a)-(e) a desired number of times; and (g) plotting the change in mass of the test protein as a function of denaturant concentration to generate an unfolding curve; (h) evaluating the unfolding curve, to thereby identify one or more stable intermediates.

In the above embodiments it is generally preferable that a test protein is disposed in a crude cell lysate or in vivo, which can comprise whole cells. A reference protein is preferably provided with the test protein. It is also preferable that the test protein has a mass of less than or equal to about 1,000,000 daltons. The test protein can be a multimeric protein. Additionally, it is preferable that the test protein, or a plurality of test proteins are disposed on a microtiter plate and the steps of the preferred embodiments disclosed are repeated for each test protein disposed on the microtiter plate. Finally, it is preferable that the denaturant is selected from the group consisting of detergents, guanidinium chloride and urea, that the mass spectrometry matrix material is a MALDI mass spectrometry matrix material, and that the mass spectrometry is MALDI mass spectrometry. Optionally, the MALDI mass spectrometry matrix material is selected from the group consisting of sinapinic acid, α-cyano-4-hydroxycinnamic acid, 2,5-dihdroxybenzoic acid, 2,5-dihydroxyacetophenone and 3-amino-4-hydroxybenzoic acid. Additionally, analysis can be performed using a computer program.

BRIEF DESCRIPTION OF THE DRAWINGS

FIG. 1A describes the exchange in the matrix solution at 2° C.

FIG. 1B describes the exchange in the crystallized solid matrix at room temperature.

DETAILED DESCRIPTION OF THE INVENTION

MALDI MS-HX Methods

Figure 1A:
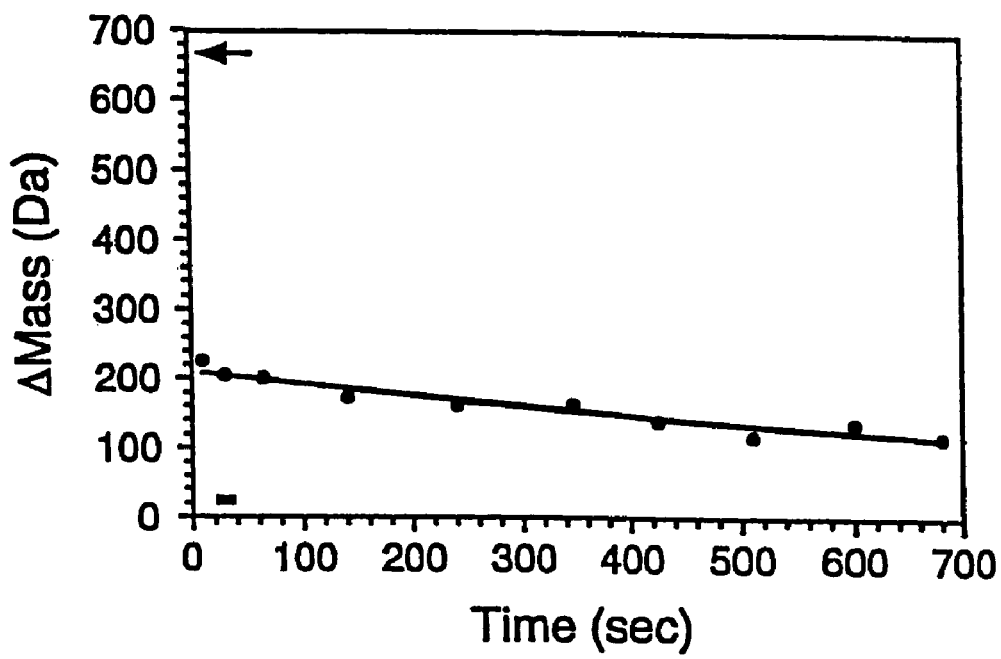
FIG. 1A is a line graph describing the exchange of a fully deuterated maltose binding protein (MBP) with the MALDI matrix as a function of time.

In accordance with the present invention, matrix-assisted laser desorption/ionization (MALDI) mass spectrometry is used to detect hydrogen/deuterium exchange. The MALDI technique is tolerant of impure samples that contain moderate levels of salts and other small molecule contaminants (Beavis & Chait, (1996) *Method. Enzmol.* 270: 519-51). Additionally, MALDI is adaptable to fast, high throughput screening because a large number of samples can be analyzed in a short period of time. Furthermore, MALDI is a very sensitive technique and can be used to study very small quantities of sample. These features make MALDI-based methods well suited for the measurement of hydrogen exchange as a function of denaturant concentration to give a quantitative measurement of the protein stability.

In one aspect of the present invention, the co-inventors disclose the use of hydrogen exchange as detected by mass spectrometry (MALDI MS-HX) to measure stabilities. In another aspect of the present invention, novel hydrogen exchange methodologies for examining MS-HX exchange data as applied to the stability of proteins in a number of biological applications are disclosed. In MS-HX, an observed hydrogen-deuterium exchange represents exchange of the entire protein rather than individual-hydrogens. The disclosure of the present invention demonstrates that MS-HX kinetics, preferably as a function of denaturant concentration, contains sufficient information to measure the stabilities (including the global stability) of a test protein. The MALDI MS-HX data disclosed herein for $\lambda_{6\text{-}85}$ variants is representative of this approach. The methods disclosed herein can be used to interpret the MALDI MS-HX data for virtually any protein. A MALDI-based MS-HX technique to rapidly measure stabilities (which can comprise samples disposed in or comprising crude cell lysates), examine protein-protein interactions and examine the stability of proteins in vivo (e.g. within the cytoplasm of a cell such as *E. coli* is additionally disclosed.

As an aspect of the present invention, a MALDI MS-HX method is disclosed. Generally, when employing the MALDI MS-HX method, one or more test proteins are subjected to hydrogen-deuterium (H/D) exchange by dilution into a series of deuterated exchange buffers containing different concentrations of denaturant, preferably ranging from 0 to 8 M, and including but not limited to 0.5M, 1.0M, 1.5M, 2.0M, 2.5M, 3.0M, 3.5M, 4.0M, 4.5M, 5.0M, 5.5M, 6.6M, 6.5M, 7.0M, and 7.5M denaturant concentrations. Representative denaturants can include, but are not limited to, guanidinium chloride, urea and detergents, and the like. The chemical denaturant has the effect of destabilizing the test protein's structure, which in turn has the effect of increasing the rate of global H/D exchange and increasing the rate of deuterium incorporation into the test protein at positions occupied by hydrogen atoms in the native test protein. After a specified exchange period (e.g. 5, 10, 15, 20, 25, 30, 35, 40, 45, 50, 55, 60, 70, 80, or 120 minutes) the deuterium content of the test protein sample(s) is the determined using MALDI mass spectrometry. The change in the mass of the protein ($\Delta$Mass) measurements recorded by MALDI in the MALDI MS-HX experiment only include those deuterated sites in the protein(s) that do not re-exchange during MALDI sample preparation. These sites are comprise, and are usually restricted to, those in the amide backbone of the protein because they have the slowest intrinsic exchange rates among the group of exchangeable hydrogens of a protein. Any back-exchange reaction that occur during MALDI sample preparation does not interfere with the analysis of the MALDI MS-HX data. Ultimately, the change in mass relative to the fully protonated sample is plotted as a function, of denaturant concentration [Denat.] and the data are fit to the MALDI MS-HX equation: $\Delta Mass = \Delta M_\infty + (\Delta M_0 - \Delta M_\infty) e^{-(<kint>/(1+Kfold))t}$, where $K_{fold} = e^{-(\Delta Gf + m[Denat.]/RT)}$, a derivation and detailed treatment of which is another aspect of the present invention and disclosed herein below.

Suprex Methods

As noted above and described further herein below, the methods of the present invention can be employed to study the stability of various unpurified samples (e.g. crude lysates). In this embodiment of the invention, the MALDI MS-HX method is denoted SUPREX (stability of unpurified proteins from rates of H/D exchange), further identifying its application to unpurified samples. Thus, the methods of the present invention are generally denoted throughout the present disclosure as MALDI MS-HX; when unpurified samples are studied the MALDI MS-HX method is denoted SUPREX. It will be recognized that SUPREX is only one aspect of the MALDI MS-HX methods of the present invention. Additional MALDI MS-HX methods are disclosed herein.

The methods of the present invention provide the ability to rapidly screen a large number of protein samples for the presence of stable structure. In a preferred embodiment, the method uses hydrogen exchange coupled with matrix-assisted laser desorption/ionization (MALDI) mass spectrometry to obtain quantitative measurements of stability from crude extracts (e.g. recombinant *E. coli* cultures grown in 96 well microtiter plates). In this embodiment, the method is referred to as SUPREX, reflecting its ability to tolerate unpurified samples.

Thus, with the methods disclosed herein, researchers can, for example, determine the stability (to within 0.5 kcal/mol) of proteins expressed in 200 microliter cultures grown, for example, in single wells of a 96-well plate. Researchers can also use the methods disclosed herein to determine whether a protein is stably folded under the conditions of a particular experiment to characterize its structure and/or function. Moreover, researchers can employ the methods disclosed herein characterize aggregated proteins not amenable to conventional biochemical assays; and identify small or large molecules that bind to a protein of interest by virtue of the effect of binding on protein stability.

I. Definitions

Following long-standing patent law convention, the terms "a" and "an" mean "one or more" when used in this application, including the claims.

As used herein, the term "uncharacterized protein" means a protein for which a complete ligand binding profile has not been established. Additionally, the term "uncharacterized protein" encompasses proteins for which a stability has not been conclusively established. Thus, an uncharacterized protein is a protein for which a comprehensive list of its natural (or non-natural) ligands has not been ascertained and/or does not have a known stability.

As used herein, the terms "unfolding curve", "stability curve", denaturation curve", "SUPREX curve", "MALDI MS-HX curve" and "MS-HX curve" are used interchangeably and mean a plot representing a change in mass of a test protein or other sample as a function of denaturant concentration.

As used herein, the term "in vivo" takes its ordinary meaning and means within an organism, including viruses. In the context of an in vivo test protein, the term means that the test protein is disposed in an organism.

As used herein, the term "native" means sample conditions wherein a denaturant is absent from the sample conditions. For example, native conditions can reflect the cytosolic composition found within a cell. The term "native" thus broadly encompasses "the absence of deniaturant."

As used herein, the term "test protein" means a peptide or polypeptide sample to be identified, detected or otherwise analyzed. In the present invention the identity of a test protein can be, but is not required to be, known. The identity of the test protein is preferably, but not necessarily, known to an extent sufficient to allow preparation of various ligands that can associated with the test protein, such as small molecules, peptides, nucleotides, modified nucleotides, polypeptides and chemically modified peptides and polypeptides, for practicing the methods of the present invention. Test proteins can include fragments, chimeric proteins, fusion proteins and analogs, as further disclosed and defined herein.

As used herein, the term "multimeric protein" means a protein comprising two or more proteins or polypeptides. The individual proteins or polypeptides comprising a multimeric protein can function cooperatively or independently.

As used herein, the term "ligand" means an agent that can associate with a test protein. The ligand can associate with the test protein when the target protein is in any form (e.g. folded, denatured, modified, binding one or more ligands, etc.). Ligands can be, but are not limited to, proteins, peptides, polypeptides, small molecules, oligonucleotides, complexes of two or more entities and modified forms of any of the listed moieties. Association can be of any form and can be, for example, a covalent interaction, an ionic interaction or a van der Waals interaction.

As used herein, the term "test ligand" means an agent that is being tested to determine if it associates with a test protein. The ligand can associate with the test protein when the target protein is in any form (e.g. folded, denatured, modified, binding one or more ligands, etc.). Test ligands can be, but are not limited to, proteins, peptides, polypeptides, small molecules, oligonucleotides, complexes of two or more entities and modified forms of any of the listed moieties. Association can be of any form and can be, for example, a covalent interaction, an ionic interaction or a van der Waals interaction.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "expression" generally refers to the cellular processes by which a polypeptide is produced from RNA.

As used herein, the term "isolated" means oligonucleotides substantially free of other nucleic acids, proteins, lipids, carbohydrates or other materials with which they can be associated, such association being either in cellular material or in a synthesis medium. The term can also be applied to polypeptides, in which case the polypeptide will be substantially free of nucleic acids, carbohydrates, lipids and other undesired polypeptides.

As used herein, the term "substantially pure" means that the polynucleotide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

As used herein, the term "biological activity" means any activity of a protein including, but not limited to, any observable effect flowing from interaction between a polypeptide and a ligand. Representative, but non-limiting, examples of biological activity in the context of the present invention include the association of a ligand or a test ligand with a test protein.

As used herein, the terms "β-sheet" and "beta-sheet" mean the conformation of a polypeptide chain stretched into an extended zig-zig conformation. Portions of polypeptide chains that run "parallel" all run in the same direction. Polypeptide chains that are "antiparallel" run in the opposite direction from the parallel chains.

As used herein, the terms "α-helix" and "alpha-helix" mean the conformation of a polypeptide chain wherein the polypeptide backbone is wound around the long axis of the molecule in a left-handed or right-handed direction, and the R groups of the amino acids protrude outward from the helical backbone, wherein the repeating unit of the structure is a single turn off the helix, which extends about 0.56 nm along the long axis.

As used herein, the terms "MBP gene product", "MBP protein", "MBP polypptide", "MBP peptide", are used interchangeably and mean peptides having amino acid sequences which are substantially identical to native amino acid sequences from an organism of interest and which are biologically active in that they comprise all or a part of the amino acid sequence of an MBP polypeptide, or cross-react with antibodies raised against an MBP polypeptide, or retain all or some of the biological activity (e.g., ligand binding ability) of the native amino acid sequence or protein. Such biological activity can include immunogenicity.

As used herein, the terms "$\lambda_{6-85}$ gene product", "$\lambda_{6-85}$ protein", "$\lambda_{6-85}$ polypeptide" and "$\lambda_{6-85}$ peptide" are used interchangeably and mean peptides having amino acid sequences which are substantially identical to native amino acid sequences from an organism of interest and which are biologically active in that they comprise all or a part of the amino acid sequence of a $\lambda_{6-85}$ polypeptide, or cross-react with antibodies raised against an $\lambda_{6-85}$ polypeptide, or retain all or some of the biological activity (e.g., ligand binding ability) of the native amino acid sequence or protein. Such biological activity can include immunogenicity.

As used herein, the "MBP gene product", "MBP protein", "MBP polypeptide", "MBP peptide" also include analogs of an MBP polypeptide. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct MBP analogs. There is no need for a "MBP gene product", "MBP protein", "MBP polypeptide", "MBP peptide" to comprise all or substantially all of the amino acid sequence of a MBP polypeptide gene product. Shorter or longer sequences are anticipated to be of use in the invention; shorter sequences are herein referred to as "segments". Thus, the terms "MBP gene product", "MBP protein", "MBP polypeptide", "MBP peptide" also include fusion, chimeric or recombinant MBP polypeptides and proteins comprising sequences of the present invention. Methods of preparing such proteins are disclosed herein and are known in the art.

As used herein, the terms "$\lambda_{6-85}$ gene product", "$\lambda_{6-85}$ protein", "$\lambda_{6-85}$ polypeptide" and "$\lambda_{6-85}$ peptide" also include analogs of a $\lambda_{6-85}$ polypeptide. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct $\lambda_{6-85}$ analogs. There is no need for "$\lambda_{6-85}$ gene product", "$\lambda_{6-85}$ protein", "$\lambda_{6-85}$ polypeptide" or "$\lambda_{6-85}$ peptide" to comprise all or substantially all of the amino acid sequence of a $\lambda_{6-85}$ polypeptide gene product. Shorter or longer sequences are anticipated to be of use in the invention; shorter sequences are herein referred to as "segments". Thus, the terms "$\lambda_{6-85}$ gene product", "$\lambda_{6-85}$ protein", "$\lambda_{6-85}$ polypeptide" and "$\lambda_{6-85}$ peptide" also include fusion, chimeric or recombinant $\lambda_{6-85}$ polypeptides and proteins comprising sequences of the present invention. Methods of preparing such proteins are disclosed herein and are known in the art.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product.

As used herein, the term "gene" is used for simplicity to refer to a functional protein, polypeptide or peptide encoding unit. As will be understood by those in the art, this functional term includes both genomic sequences and cDNA sequences. Preferred embodiments of genomic and cDNA sequences are disclosed herein.

II. Description of Tables

Table 1 is a table of data indicating the stability of various proteins as determined by SUPREX and CD techniques.

Table 2 is a table of dissociation constants of the B1 domain of streptococcal protein G for an Fc fragment based on binding-induced stability changes as detected by MALDI MS-HX at 22° C., pH 6.

Table 3 is a table of data representing the fractional hydrogen-deuterium exchange for a series of $\lambda^*_{6-85}$ mutants after 20 minutes at 23° C.

III. General Considerations

Within a polypeptide, certain labile hydrogen atoms can exchange freely with the surrounding solvent. Native structure protects a subset of these hydrogens from exchange (Hvidt & Nielson, (1996) *Adv. Protein Chem.* 21: 287-386), and some of these protected protons exchange only if the protein globally unfolds (Englander et al., (1996) *Curr. Opin. Struct. Biol.* 6: 18-23). The stability of a protein can be analyzed by monitoring the exchange rates of these "globally protected" hydrogens (Huyqhues-Despointes et al., (1999) *Nat. Struct. Biol.* 6: 910-12). Protein hydrogen exchange rates are typically measured by allowing labile protons to exchange with $D_2O$. The proton/deuteron exchange reaction is commonly measured by monitoring exchange via nuclear magnetic resonance (NMR) methods (Englander et al., (1996) *Curr. Opin. Struct. Biol.* 6: 18-23).

NMR has drawbacks when monitoring H/D exchange, however. These drawbacks can be compensated for by employing other analytical techniques, such as mass spectrometry. Mass spectrometry in particular is experimentally more convenient than NMR for many reasons. For example, mass spectrometry requires less protein than NMR, it is faster and simpler to use than NMR, it does not require complicated spectral assignments like those demanded by NMR and it does not require pure protein samples. Additionally, it is well-known that a limitation of NMR applications in biochemical research is its need for large quantities of sample.

IV. The Theoretical Basis for the Mass Spectrometry-Detected Hydrogen Exchange (MS-HX) Methods While it is not the desire of the present co-inventors to be bound by a specific theory of operation of the present invention, in the following section, a theoretical basis for the methods disclosed in the present invention is presented. The theoretical basis comprises a derivation of relationships correlating a change in mass of a sample (e.g. a test protein) with its stability. The following derivation forms a theoretical basis of the MALDI MS-HX methods of the present invention generally, and the SUPREX methods of the present invention particularly.

IV.A. Overall Theoretical Approach to the MS-detected Hydrogen Exchange (MS-HX) and SUPREX Techniques The thermodynamic stability ($\Delta G_{unfold}$) of proteins is commonly measured by denaturation experiments that use chemicals or temperature to unfold proteins (Schellman, (1987) *Annu. Rev. Biophys. Chem.* 16: 115-137). Resulting denaturation curves can be converted to stability measurements using two-state extrapolation models (Pace, (1986) *Method Enzymol.* 131: 266-80). Extrapolation to ambient conditions is required as $\Delta G_{unfold}$ can be measured during the transition phase of the denaturation experiment.

Another method commonly used to examine the thermodynamics of protein folding is native state hydrogen exchange (HX) (Bai et al., (1994) *Proteins* 20: 4-14). The ability of HX to measure extremely large unfolding equilibrium constants has long been recognized (Hvidt & Nielson, (1966) *Adv. Prot. Chem.* 21: 287-386). HX can measure stabilities under conditions where the protein is primarily folded. Two techniques that can be used to detect HX are NMR and mass spectrometry (Englander et al., (1996) *Curr. Opin. Struct. Biol.* 6: 18-23; Miranker et al., (1996) *FASEB J.* 10: 93-101).

IV.B. Hydrogen/Deterium Exchange, Generally

Certain hydrogen atoms within a polypeptide can exchange with the surrounding solvent. When a protein is placed in $D_2O$ a fraction of its protons, including the amide hydrogens (NH), will be replaced by deuterons over time. In the native structure of a protein some of the NHs are protected from exchange either because they are involved in hydrogen bonds or because they are not solvent accessible (Bai & Englander, (1996) *Proteins* 24: 145-51; Enalander et al., (1996) *Curr. Opin. Struct. Biol.* 6: 18-23; Clarke & Itzhaki, (1998) *Curr. Opin. Struct. Biol.* 8: 112-18). For these protected NHs, the exchange reaction is slow in comparison to their counterparts in unfolded polypeptides. The exchange of protected NHs can be analyzed based on the following model (Hvidt & Nielson, (1966) *Adv. Protein Chem.* 21: 287-386):

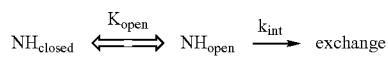

where $NH_{closed}$ and $NH_{open}$ are the conformations of the protein in which given NHs are incompetent or competent to exchange respectively, $K_{open}$ is the equilibrium constant for the opening reaction and $k_{int}$ is the intrinsic rate constant of the exchange reaction. Under normal physiological conditions, the opening reaction is usually in a rapid pre-equilibrium with respect to the exchange reaction (EX2 regime) and the observed rate constant ($k_{ex}$) is proportional to $K_{open}$. For a given amide hydrogen, there can exist multiple opening mechanisms (Mayo & Baldwin, (1993) *Science* 262: 873-76; Bai et al., (1995) *Science* 269: 192-97).

Two types of mechanisms that have been observed for all proteins studied to date are the "local opening" and "global opening" mechanisms. Global opening mechanisms involve the unfolding of the entire protein. Under this mechanism, the opening equilibrium-constant is equivalent to the global unfolding equilibrium constant as would be measured by traditional denaturation experiments. The possible conformational changes responsible for local opening are still debated (Miller & Dill, (1995) *Protein Sci.* 4: 1860-73; Bai & Englander, (1996) *Proteins* 24: 145-51; Li & Woodward, (1999) *Protein Sci.* 8: 1571-90). Local opening equilibrium constants for an NH are probably affected by both the stability of its localized region in the protein and its solvent accessibility. A number of proteins also demonstrate a third, subglobal mechanism of exchange through partially unfolded intermediates (Bai et al., (1995) *Science* 269: 192-97; Raschke & Margusee, (1997) *Nat. Struct. Biol.* 4: 298-304)

Under a given set of conditions, an NH can exchange through any of the above mechanisms. If the exchange is occurring through the global mechanism then the observed exchange rate is related to the global stability of the protein. On the other hand, if the exchange is occurring through subglobal or local mechanisms, then the observed exchange rate is reporting on the stability of the folding intermediate(s) in which the NH is open to exchange or the exchange characteristics of the local environment of the NH in the folded conformation. By conducting exchange as a function of denaturant concentration (an aspect of the present invention) or temperature researchers can decipher the contribution of each mechanism to the exchange rate of a given hydrogen (Mayo & Baldwin, (1993) *Science* 262: 873-76; Bai et al., (1995) *Science* 269: 192-97; Raschke & Margusee, (1997) *Nat. Struct. Biol.* 4: 298-304). Thus exchange experiments can be used to measure global stability, thermodynamics of intermediates and local dynamics of specific regions in the protein.

IV.C. Derivation of MALDI MS-HX and Relationships

According to the classical hydrogen exchange model: (Hvidt & Nielson, (1966) *Adv. Protein Chem.* 21: 287-386):

$$k_{ex}=k_{open}k_{int}/(k_{open}+k_{close}+k_{int}) \quad (1)$$

where $k_{ex}$ is the observed exchange rate for each hydrogen, $k_{open}$ and $k_{close}$ are the rate constants for the conformational changes leading to exchange competent and exchange incompetent states respectively and, $k_{int}$ is the exchange rate for the unprotected hydrogen.

Under EX2 conditions (where $k_{close}$ (or $k_{open}$) are much greater than $k_{int}$:

$$k_{ex}=K_{open}k_{int}/(K_{open}+1) \quad (2)$$

where $K_{open}$ is the equilibrium constant between the exchange competent and exchange incompetent conformations of the protein ($k_{open}/k_{close}$).

For the hydrogens that are exchanging through a global unfolding mechanism:

$$K_{open}=1/K_{fold} \quad (3)$$

Substituting (3) into (2):

$$k_{ex}=k_{int}/(1+K_{fold}) \quad (4)$$

Since $k_{int}$ is similar among the majority of the backbone amide hydrogens (Bai et al., (1993) *Proteins* 17: 75-86), the total exchange of the hydrogens that exchange through global unfolding can be estimated by a single rate constant. The increase in mass due to the exchange of globally exchanging protons (ΔMass) as a function of time can thus be estimated by the following first order rate equation:

$$\Delta Mass = \Delta M_\infty + (\Delta M_0 - \Delta M_\infty)e^{-k_{ex}t} \quad (5)$$

where $\Delta M_o$ is ΔMass before global exchange, $\Delta M_\infty$ is ΔMass after complete exchange and t is the exchange time. Substitution of Equation (4) into Equation (5) gives an equation for ΔMass vs Δ[Denat.]:

$$\Delta Mass = \Delta M_\infty + (\Delta M_0 - \Delta M_\infty)e^{-(<kint>/(1+Kfold))t} \quad (6)$$

where (Pace, (1986) *Method Enzymol*. 131: 266-80):

$$K_{fold}=e^{-(\Delta Gf+m[Denat.]/RT)} \quad (7)$$

Summarily, Equations (6) and (7) embody a relationship correlating an observed change in mass (ΔMass) with the stability of a sample ($\Delta G_f$). Interestingly, this relationship ties together an observed physical change in a sample, an observed increase in mass, with a thermodynamic property, stability, as represented by the term $\Delta G_f$.

In Equations (6) and (7), $\Delta G_f$ is the free energy of folding in the absence of denaturant, [Denat.] is the denatruant concentration, m is $\delta \Delta G_f/\delta[Denat.]$, R is the gas constant and T is the temperature in Kelvin. The m value determines the sharpness of the transition in the ΔMass vs [Denat.] plot.

Myers et al. have shown that m values can be estimated from the size of the protein (Myers et al., (1995) *Protein Sci.* 4: 2138-48). The average denaturant m value per residue for the 34 proteins in Table 1 of Myers et al. is 26 (pH=7.2) cal mol$^{-1}$ M$^{-1}$ per residue. According to this analysis, MBP and $\lambda_{6-85}$ are predicted to have m values of 9.7±2.6 and 2.1±0.6 kcal mol$^{-1}$ M$^{-1}$. These measurements are close to the previously reported experimental m values (12±1 and 2.1±0.1 kcal mol$^{-1}$ M$^{-1}$, respectively) measured from CD denaturation curves (Ghaemmaghami et al., (1998) *Biochem.* 37: 9179-85; Sheshadri et al., (1999) *Protein Sci.* 8: 1689-95). In order to assess the error involved in using estimated m values, as would be the case in a high-throughput screen of proteins, the calculated m values were used in this analysis. In Equation (6), $<K_{int}>$ is the average exchange rate of unprotected amide hydrogens and is a function of pH and temperature. In principle, $<k_{int}>$ can be estimated by averaging the values for all the backbone amide hydrogens using the measurements of Englander et al. (Bai et al., (1993) *Proteins* 17: 75-86). However, for these studies, the simple relationship $<k_{int}>=10^{pH-5}$ min$^{-1}$ was used to estimate the rate at room temperature and pH>4.

Thus, Equation (6) relates-denaturant concentration with the mass of a sample. This equation is a link between mass spectrometry data and the denaturant. The degree of unfolding of a protein is dependent upon the denaturant concentration (a factor that is present in Equation (6) via Equation (7)) and thus, the mass of a sample can be correlated with a degree of unfolding, stability and other properties. Equation (6) represents one aspect of the present invention, and facilitates the quantitative determination of a protein's stability and, under a given set of conditions, its state of denaturation.

The above theoretical basis applies generally to the MALDI MS-HX and SUPREX methods of the present invention. However, it should be noted that the stability curves obtained from MALDI MS-HX and SUPREX analysis (depicted in FIGS. 3B and 4 and described in detail herein below) are not identical to conventional denaturation curves, such as those generated by circular dichroism (CD) or other method. The midpoint of transition in conventional denaturation curves are a function of the stability and the m value of the protein. In the MALDI MS-HX and SUPREX curves, the midpoint is not only a function of these parameters but also depends on the time of exchange (t) and $<k_{int}>$.

$$C_{1/2}^{SUPREX}=C_{1/2}^{den}-(RT/m)In(<k_{int}>t/0.693-1) \quad (8)$$

where $C_{1/2}^{SUPREX}$ and $C_{1/2}^{den}$ are the midpoints of transition in the SUPREX analysis and conventional denaturation curves respectively and $<k_{int}>$ is itself a function of pH and temperature (Bai et al., (1993) *Proteins* 17: 75-86). As Equation (8) demonstrates, a SUPREX curve can be shifted to the left relative to a conventional denaturation curve, since $<k_{int}>$ t is always much greater than 0.693 (the numerical value of ln2).

Under the conditions used for the experiments described herein, this effect shifts the SUPREX curves of MBP and $\lambda_{6-85}$ by 0.5 and 2.4 M, respectively. Those of skill in the art will, therefore, recognize that the value of $C_{1/2}^{SUPREX}$ can be purposely altered by changing the pH, temperature, or exchange interval ("t"). High stabilities can be measured at higher pH and/or temperature, low stabilities at lower pH and/or temperature. Additionally, the exchange interval can conveniently range from a few minutes to hours. For example, according to Equation (8), the midpoint of the SUPREX curve for $\lambda_{6-85}$ can be shifted to the right by 1M relative to the curves shown in FIGS. 4A-4H by changing the pH to 5.9 and the exchange time to 11 minutes. In FIGS. 4A-4H, the curves are arranged in order of the stability of the mutant, from the least to the most stable: (A) A66G; (B) A63G; (C) WT; (D) G46A/G48A/A66G; (E) G46A/G48A/A49G; (F) Q33Y; (G) G46A/G48A; (H) Q33Y/G46A/G48A. This sort of adjustment makes SUPREX very flexible for measurements over a wide range of stabilities.

V. In Vivo Measurements of Protein Stability

Although stability is an important functional property, it has not been previously possible to quantitatively measure this property directly in vivo. Instead, researchers commonly assume that in vitro stability measurements are applicable in vivo, or use in vivo activity measurements as a qualitative probe of stability. One problem with currently available systems is that the complex milieu of molecules present in vivo can affect thermodynamic stability through changes in local osmolarity (Yancey et al, (1982) *Science* 217: 1214-22), oxidation potential (Frand et al., (2000) *Trends Cell. Biol.* 10: 203-10) and ligand concentration (Pace & McGrath, (1980) *J. Biol. Chem.* 255: 3862-65). A contingent problem with latter approach is that factors other than stability can influence activity (Sandberg et al., (1995) *Biochem.* 34: 11970-78).

In one aspect of the present invention, the methods of the present invention can be employed to directly and quantitatively measure the thermodynamic stability of proteins in vivo using hydrogen exchange detected by MALDI mass spectrometry. As an illustrative example, the in vivo methods of the present invention are capable of measuring the stability of proteins in the cytoplasm of viable cells (e.g. viable *E. coli* cells). In another example, the in vivo methods of the present invention can be employed to compare the in vivo stability of a protein (e.g. the monomeric λ repressor ($\lambda_{6-85}$)) with its in vitro stability under various conditions.

V.A. Preparation of In Vivo Test Protein Samples

Any protein of interest can be studied using the in vivo methods of the present invention. The following discussion will, therefore, be applicable mutatis mutandis to any protein of interest. Initially, a protein of interest disposed in a system can be provided by expressing it (preferably overexpressing it) in *E. coli* or other system, using a T7 or other vector. The bacteria or other system is grown in $H_2O$-based media. Methods of cloning and expressing a gene in bacteria and other systems are well known (see Sambrook et al., (1992) *Molecular Cloning: A Laboratory Manual*, Cold Spring Harbor, N.Y.) and will be apparent to those of skill in the art. Thus, the process of providing a test protein disposed in a system can vary with the system (e.g. bacteria, tissue, etc), and modifications of the general methods of preparing such a system will be apparent to those of skill in the art upon consideration of the present disclosure. Purely for illustrative purposes, the system referred to in the following discussion of in vivo methods is bacteria. However, the disclosed in vivo methods are not limited to bacterial systems.

After providing a test protein disposed in bacteria, hydrogen exchange can then be initiated. To initiate hydrogen exchange, the bacteria are transferred to a deuterated media. Time-course studies indicate that under these conditions the $D_2O$ component of the deuterated media freely diffuses across the cell membrane, and the solvent deuterons exchange with labile protons of the protein within the cytoplasm of the cell. Chloramphenicol can be added to the deuterated media in order to inhibit further protein synthesis during the course of the exchange reaction, thereby preventing deuteration during synthesis. After a given exchange period, the bacterial cells can then be lysed and the extent of exchange determined using MALDI mass spectrometry to measure the increase in mass, as shown in the general schematic diagram depicted in FIG. 8. Additional preparation steps, and modification of those presented above will be apparent to one of skill in the art upon considering the protein under study in view of the present disclosure.

V.B. Example of the In Vivo Methods of the Present Invention $\lambda_{6\text{-}85}$ is the monomeric form of the N-terminal domain of $\lambda$ repressor (Huang & Oas, (1995) *Biochem.* 34: 3884-92). In part, because the stability of the N-terminal domain, measured in vitro, qualitatively correlates with its degradation rate and hence the activity of the full-length protein in vivo (Reidhaar-Olson et al., (1990) *Biochem.* 29: 7563-71), variants of this protein having different stabilities were selected to illustrate the in vivo methods of the present invention. It has been proposed that this correlation in $\lambda_{6\text{-}85}$ exists because the folding kinetics of the protein, which occur on the millisecond time range in vitro (Burton et al., (1996) *J. Mol. Biol.* 263: 311-22), are in rapid pre-equilibrium relative to its proteolysis. This hypothesis is premised on the assumption that folding thermodynamics and kinetics observed in a simple buffer and dilute conditions are the same in intracellular environments. The present invention can be employed to test this assumption for any protein by employing hydrogen exchange to measure its stability in viable *E. coli* cells and compare the results to stability measurements in vitro in a typical buffer.

V.C. Analysis of Data Acquired by the in Vivo Methods of the Present Invention When partially folded intermediates are not present in vivo, MALDI MS-HX stability curves, such as those depicted in FIG. 10C, can be used to estimate protein stability using the following equation (Ghaemmaghami et al., (2000) *Proc. Natl. Acad. Sci. U.S.A.* 97: 8296-301):

$$\Delta \text{Mass} = \Delta M_\infty + (\Delta M_0 - \Delta M_\infty)e^{-(\langle kint \rangle/(1+Kfold))t} \quad (6)$$

where (Pace, (1986) *Method Enzymol.* 131: 266-80):

$$K_{fold} = e^{-(\Delta Gf + m[Denat.]/RT)} \quad (7)$$

$\Delta G_f$ is the free energy of folding, [Denat.] is the denaturant concentration, m is $\delta\Delta G_f/\delta[\text{Denat.}]$, $\langle k_{int}\rangle$ is the average exchange rate of unprotected amide hydrogens and is a function of pH and temperature (Ghaemmaghami et al., (2000) *Proc. Natl. Acad. Sci. U.S.A.* 97: 8296-301). Equation (6) can be used to fit the MALDI MS-HX data for both in vivo and in vitro experiments, as demonstrated in FIG. 10C and described herein. In FIG. 10C, data for $\lambda^*_{6\text{-}85}$ at 15° C. is presented for: (●) cell lysates at pH 8; (♦) cytoplasm of viable *E. coli* cells grown in normal LB media; and (▼) MALDI MS-HX of viable *E. coli* cells equilibrated in hyperosmotic (1.2 M NaCl) LB media. The curves yield stabilities of 6.7+−0.13 and 6.7+−0.2 kcal/mol in lysates and cells, respectively. The difference in the midpoints of the MALDI MS-HX and CD curves results from the ability of MALDI MS-HX to detect small populations of denatured protein and is not indicative of a large stability change. The measured in vivo stability is 6.7±0.13 kcal/mol and the in vitro stability of the protein obtained by performing H/D exchange on lysed bacteria at pH 8 is 6.7±0.2 kcal/mol.

Figure 10A:
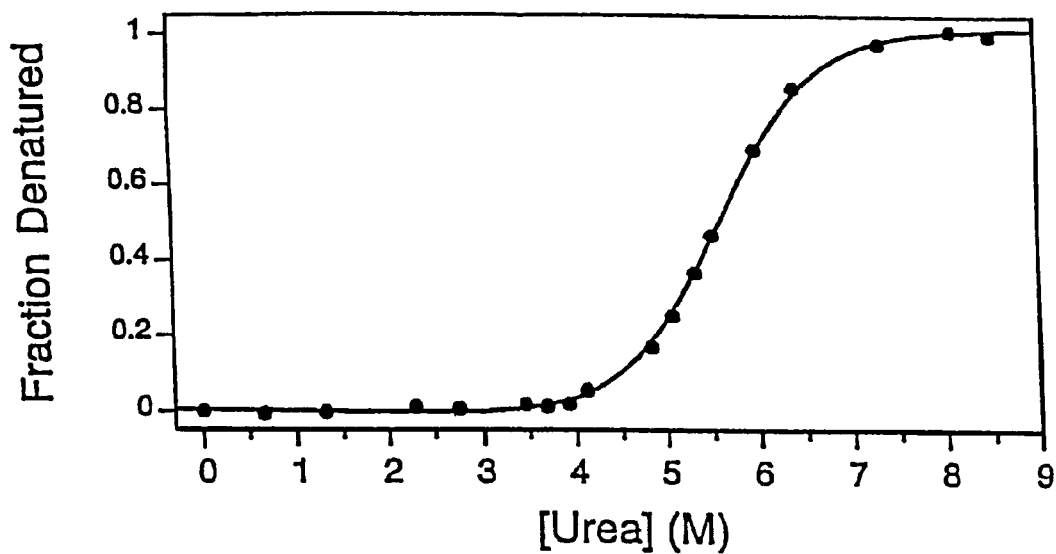
FIG. 10A is a line graph describing a conventional denaturation curve acquired by employing CD and purified protein.

FIG. 10A shows a plot of the fraction denatured as determined by circular dichroism (CD) of a 10 μM solution of the pure protein in a 50 mM sodium acetate, 50 mM sodium phosphate, 100 mM NaCl, pH 8 buffer. The curve represents the best fit of the data using the linear extrapolation method (Pace, (1986) *Method Enzymol.* 131: 266-80), yielding a stability of 6.16+−0.13 kcal/mol. Similar plots can be generated for any protein of interest. Continuing with the example of $\lambda_{6\text{-}85}$, conventional two-state analysis of the CD denaturation curve (Pace, (1986) *Method Enzymol.* 131: 266-80) yields a stability estimate for $\lambda_{6\text{-}85}$ of 6.16±0.13 kcal/mol.

If folding equilibrium constants measured in vitro are applicable in vivo, then it is reasonable to conclude that the kinetics of $\lambda_{6\text{-}85}$ are also comparable in and out of the cell. If this were not the case, then the rate constants for folding and unfolding would have to increase or decrease in vivo by the same factor, in order to maintain a constant equilibrium constant (i.e. stability), an event that seems unlikely. Thus, it is likely that the cellular lifetime of the native state of the N-terminal domain of λ repressor is approximately 30-milliseconds (Huang & Oas, (1995) *Proc. Natl. Acad. Sci. U.S.A.* 92: 6878-82). If this is indeed the case, then this protein, when not bound to DNA, samples the denatured state thousands of times during its lifetime in the cell. In a growing number of proteins, the unfolding rate appears to be faster than the folding rate and thus the proteins are predominately unfolded in vitro (Wright & Dyson, (1999) *J. Mol. Biol.* 293: 321-31). The SUPREX method of the present invention can be particularly useful for determining whether these "intrinsically unstructured" proteins are as unstable in vivo as they appear to be in vitro.

Figure 9:
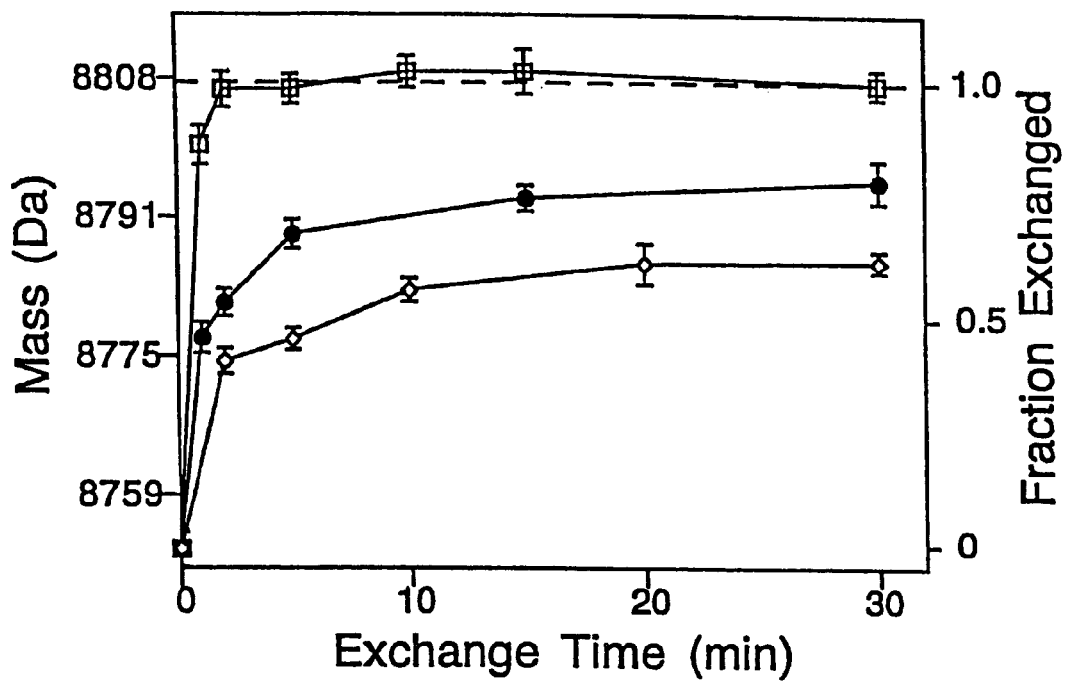
FIG. 9 is a line graph describing the increase in mass of MBP as a function of the length of the time subject *E. coli* cells were exposed to a deuterated media in which they were incubated (the exchange time).

FIG. 9 shows a plot of the increase in mass versus the length of the time the *E. coli* cells were exposed to deuterated media (i.e. the exchange time). In FIG. 9, the mass of $\lambda_{6\text{-}85}$ versus H/D exchange time in vivo at is presented for three temperatures, 15° C. (open diamonds), room temperature (closed circles), and 37° C. (open squares). The exchange was conducted in LB media at pH 7. The mass at time=0 was determined by measuring the mass in an all-protonated media. The dashed line shows the effective mass of the fully exchanged protein. The left y-axis shows the measured mass and the right y-axis shows the calculated fraction exchanged.

Similar plots can be prepared for any system expressing a protein of interest. In this illustrative example of the present invention, the exchange was conducted at three different temperatures. As the exchange time increases, more deuterons replace the protons within the protein and the mass increases. This exchange reaction occurs faster at higher temperature.

The rates of H/D exchange are strongly pH dependent (Englander et al., (4996) *Curr. Opin. Struct. Biol.* 6: 18-23). Above about pH 4 the exchange rates of amide hydrogens increase ten fold for every pH unit. It has been shown that *E. coli* maintains an intracellular pH of about 8 when the extracellular pH is between 6 and 9 (Padan et al., (1976) *Eur. J. Biochem.* 63: 533-41). The effect of extracellular pH on the extent of exchange after 20 minutes at room temperature is listed in Table 3. For the G46A/G48A thermostable variant of monomeric lambda repressor ($\lambda_{6-85}$), changing the extracellular pH from 7 to 8 did not change the rate of hydrogen exchange within the cell. In contrast, exchange experiments conducted with cells lysed with a non-ionic detergent showed significantly accelerated exchange at pH 8 compared to pH 7. Importantly, the exchange rate in cell lysate at pH 8 was equivalent to exchange in vivo consistent with an estimate of an intracellular pH of 8. Thus, in practicing the present invention, those of skill in the art will recognize that pH effects should be taken into account when designing experiments.

The in vivo methods of the present invention can be employed to detect stability perturbations within a cell. Table 3 presents the effect perturbations caused by amino acid substitution and changes in the external environment on the extent of in vivo exchange of $\lambda^*_{6-85}$, which serves as an illustration of the present methods. The Q33Y substitution has been shown to increase the in vitro stability of the protein by 1.7 kcal/mol (Ghaemmaghami, et al., (2000) *Proc. Natl. Acad. Sci. U.S.A.* 97: 8296-301). As shown in Table 3, after 20 minutes, the $\lambda_{6-85}$(Q33Y) variant exchanges less than the $\lambda_{6-85}$ variant suggesting that the stabilizing effect of this substitution is present in vivo. Record and co-workers have recently shown that the cytoplasm of *E. coli* grown in high-osmolarity medium contains less water and higher concentrations of naturally occurring osmolytes (Record et al., (1998) *Trends Biochem. Sci.* 23: 143-48; Record et al., (1998) *Trends Biochem. Sci.* 23: 190-94). It has been proposed that these physiological effects should increase intracellular protein stability by decreasing the water content, thereby favoring the less hydrated native state. Table 3 lists the extent of $\lambda_{6-85}$ exchange in *E. coli* cells that were equilibrated for 2 hours in a protonated medium containing 1.2 M NaCl prior to exchange in deuterated media that also contained 1.2 M NaCl. The reduced extent of exchange compared to the normal LB media, which contained 0.12 M NaCl, is consistent with the predicted in vivo stabilization. Also shown in Table 3 is the effect of adding 3 M urea to the exchange buffer, which increases the extent of exchange, suggesting that urea is destabilizing the protein. The increase in exchange caused by urea is evident even after 5 minutes indicating that the urea is rapidly diffusing inside the cell and destabilizing the protein. Thus, one advantage of the present invention over prior art systems is its ability to detect stability perturbations within a cell, an ability heretofore thought unattainable.

Because the cell membrane is permeable to urea, it is possible to conduct MALDI MS-HX denaturation experiments in vivo. Continuing with the present example, in vivo MALDI MS-HX experiments can be performed with cells expressing $\lambda_{6-85}$ at 15° C. using a 20 minute exchange time (FIG. 10C, diamonds). These experiments were carried out at an external pH of 7. As more urea is added, the extent of exchange increases as a result of global destabilization. This unfolding is not evident when the cells are grown in a hyper-osmotic external environment (FIG. 10C, triangles), consistent with the observations discussed above. FIG. 9C also depicts a conventional in vitro SUPREX experiment in which the cells were lysed with a non-ionic detergent before exchange was initiated at pH 8 (FIG. 10C, circles), which is indistinguishable from the in vivo denaturation curve in normal LB media. These observations indicate that the stability of $\lambda_{6-85}$ is the same in intact cells and cell lysates. This set of experiments further demonstrate the ability of the present invention to facilitate in vivo measurements of protein stability.

Figure 10B:
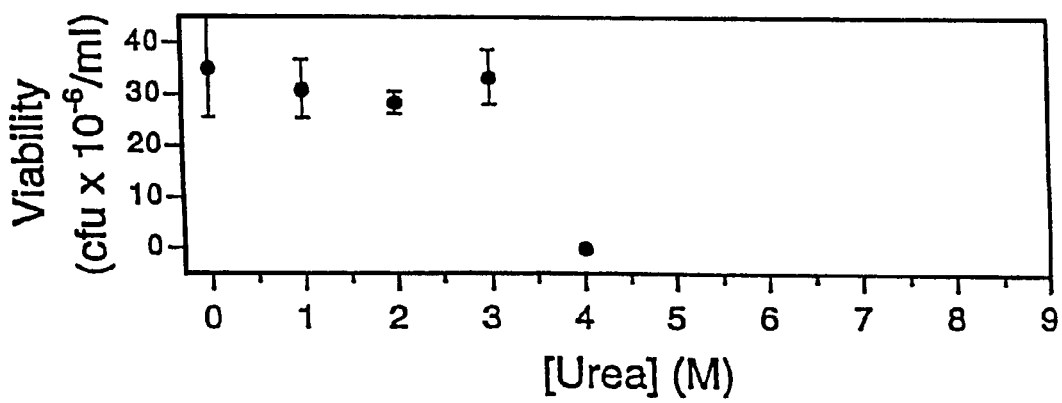
FIG. 10B is a scatter plot describing the viability of *E. coli* when placed in various concentrations of urea for 30 minutes at 23° C.
Figure 10C:
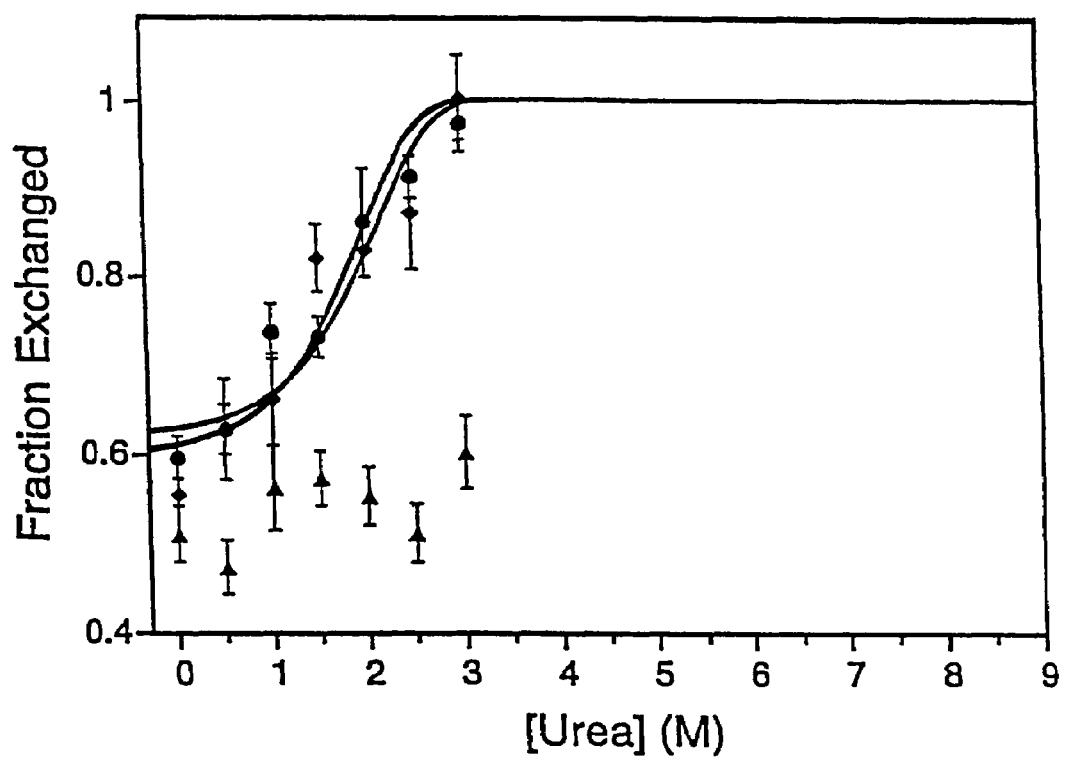
FIG. 10C is a line graph describing the stability of $\lambda^*_{6\text{-}85}$, as determined by SUPREX.

It should be noted that although *E. Coli* might not grow efficiently in 3M urea, exposure to 3M urea for up to 20 minutes does not perturb the viability of the cells. FIG. 10B shows the number of *E. coli* colony forming units in the culture after exposure to urea for 30 minutes relative to no exposure to denaturants. The number of colonies observed does not decrease until above 3M urea, at which point cell viability drops to almost nothing, presumably because crucial proteins are irreversibly denatured. Under the conditions of the denaturation experiments disclosed herein, where urea concentration did not exceed 3 M, the cells remain intact and viable. In FIG. 10B, *E. coli* placed in various concentrations of urea for 30 minutes were studied at 23° C. (closed circles) and 15° C. (open circles).

Recent genomic sequencing efforts have provided the DNA sequences of thousands of previously unknown genes (Moore et al., (1997) *J. Mol. Biol.* 272: 336-47). Assigning function to all these unknown sequences is envisioned as one of the major scientific tasks of the coming decades. Whether this process involves biochemical analysis or structure determination, the magnitude of the task is so great that it will be important to intelligently select out the most promising candidates for study. Many cellular proteins are not stable under typical in vitro conditions. Since both structural and functional analyses require stability, the MALDI MS-HX and SUPREX methods of the present invention can act as a fast screen for selecting promising stable proteins for further study. Similarly, large-scale screening of cloned and expressed polymorphic genes-could efficiently aid in the identification of alleles that, code for unstable proteins that cause a diseased phenotype.

The methods disclosed in the present invention offer the first direct analysis of protein folding thermodynamics in vivo. This approach is useful in applications where the measurement of the in vivo stability of the protein provides important biological insights. Such studies can include, among others, studies of chaperone function, amyloid formation and heat and osmotic shock response of cells.

The in vivo methods of the present invention, thus, can yield stability data that mirrors the disposition of a test protein as it exists inside a cell. This ability to generate accurate measurements of in vivo protein stability using a mass spectrometry-based technique has been heretofore unavailable to researchers. It will be appreciated that all of the applications of the MALDI MS-HX and SUPREX methods of the present invention can be performed in vivo using the steps disclosed herein. In practice, this ability makes protein stability data more indicative of the stability of a protein, as it exists inside a cell. This enhanced insight into protein stability can translate into more reliable and accurate screening methods, diagnostic procedures, protein folding research and any other application where protein stability plays a role.

VI. Application of the Derived Relationships

In the following sections, the wide range of applicability of the above derived relationships is illustrated by several specific examples. These examples are presented for illustrative purposes only and those of skill in the art will, upon consideration of the present disclosure, undoubtedly appreciate other applications of the mathematical relationships and the methods applying those relationships that form the various aspect of the present invention.

VII Method of Quantitatively Determining the Stability of a Test Protein

In a preferred embodiment, the MALDI MS-HX methods of the present invention can be applied to the study of protein stability. In this embodiment of the present invention, the following general procedure can be employed. Modifications of the following procedure will be apparent to those of skill in the art upon consideration of the present disclosure.

VII.A. Hydrogen-Deuterium Exchange in Protein Stability Studies

In one aspect of the present invention, hydrogen exchange as detected by MALDI mass spectrometry is employed to analyze the global stability of the protein. As deuterons replace protons in the protein the protein gains mass. The increase in mass can be followed as a function of time with a MALDI mass spectrometer, as disclosed in the present invention. The addition of denaturants globally destabilizes the protein and increases the observed exchange rate by increasing the rate of the global exchange mechanism. By conducting exchange for a given amount of time as a function of denaturant concentration, a denaturation curve can be obtained (Ghaemmaghami et al., (2000) Proc. Natl. Acad. Sci. U.S.A. 97: 8296-301).

Figure 6A:
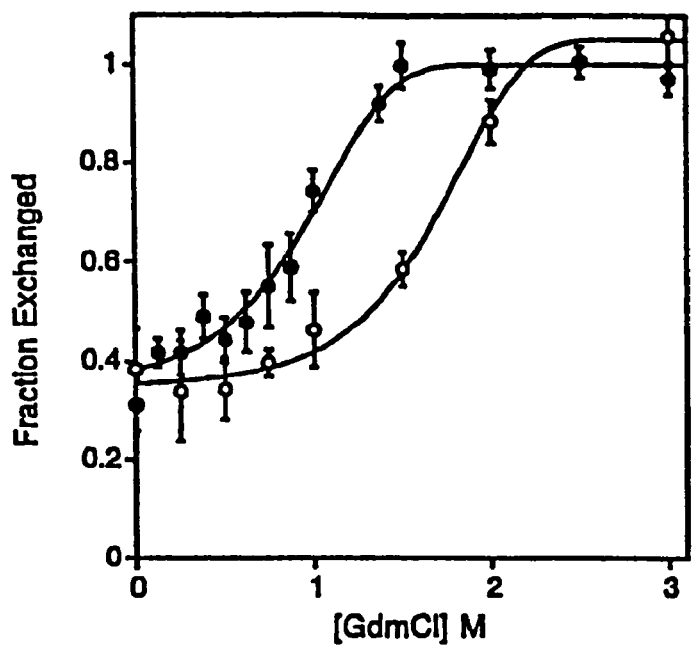
FIGS. 6A-6D are line graphs describing MALDI MS-HX stability curves for the B1 domain of streptococcal protein G (B1 domain) in the absence (closed circles) and presence (open circles) of Fc fragment.
Figure 6B:
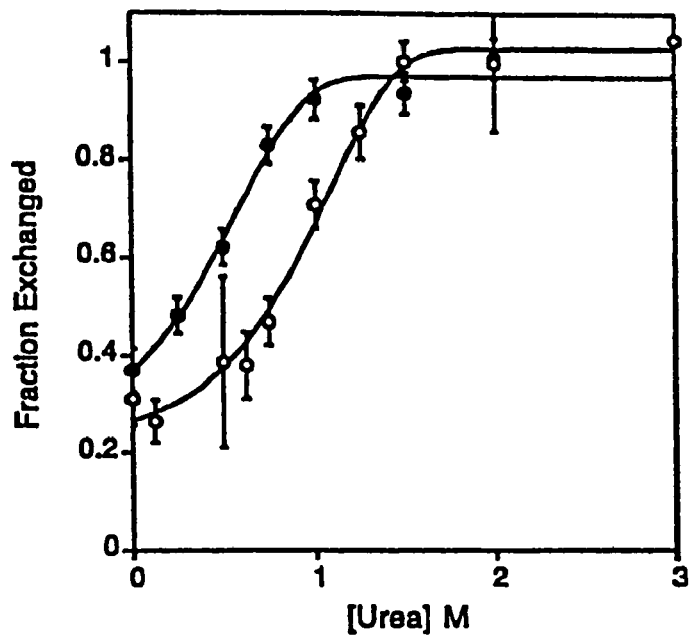
Figure 6C:
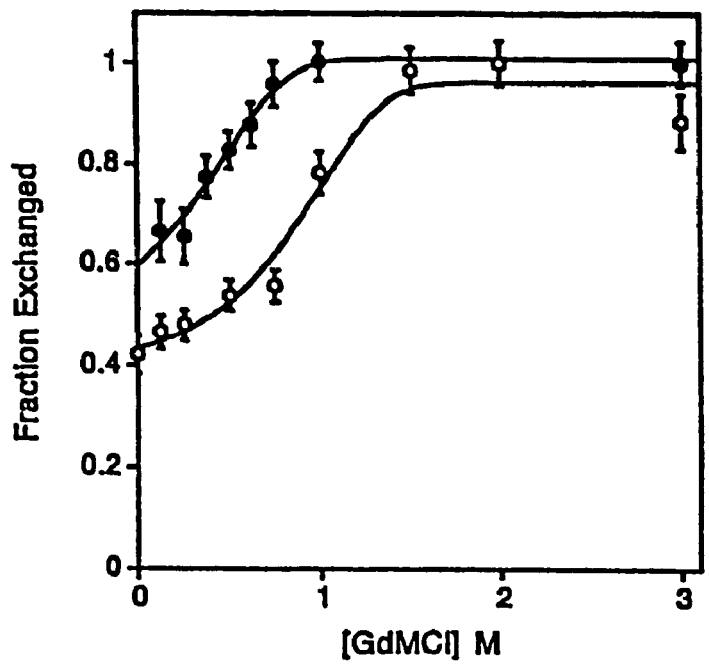
Figure 6D:
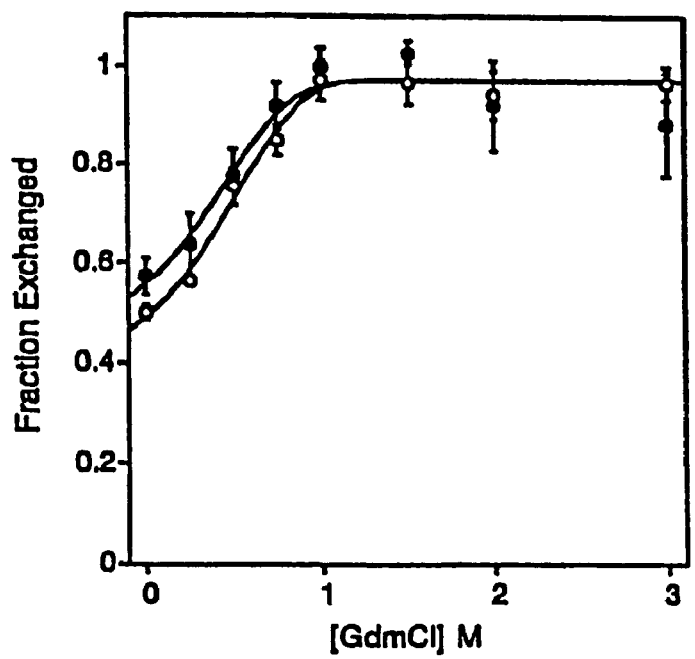

The following non-limiting embodiment of the present invention is presented purely for illustrative purposes; those of skill in the art will recognize that the example discloses a general methodology and can be applied mutatis mutandis to any protein of interest. FIGS. 6A-6D depicts unfolding curves for B1 domain where exchange was allowed to occur for three different time intervals in the absence and presence of Fc fragment. The MALDI-HX stability curves of FIGS. 6A-6D are for B1 domain at 22° C., pH 6 in the absence (closed circles) and presence (open circles) of 24 µM Fc fragment. FIG. 6A is WT*, 10 minutes of exchange, FIG. 6B is WT*, 90 minutes of exchange, FIG. 6C is WT* 180 minutes of exchange and FIG. 6D is E27A mutant, 90 minutes of exchange. The measured stabilities are listed in Table 2. The sigmoidal transition in the plots result from the increase in exchange rate incurred by GdmCl induced destabilization. As the protein is destabilized, a larger increase in mass occurs in the given exchange time. In the presence of 3M GdmCl, all exchangeable protons in B1 domain are replaced by deuterons after ten minutes of exchange. Table 2 lists the measured mass of the protein after complete exchange. The calculated fraction exchanged (FE) values are also plotted in FIGS. 6A-6D. The initial baseline of the curve corresponds to the fast-exchanging local NHs that exchange with solvent rapidly in a denaturant independent manner (Ghaemmaghami et al., (2000) Proc. Natl. Acad. Sci. U.S.A. 97: 8296-301). When the present invention is employed to study a given protein or set of proteins, the disclosed, or a similar method, of presenting exchange data can be adopted.

VII.B. General Sample Preparation Protocol

The general protocol for the preparation of samples can comprise the following general protocol. A protein of interest (i.e. a test protein) can be cloned into a suitable expression vector, such as a T7 expression vector and the protein expressed in a convenient cell-line, for example BL21-(DE3) E. coli cells. Cells can conveniently be grown on 96 well plates or other support.

The MALDI MS-HX and SUPREX methods disclosed in the present invention are applicable to expression cell types other than bacteria, thus allowing studies to be performed under nearly in vivo conditions. Standard techniques, such as those described above, can be used with variety of host-expression vector systems can be utilized. These include but are not limited to microorganisms such as bacteria (e.g., E. coli, B. subtilis) transformed with recombinant bacteriophage DNA, plasmid DNA or cosmid DNA expression vectors containing desired coding sequences; yeast (e.g., Saccharomyces, Pichia) transformed with recombinant yeast expression vectors containing desired coding sequences; insect cell systems infected with recombinant virus expression vectors (e.g., baculovirus) containing desired coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing desired coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; lentiviral vectors).

In bacterial systems a number of expression vectors can be advantageously selected. For example, when large quantities of protein are to be produced, vectors which direct the expression of high levels of protein products that are readily purified can be desirable. Such vectors can include but are not limited to the E. coli expression vector pUR278 (Ruther et al., (1983) EMBO J. 2: 1791), in which a coding sequence can be ligated individually into the vector in frame with the lac Z coding region so that a protein containing a portion of the lac Z product is provided; pIN vectors (Inouye et al., (1985) Nucleic Acids Res. 13: 3101-09; Van Heeke et al., (1989) J. Biol. Chem. 264: 5503-9); and the like. A T7 vector is a preferred vector. pGEX vectors can also be used to express foreign polypeptides, such as a protein containing glutathione S-transferase (GST). In general, such fusion proteins are soluble and can easily be purified from lysed cells by adsorption to glutathione-agarose beads followed by elution in the presence of free glutathione.

Expression of the test protein can be induced by the addition of IPTG or other compound. Cells can then be pelleted and lysed using a lysis solution, such as a BUGBUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 μL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 μL aliquot into the column, waiting five seconds, and expelling the aliquot to waste. The column can then be rinsed with a 2 μL aliquot of an ice-cold, aqueous solution comprising 5% MeOH and 0.1% TFA in order to wash away excess denaturant. Finally, the test protein can be eluted from the column and directly onto a MALDI sample stage using approximately 1 μl of the ice-cold MALDI matrix solution.

Figure 1B:
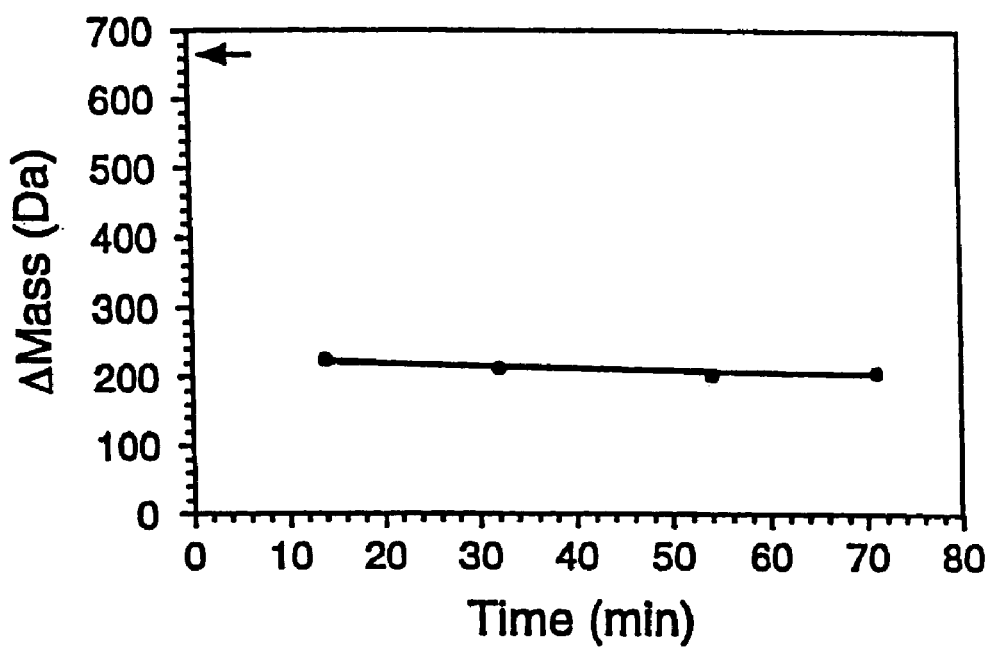
FIG. 1B is a line graph describing the exchange of a fully deuterated MBP with the MALDI matrix as a function of time.
Figure 2A:
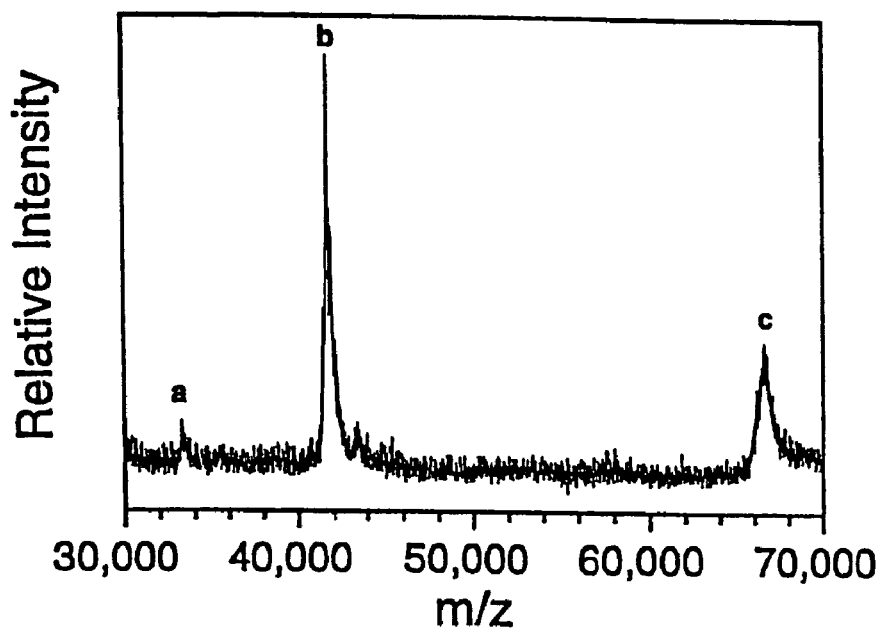
FIG. 2A is a MALDI-TOF mass spectrum describing hydrogen exchange of a non-exchanged (all protonated)-sample of MBP, as detected by MALDI.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of 0.001 $s^{-1}$ (FIG. 1A). Once the matrix forms a solid crystal, the exchange rate slows to a rate of 0.001 $min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

The observed mass of a test protein can then be correlated with its stability. A correlation can be achieved by fitting the observed data to equation (6) to obtain a value of $\Delta G_f$, which represents the stability of the test protein. As described further below, denaturation curves can offer additional insight into the stability of a test protein.

For illustrative purposes, the B1 domain of streptococcal protein G (B1 domain) has been adopted as a test protein, which was prepared according to the above general protocol. Specific details of the preparation of this and other samples can be found throughout the present disclosure and the Laboratory Examples. The following discussion, then, makes reference to this protein, although any protein can serve as a test protein.

VII.C. Acquisition of a Stability Value

Data generated using the MALDI MS-HX methods can be fit to an appropriate equation, for example Equation (6), to determine the stability of a test protein under native conditions. A summary of results generated by employing this methodology is presented in Table 1. This analysis broadly involves the extrapolation of the linear free energy versus denaturant concentration curves to 0 M.

VIII. Method of Detecting a Binding Event Involving a Test Protein and a Test Ligand It has long been known that the binding of a substrate to the native conformation of a protein increases its thermodynamic stability (Warren et al., (1964) *Biochem. J.* 93: 409-19; Citri, (1973) *Adv. Enzymol. Relat. Areas Mol. Biol.* 37: 397-648; Goldberg & Dice, (1974) *Annu. Rev. Biochem.* 43: 835-69; Pace & McGrath, (1980) *J. Biol. Chem.* 255: 3862-65; Pace & Grimsley, (1988) *Biochem.* 27: 3242-46). The relationship between stability changes and dissociation constants have been quantitatively established (Schellman, (1975) *Biopolymers* 14: 999-1018). Experimental and data analysis designs based on this known relationship form an aspect of the present invention.

Measuring binding by exploiting the relationship between stability and dissociation constants offers advantages over conventional titration methods such as Scatchard analysis (Segel, (1975) *Enzyme Kinetics*, John Wiley & Sons, New York, N.Y.). For example, the concentrations of a test protein (such as an enzyme) can be much higher than the applicable dissociation constant(s) (Xie et al., (2000) *J. Am. Chem. Soc.* 122: 11533-34). This flexibility in concentration permits very tight dissociation constants to be measured without the need to resort to other detection methods.

Additionally, it is possible to partition the changes in observable binding energy into energetic effects on the free and bound form of the protein. For example, if a mutation is found to increase the dissociation constant, it can be determined whether this was due to a decrease in'the stability of the protein or to a decrease in the interaction energy. This ability adds another facet that can be considered when analyzing binding analysis data.

Furthermore, the link between stability and dissociation constants is a general relationship and can be applied to all proteins, regardless of size, function or amino acid composition. Moreover, there is no need for supplemental, potentially time-consuming manipulations, such as labeling reactions. This general strategy has been employed to measure the dissociation constants of a number of small ligands to proteins (Pace & McGrath, (1980) *J. Biol. Chem.* 255: 3862-65; Pace & Grimsley, (1988) *Biochem.* 27: 3242-46; Schwartz, (1988) *Biochem.* 27: 8429-36; Brandts & Lin, (1990) *Biochem.* 29: 6927-40; Straume & Freire, (1992) *Anal. Biochem.* 203: 259-68; Graziano et al., (1996) *Biochem.* 35: 13386-92; Kanaya et al., (1996) *J. Biol. Chem.* 271: 32729-36; Xie et al., (2000) *J. Am. Chem. Soc.* 122: 11533-34).

The aforementioned, studies employed differential scanning calorimetry (DSC) or temperature and chemical-denaturations as detected by circular dichroism (CD) or other spectroscopic probes to detect binding-induced stability changes. These detection techniques impose significant practical limitations on the linked stability-binding approach. They are inherently low throughput techniques that require fairly large quantities of pure protein. Furthermore, the presence of significant concentrations of other proteins cannot be tolerated as they can obscure the signal of the protein of interest. Thus, these techniques cannot be applied to unpurified samples. This makes it difficult to analyze protein-protein interactions because the substrate protein must be present in equivalent or excess concentrations relative to the protein whose signal is being detected.

The MALDI MS-HX methods of the present invention (including SUPREX) can detect substrate induced stability increases using hydrogen exchange as detected by MALDI mass spectrometry. The MALDI MS-HX methods of the present invention can tolerate the excess presence of other proteins and can be used to measure protein-protein interactions in crude extracts. In one aspect of the present invention, SUPREX can be employed to analyze the binding of one protein with another in an unpurified cell lysate. To illustrate this point and demonstrate the uncomplicated application power and sensitivity of the methods of the present invention, the binding of the B1 domain of staphylococcal protein G (B1) to the Fc fragment of goat IgG (Fc) was studied.

It will be appreciated that the following is an illustrative example and the methods disclosed herein can be applied to any protein; indeed, this is an advantage of the methods of the present invention.

VII.A. Mathematical Relationships Linking Fraction Exchanged (FE), Substrate Concentration and the Dissociation Constant for a Test Protein and a Test Ligand The mathematical relationships useful for determining a fraction of hydrogens exchanged with deuterons can be derived similarly to those relationships previously derived linking stability and change in mass. A derivation can start with the classical hydrogen exchange model (Hvidt & Nielson, (1966) *Adv. Protein Chem.* 21: 287-386):

$$k_{ex}=k_{open}k_{int}/(k_{open}+k_{close}+k_{int}) \quad (1)$$

where $k_{ex}$ is the observed exchange rate for each hydrogen, $k_{open}$ and $k_{close}$ are the rate constants for the conformational changes leading to exchange competent and exchange incompetent states, respectively, and $k_{int}$ is the exchange rate for the unprotected hydrogen. Under EX2 conditions where $k_{close}$ (or $k_{open}$) are much greater than $k_{int}$:

$$k_{ex}=K_{open}k_{int}/(K_{open}+1) \quad (2)$$

where $K_{open}$ is the equilibrium constant between the exchange competent and exchange incompetent conformations of the protein ($k_{open}/k_{close}$). For the hydrogens that are exchanging through a global unfolding mechanism, $$K_{open}=K_{unfold} \quad (10)$$

Where $K_{unfold}$ is the global unfolding equilibrium constant. Substituting (10) into (2):

$$k_{ex}=K_{unfold}k_{int}/(1+K_{unfold}) \quad (11)$$

Since $k_{int}$ is similar among the majority of the backbone amide hydrogens (Bai et al., (1994) *Proteins* 20: 4-14), the total exchange of the hydrogens that exchange through global unfolding can be estimated by a single rate constant. The increase in mass due to the exchange of globally exchanging protons as a function of time can thus be estimated by the following first order rate equation:

$$\text{Mass}=M_{deut}-A*e^{-t*kex} \quad (12)$$

$M_{deut}$ is the mass of the fully deuterated protein, A is the amplitude of the mass increase, t is the exchange time. The change in mass can be normalized to obtain fraction exchanged (FE):

$$FE=(\text{Mass}-M_{prot})/(M_{deut}-M_{prot}) \quad (13)$$

Where $M_{prot}$ is the mass of the fully protonated protein. Equation (13) can be transformed to:

$$FE=1-A_{FE}*e^{-t*kex} \quad (14)$$

where $A_{FE}$ is the fraction of the protein that remains unexchanged. Substitution of Equation (11) into Equation (14) gives an equation for FE vs. denaturant concentration:

$$FE=1-A_{FE}*e^{-t*<kint>/(1+1/Kunfold)} \quad (15)$$

where (Pace, (1986) *Method Enzymol.* 131: 266-80):

$$K_{unfold}=e^{(\Delta G0unfold-m[Denat.])/RT} \quad (16)$$

$\Delta G^0_{unfold}$ is the free energy of unfolding in the absence of denaturant, R is the gas constant and T is the temperature expressed in degrees Kelvin. Global stabilities can then be determined by fitting FE vs. [denaturant] plots to Equation (15). The m value in Equation (15) determines the sharpness of the transition in the FE vs. [denaturant] plot. Myers et al. have shown that m values can be estimated from the size of the protein (Myers et al., (1995) *Protein Sci.* 4: 2138-48). According to their analysis, B1 domain is predicted to have an m value of 1.6±0.4 kcal mol$^{-1}$ M$^{-1}$. In Equation (15), $<k_{int}>$ is the average exchange rate of unprotected amide hydrogens and is a function of pH and temperature. $<k_{int}>$ were estimated to be 30 min$^{-1}$ based on the measurements of Englander et al. (Bai et al., (1994) *Proteins* 20: 4-14). The above $k_{int}$ and m values were kept constant in the least square fitting of the data to Equation (15).

The stability of a protein in the event of single site substrate binding is described (Schellman, (1975) *Biopolymers* 14: 999-1018; Pace & McGrath, (1980) *J. Biol. Chem.* 255: 3862-65) by:

$$\Delta G^0_{unfold(bound)}=\Delta G^0_{unfold(unbound)}+RT\ln(1+S_{free}/Kd) \quad (17)$$

where $\Delta G^0_{unfold(bound)}$ and $\Delta G^0_{unfold(unbound)}$ are the folding free energies in the absence and presence of substrate, $S_{free}$ is the concentration of unbound substrate in the solution and $K_d$ is the dissociation constant for binding. Experiments can be designed such that the concentration of a test ligand (Fc fragment) is not in great excess of the test protein. Therefore, depletion of substrate can be taken into consideration (Segel, (1975) *Enzyme Kinetics*, John Wiley & Sons, New York, N.Y.):

$$S_{free}=S_{total}-\frac{E_{total}+S_{total}+K_d-\sqrt{(E_{total}+S_{total}+K_d)^2-4E_{total}S_{total}}}{2} \quad (18)$$

where $S_{total}$ and $E_{total}$ are the total concentrations of the test ligand (Fc fragment) and test protein (B1 domain), respectively. The above equations provide a relationship between FE, substrate concentration and the dissociation constant. These relationships can be employed in the quantitative study of an interaction between a test protein and a test ligand. These relationships were used to fit the binding curve in FIG. 5. Thus, the disclosed relationships can be used to fit data generated in accordance with the methods of the present invention.

VIII.A.1. Considerations in the Derivation of the Mathematical Relationships In order to derive Equation (15), several approximations have been made. In the context of the illustrative example of B1 and Fc interaction it would be expected that for the unbound B1 domain, the $\Delta G^0_{unfold}$ obtained at different exchange times would be the same. However, Table 2 indicates that the stabilities measured with 10, 90 and 180 minutes of exchange are 5, 5.6 and 5.8 kcal/mol respectively. This deviation might stem from error in the estimation that the global exchange rates among different hydrogens are the same. In reality, the global exchange rates vary according to their $k_{int}$ values. Therefore, the overall global exchange kinetics of the protein is multi-exponential. Equation (14) attempts to fit the multi-exponential exchange with a single exponential equation. The general error introduced is that at higher exchange times, the FE is over-estimated and at lower exchange times it is under-estimated. As a result, the stabilities measured by MALDI MS-HX curves at longer exchange times are generally greater than those measured at shorter exchange times. But, the closer the global exchange rates of the amide hydrogens (of the protein backbone) are together, the less this discrepancy is evident. The variation within global exchange rates is typically within one order of magnitude and the stabilities measured at varying exchange times should be within ~1 kcal/mol.

The stability of B1 domain, as measured by differential scanning calorimetry (DSC) at this temperature, is 6.1±0.5 kcal/mol. This value is slightly higher than the stabilities measured by the MALDI MS-HX methods of the present invention. There are a number of factors that can introduce discrepancies between stabilities measured by hydrogen exchange and other denaturation techniques. The most important of these is the accuracy of $k_{int}$ values. Here, for the B1 domain, the average of the $k_{int}$ values determined from the measurements of Bai et al. for model peptides (Bai et al., (1993) *Proteins* 17: 75-86) was used.

However, the potential inaccuracies introduced into $\Delta G^0_{unfold}$ measurements by hydrogen exchange do not affect the measured differences between $\Delta G^0_{unfold}$ of bound and unbound protein ($\Delta \Delta G^0_{unfold}$). The errors in the $\Delta G^0_{unfold}$ of the protein cancel each other out and differences in energy, can be measured more accurately than absolute $\Delta G^0_{unfold}$ (Li & Woodward, (1999) *Protein Sci.* 8: 1571-90). $\Delta \Delta G^0_{unfold}$ can be converted to dissociation constants as described in the Laboratory Examples. According to the data in Table 2, the dissociation constant of B1 domain is in the range of 100 nM to 1.1 µM, which corresponds to the published dissociation constant of B1 domain (300 nM). Thus, the methods of the present invention can reliably reproduce known results, thereby validating their effectiveness.

VIII.A.2. MALDI MS-HX Stability Curves Are Different From Regular Denaturation Curves It should be noted that the stability curves obtained from MALDI MS-HX analysis (such as those depicted in FIGS. 3B and 4) are not identical to conventional denaturation curves, such as those generated by circular dichroism (CD) or other methods. The midpoint of transition in conventional denaturation curves are a function of the stability and the m value of the protein. In the MALDI MS-HX curves, the midpoint is not only a function of these parameters but also depends on the time of exchange (t) and $<k_{int}>$.

$$C_{1/2}^{MS-HX} = C_{1/2}^{den} - (RT/m)ln(<k_{int}>t/0.693-1) \quad (8)$$

where $C_{1/2}^{MS-HX}$ and $C_{1/2}^{den}$ are the midpoints of transition in the MALDI MS-HX analysis and conventional denaturation curves respectively and $<k_{int}>$ is itself a function of pH and temperature (Bai et al., (1993) *Proteins* 17: 75-86). As Equation (8) demonstrates, a MALDI MS-HX curve can be shifted to the left relative to a conventional denaturation curve, since $<k_{int}>t$ is always much greater than 0.693 (the numerical value of ln2).

Referring again to the illustrative examples of MBP and $\lambda_{6-85}$ presented in the present invention, under the conditions used for the experiments described herein, this effect shifts the MALDI MS-HX curves of MBP and $\lambda_{6-85}$ by 0.5 and 2.4 M, respectively. Those of skill in the art will, therefore, recognize that the value of $C_{1/2}^{MS-HX}$ can be purposely altered by changing the pH, temperature, or exchange interval ("t"). High stabilities can be measured at higher pH and/or temperature, low stabilities at lower pH and/or temperature. Additionally, the exchange interval can conveniently range from a few minutes to hours. For example, according to Equation (8), the midpoint of the MALDI MS-HX curve for $\lambda_{6-85}$ can be shifted to the right by 1M relative to the curves shown in FIGS. 4A-4H by changing the pH to 5.9 and the exchange time to 11 minutes. This sort of adjustment makes the MALDI MS-HX methods of the present invention flexible for acquiring measurements over a wide range of stabilities.

VIII.B. Method of Qualitatively Detecting a Binding Event Involving a Test Protein and a Test Ligand The methods of the present invention facilitate a quantitative determination of binding constants and other data arising from a binding event involving a test protein and a test ligand. However, in another aspect of the present invention, a qualitative determination of the occurrence of a binding event can also be made. This ability can be helpful in a variety of situations in which a quantitative measurement is not required. For example, in the context of a high-throughput screening application, it might be desirable to simply know whether a given test ligand associates with a given test protein. Such a need can be met by the present invention. This qualitative aspect of the present invention is described more fully in the following section.

VIII.B.1. Experimental Procedure for Qualitatively Detecting a Binding Event Involving a Test Protein and a Test Ligand This application of the MALDI MS-HX method takes advantage of the fact that a binding event can have the effect of altering the stability of a protein. For example, a protein might interact with a ligand, and that interaction might stabilize or destabilize the protein's structure to a degree different than the stability of the protein in the absence of the ligand. The effect of ligand binding on the stability of the protein can be graphically represented via denaturation curves. Initially, a denaturation curve is acquired for the test protein in the absence of ligand. This curve can be generated or referred to, if it is generally available. The denaturation curve for the test protein in the absence of ligand can serve as a reference or standard curve against which an effect of a ligand binding event can be gauged.

A binding event can be qualitatively detected by employing the following generally presented method. The following steps are directed to the preparation of a denaturation curve for a test protein in the presence of ligand. A denaturation curve for the test protein in the absence of ligand can be generated prior to or subsequent to the generation of a denaturation curve of the test protein obtained in the absence of a test ligand. For data analysis denaturation curves corresponding to the test protein in the presence and absence of a test ligand should be available for comparison.

Initially, samples are prepared. Suitable preparation steps are disclosed herein and can comprise overexpressing a protein of interest in bacterial cells and lysing the cells. Steps for overexpressing a protein of interest in bacterial or other cell type and lysing of the cell are well known and described in the literature (e.g., Sambrook et al., (1992) *Molecular Cloning: A Laboratory Manual*, Cold Spring Harbor, N.Y.). If desired, the sample can be disposed on a support such as a plastic 96 well microtiter plate.

Expression of the test protein can be induced by the addition of IPTG or other compound. Cells can then be pelleted and lysed using a lysis solution, such as a BUGBUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly-high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 µL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 µL aliquot into the column, waiting five seconds, and expelling the aliquot to waste. The column can then be rinsed with a 2 µL aliquot of an ice-cold, aqueous solution comprising 5% MeOH and 0.1% TFA in order to wash away excess denaturant. Finally, the test protein can be eluted from the column and directly onto a MALDI sample stage using approximately 1 µl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of 0.001 $s^{-1}$ (FIG. 1A). Once the matrix forms a solid crystal, the exchange rate slows to a rate of 0.001 $min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots. This general MALDI MS-HX protocol can be used to generate a data set comprising the mass of the test protein as a function of denaturant concentration. These data can be plotted to generate a denaturation curve, such as those presented in FIG. 3A. If a denaturation curve for the test protein in the absence of a test ligand is not available, the same general method can be employed to generate such a curve.

Next, the denaturation data can be analyzed. Analysis can comprise evaluating the change in mass of the test protein as a function of denaturant concentration. Preferably, both of the denaturation curves for a test protein (i.e. denaturation curves for the test protein in the presence and absence of a test ligand) are plotted on the same graph. The two curves are then compared qualitatively. If the curve corresponding to the test protein in the presence of the test ligand significantly overlaps the curve corresponding to the test protein in the absence of the test ligand, it can be concluded that there is no interaction between the test ligand and the test protein.

The midpoints of the two denaturation curves can serve as convenient reference points for such a comparison. If the two curves do not significantly overlap, however, it can be concluded that there is an interaction occurring involving the test ligand and the test protein. Thus a shift in the position of a denaturation curve in the presence of a test ligand can be used to qualitatively detect a binding event involving a test ligand and a test protein.

As noted, the midpoints of the denaturation curves can themselves be analyzed. There are three broad categories of factors that determine the position of the midpoint of the MALDI MS-HX denaturation curves: First, thermodynamic parameters ($\Delta G^0_{unfold}$ and m-value), second, factors that affect the $k_{int}$ term (the exchange rate of unprotected amide hydrogens), (pH, temperature, other solution conditions, and possible exchange-protection in the denatured state) and third, exchange time, t. When comparing the curves in the absence and presence of a test ligand (such as those presented in FIGS. 3B and 6A-6D, which are discussed in detail herein) all the factors remain constant except for $\Delta G^0_{unfold}$.

An observed shift in the curves observed in the presence of substrate is due to an increase in global stability. In FIGS. 6B and 6C, for example, both curves shift to the right relative to FIG. 6A, due to an increase in the exchange times. FIG. 6D shows the curves for a variant of B1 domain that contains a E27A mutation in the binding site. The mutation had been previously shown to significantly increase the dissociation constant (Sloan & Hellinga, (1999) *Protein Sci.* 8: 1643-48). The lack of stabilization upon addition of Fc fragment supports the previous observation. Assuming that the protein unfolds in a two-state fashion, the denaturation plots in FIGS. 6A-6D can be fitted to Equation (6) to obtain the global stability. For the Illustrative example, the measured global stabilities obtained from FIGS. 6A-6D are listed in Table 2.

VIII.C. Method of Quantitatively Detecting a Binding Event Involving a Test Protein and a Test Ligand Protein G is a cell wall component of certain Staphylococcal and Streptpcoccal bacteria and can bind to the Fc portion of mammalian IgG antibodies (Frick et al., (1992) *Proc. Natl. Acad. Sci. U.S.A.* 89: 8532-36). The B1 domain used in this study is a natural variation of the IgG binding domain in Streptococcol protein G (Fahnestock et al., (1986) *J. Bacteriol.* 167: 870-80). The interaction of the B1 domain with the Fc domain of IgG has been characterized thermodynamically and structurally and serves as an effective model for the study of protein-protein energetics (Derrick & Wigley, (1992) *Nature* 359: 752-54; Derrick & Wigley, (1994) *J. Mol. Biol.* 243: 906-18; Gallagher et al., (1994) *Biochem.* 33: 4721-29; Orban et al., (1994) *Biochem.* 33: 5702-10; Sauer-Eriksson et al., (1995) *Structure* 3: 265-78; Walker et al., (1995) *Biochem. J.* 310: 177-84; Sloan & Hellinga, (1998) *Protein Eng.* 11: 819-23; Sloan & Hellinga, (1999) *Protein Sci.* 8: 16437-48). The dissociation constant for the association of the B1 domain with the Fc domain of IgG has been measured by DSC, intrinsic fluorescence and engineered fluorophores to be in the order of 300 nM (Gallagher et al., (1994) *Biochem.* 33: 4721-29; Walker et al., (1995) *Biochem. J.* 310: 177-84; Sloan & Hellinga, (1998) *Protein Eng.* 11: 819-23). In this illustrative example, B1 can be considered to be a test protein, while the Fc fragment of IgG can be considered to be a test ligand.

VIII.C.1. Experimental Procedure for Quantitatively Detecting a Binding Event Involving a Test Protein and a Test Ligand Initially, samples are prepared. Suitable preparation steps are disclosed herein and can comprise overexpressing a protein of interest in bacterial cells and lysing the cells. Steps for overexpressing a protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a test protein can be cloned into a expression vector, such as a T7 expression vector, and expressed in cells, such as *E. Coli* strain BL21-(DE3) cells. Cultures can be conveniently grown on LB or other medium. If desired, the cultures can be disposed on a support such as a plastic 96 well microtiter plate.

Expression of the test protein can be induced by the addition of IPTG or other compound. Cells can then be pelleted and lysed using a lysis solution, such as a BUGBUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 μL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 μL aliquot into the column, waiting five seconds, and expelling the aliquot to waste. The column can then be rinsed with a 2 μL aliquot of an ice-cold, aqueous solution comprising 5% MeOH and 0.1% TFA in order to wash away excess denaturant. Finally, the test protein can be eluted from the column and directly onto a MALDI sample stage using approximately 1 μl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of $0.001\ s^{-1}$ (FIG. 1A). Once the matrix forms a solid crystal, the exchange rate slows to a rate of $0.001\ min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

Figure 5:
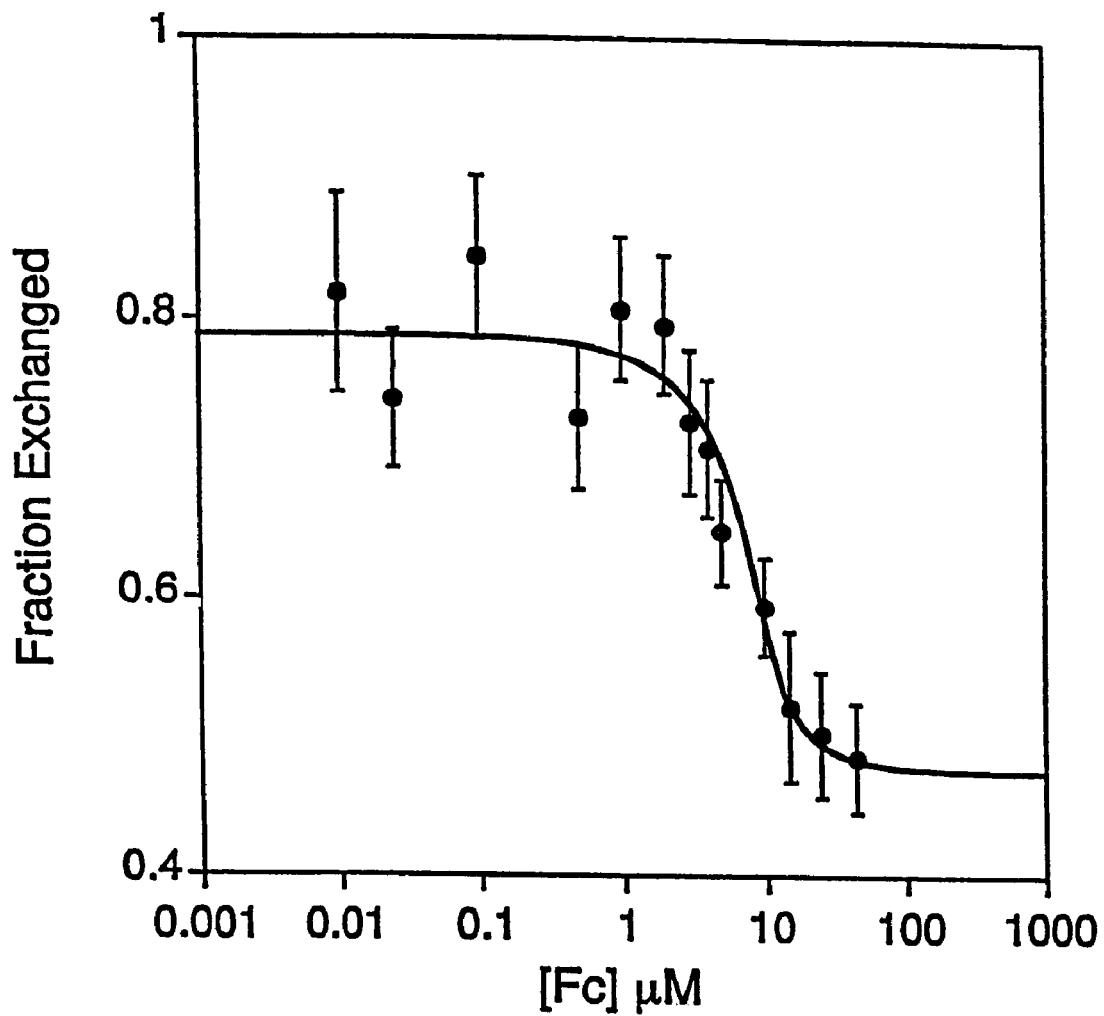
FIG. 5 is a line graph describing shows the fraction exchanged (FE) of B1 domain of streptococcal protein G (B1 domain) in the presence of 0.75 M GdmCl.

VIII.C.2. Calculation of a Dissociation Constant for a Test Protein and a Test Ligand The representative dissociation-constants presented in Table 2 were calculated by analyzing binding at a single substrate concentration. Thus, in another aspect of the present invention, affinities can similarly be measured by analyzing binding curves obtained by conducting exchange experiments as a function of substrate concentration in the presence of denaturant. FIG. 5 shows the FE of B1 domain in the presence of 0.75 M denaturant (GdmCl). As ligand (which can comprise virtually any kind of molecule) is added, the extent of exchange decreases due to protein stabilization. The dissociation constant can be determined by least square analysis of the binding curve as described herein. The measured binding constant, 500 nM, is close to the expected value, offering further-validation for results acquired by employing the present invention.

Figure 7A:
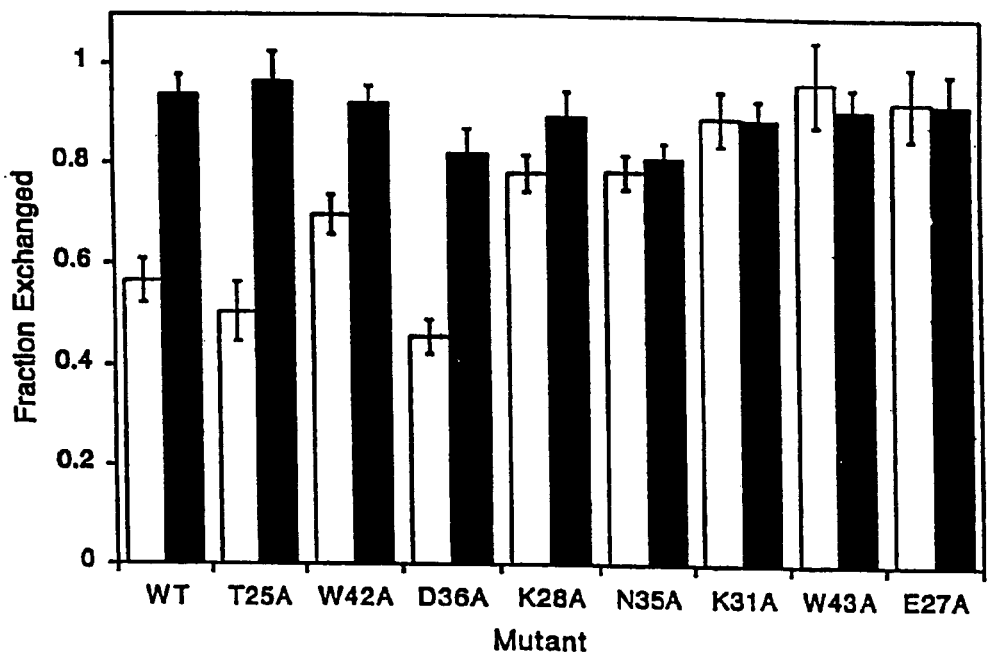
FIGS. 7A-7B are bar graphs representing the difference in FE upon addition of Fc for a number of B1 domain variants with mutations in the binding site.
Figure 7B:
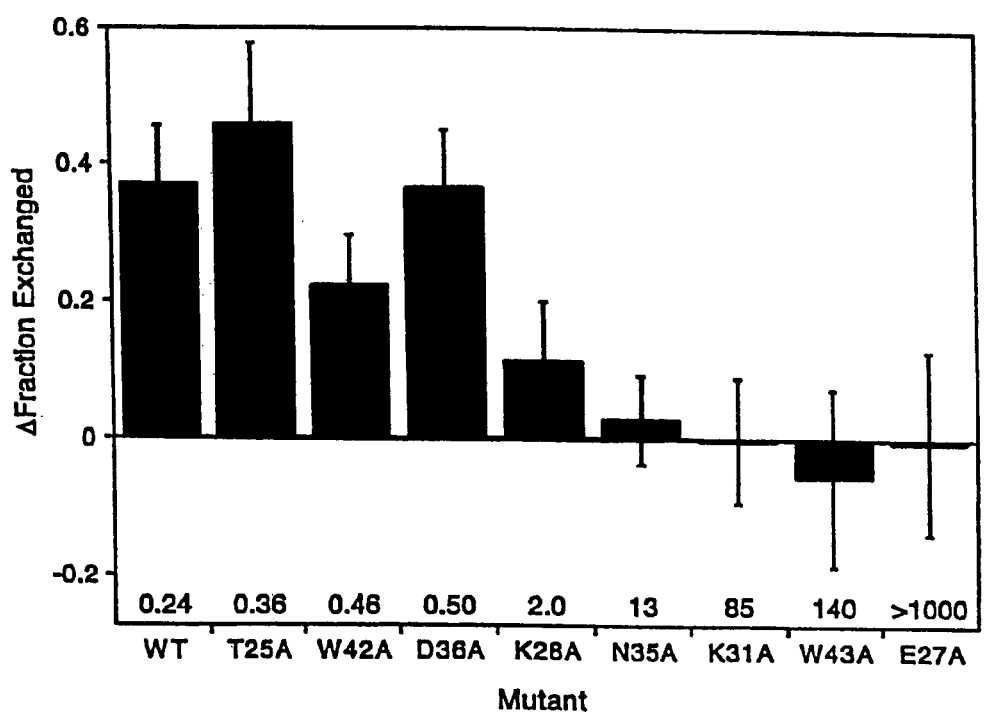

If it is desired to screen a large number of protein variants or substrates for binding without determining the dissociation constants quantitatively, it is sufficient to measure the exchange under a single set of conditions. For example, in the present invention, the exchange of a number of B1 domain variants that had mutations in the Fc binding site in the presence of 0.75 M GdmCl was measured. The exchange experiments were conducted in the absence and presence of 100 μm Fc fragment. FIG. 7A shows the comparison of the FE of the B1 domain mutants with and without the presence of Fc fragment and FIG. 7B shows the difference in FE between the two conditions. In FIG. 7A, the difference in FE upon addition of Fc for a number of B1 domain variants with mutations in the binding site is presented. The experiments were conducted at 22° C., pH 6 in the presence of 0.75 M GdmCl with an exchange time of 90 minutes. In FIG. 7A, FE in the absence is represented by open bars and presence of 10 μM Fc fragment is represented by closed bars. FIG. 7B presents the difference in FE (ΔFE) in the absence and presence of Fc fragment. The numbers represent previously published dissociation constants (Sloan & Hellinga, 1999).

Mutants that cannot bind the Fc fragment do not gain additional protection against exchange and display no change in FE. Such an experimental design can also provide information about possible stability changes caused by the mutations. If a mutation significantly destabilizes the B1 domain, the FE in the absence of Fc fragment would be altered compared to WT*. In the case of these mutations, the changes in FE in the presence of Fc are due primarily to changes in the binding energy rather than destabilization of the B1 domain. Thus, the present invention can be employed to study the effect of a mutation on protein stability.

IX. Method of Quantitatively Determining the Stability of an Unpurified Test Protein (SUPREX)

The SUPREX (Stability of Unpurified Proteins from Rates of H/D EXchange) methods, an aspect of the present invention, can be used to rapidly screen a large number of protein samples for the presence of stable structure. SUPREX refers to MALDI MS-HX methods employed in the study of unpurified protein samples. Like the MALDI MS-HX methods generally, the SUPREX methods employs hydrogen exchange coupled with matrix-assisted laser desorption/ionization (MALDI) mass spectrometry to obtain quantitative measurements of stability from crude extracts of cell cultures, which can be grown in 96 well microtiter plates. Thus, SUPREX offers all the advantages of the MALDI MS-HX methods, with the additional advantage that SUPREX does not require that a test protein sample be purified before it is analyzed.

As noted above, labile hydrogen atoms can exchange freely with the surrounding solvent. The overall structure of a protein, however, can protect a subset of these hydrogens from exchange (Hvidt & Nielson, (1996) *Adv. Protein Chem.* 21: 287-386). The stability of a protein can be analyzed by monitoring the exchange rates of these "globally protected" hydrogens (Huyghues-Despointes et al., (1999) *Nat. Struct. Biol.* 6: 910-12). Protein hydrogen exchange rates have historically been observed by techniques which allow the labile protons of a protein to exchange with $D_2O$, in an hydrogen-deuterium exchange (HX) reaction. The exchange reaction has traditionally been monitored by nuclear magnetic resonance-based techniques (Englander et al., (1996) *Curr. Opin. Struct. Biol.* 6: 18-23).

Recent studies have demonstrated that hydrogen exchange coupled with electrospray ionization (ESI) mass spectrometry can qualitatively distinguish native-like proteins from unfolded polypeptides in partially purified samples (Rosenbaum et al., (1999) *J. Am. Chem. Soc.* 121: 9509-13) and can be used to study the kinetics and thermodynamics of folding (Miranker et al., (1996) *FASEB. J.* 10: 93-101; Deng & Smith, (1999) *Anal. Biochem.* 276: 150-60). In contrast, the techniques described in the present invention employ MALDI mass spectrometry to detect hydrogen exchange. MALDI is ideally suited for fast, high throughput screening because a large number of samples can be analyzed in a short period of time. Notably, the MALDI technique is tolerant of impure samples that contain moderate levels of salts and other small molecule contaminants (Beavis & Chait, (1996) *Method Enzymol.* 270: 519-51). This feature allows the measurement of hydrogen exchange as a function of denaturant concentration to give a quantitative measurement of the protein stability.

IX.A. Sample Preparation in SUPREX Methods

The protocol for employing the SUPREX methodology is generally the same as that described above for the MALDI MS-HX methods. However, when preparing samples for a SUPREX experiment, the protein samples need not be purified. Initially, samples are prepared. Suitable preparation steps are disclosed herein and can comprise overexpressing a protein of interest in bacterial cells and lysing the cells. Steps for overexpressing a protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a test protein can be cloned into as expression vector, such as a T7 expression vector, and expressed in cells, such as *E. Coli* strain BL21-(DE3) cells. Cultures can be conveniently grown on LB or other medium. If desired, the cultures can be disposed on a support such as a plastic 96 well microtiter plate.

Expression of the test protein can be induced by the addition of IPTG or other compound. Cells can then be pelleted and lysed using a lysis solution, such as a BUGBUSTER™ solution, available from Novagen, Madison, Wis. The SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 μL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 μL aliquot into the column, waiting five seconds, and expelling the aliquot to waste. The column can then be rinsed with a 2 μL aliquot of an ice-cold, aqueous solution comprising 5% MeOH and 0.1% TFA in order to wash away excess denaturant. Finally, the test protein can be eluted from the column and directly onto a MALDI sample stage using approximately 1 μl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of $0.001\ s^{-1}$ (FIG. 1A). Once the matrix forms a solid crystal, the exchange rate slows to a rate of $0.001\text{-min}^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

IX.B. Data Acquisition in the SUPREX Methods

A difference between the SUPREX and MALDI MS-HX methods is the preparation of the sample; data can be acquired in the SUPREX methods in the same fashion as described above for the MALDI MS-HX methods. Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

IX.C. Application of the SUPREX Methods

As a demonstration that the SUPREX method of the present invention is capable of accurately measuring stability perturbations caused by mutations, SUPREX assays were performed on a series of $\lambda_{6-85}$ variants known to have different stabilities (Huang & Oas, (1995) *Proc. Natl. Acad. Sci. U.S.A.* 92: 6878-82; Burton et al., (1996) *J. Mol. Biol.* 263: 311-22; Burton et al., (1997) *Nat. Struct. Biol.* 4: 305-10). The SUPREX methods of the present invention can be employed to detect stability perturbations by employing the following general procedure. Those of skill in the art will recognize that the following procedure is presented for a given set of proteins and can be employed in the study of other proteins, mutatis mutandis.

In these experiments, hydrogen/deuterium exchange was performed at room temperature and pH 6.7 for 60 minutes. FIGS. 4A-4H depicts the generated stability curves for this set of proteins. The curves of FIGS. 4A-4H are arranged in order of the stability of the mutant, from the least to the most stable: (A) A66G; (B) A63G; (C) WT; (D) G46A/G48A/A66G; (E) G46A/G48A/A49G; (F) Q33Y; (G) G46A/G48A; (H) Q33Y/G46A/G48A. Stabilizing mutations shift the titration curves to higher GdmCl concentrations. Table 1 compares the calculated $\Delta G_f$ values obtained by SUPREX analysis of the crude samples of wild type $\lambda_{6-85}$, the G46A/G48 variant and MBP with published values obtained by conventional CD denaturation curves of the purified proteins under similar conditions. Table 1 also lists the calculated change in $\Delta G_f$ values relative to wild type proteins ($\Delta\Delta G_f$) for a series of $\lambda_{6-85}$ variants whose stabilities were determined at either 25 or 37° C. by conventional methods (Burton et al., (1997) *Nat. Struct. Biol.* 4: 305-10). Protein-dependent variations in $<k_{int}>$ values (Clarke & Fersht, (1996) *Fold Des.* 1: 243-54), and the uncertainty involved in estimating m values introduces systematic errors in the SUPREX $\Delta G_f$ estimates. However, since variants of a protein have nearly identical $<k_{int}>$ and m values, this error does not affect the $\Delta\Delta G_f$ measurements. Thus, even in the absence of exact $<k_{int}>$ and m values, the SUPREX techniques of the present invention can accurately determine the change in $\Delta G_f$. The results in Table 1 show a good correlation between the stability changes measured by CD denaturation and SUPREX.

X. Method of Quantitatively Determining Global Stability

In an aspect of the present invention, the global stability of a test protein can be quantitatively determined. When quantitatively determining the global stability of a test protein using the methods of the present invention, samples can be prepared as described above. Generally, suitable preparation steps are disclosed herein and can comprise overexpressing a protein of interest in bacterial cells and lysing the cells. Steps for overexpressing a protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a test protein can be cloned into a expression vector, such as a T7 expression vector, and expressed in cells, such as *E. Coli* strain BL21-(DE3) cells. Cultures can be conveniently grown on LB or other medium. If desired, the cultures can be disposed on a support such as a plastic 96 well microtiter plate.

Expression of the test protein can be induced by the addition of IPTG or other compound. Cells can then be pelleted and lysed using a lysis solution, such as a BUGBUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 µL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 µL aliquot into the column, waiting five seconds, and expelling the aliquot to waste. The column can then be rinsed with a 2 µL aliquot of an ice-cold, aqueous solution comprising 5% MeOH and 0.1% TFA in order to wash away excess denaturant. Finally, the test protein can be eluted from the column and directly onto a MALDI sample stage using approximately 1 µl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of 0.001 $s^{-1}$ (FIG. 1A). Once the matrix forms a solid crystal, the exchange rate slows to a rate of 0.001 $min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

As deuterium atoms replace protons during the hydrogen exchange period, the mass of the protein increases. The extent of exchange can be determined by monitoring the change in mass relative to a fully protonated sample ($\Delta_{Mass}$). The observed $\Delta_{Mass}$ is due to deuterated hydrogens that do not re-exchange in the protonated matrix. This set is restricted to the backbone amide hydrogens since they have the slowest intrinsic exchange rates among the exchangeable hydrogens.

Under native conditions, most of these observable amide hydrogens do not provide global stability information because they exchange by local (partial) unfolding processes. However, the addition of denaturant enhances the relative contribution of global unfolding to the exchange rates because local unfolding mechanisms are less denaturant dependant (Mayo & Baldwin, (1993) *Science* 262: 873-76; Bai et al., (1995) *Science* 269: 192-97). For this reason, many amide hydrogens exchange through a global unfolding mechanism at moderate denaturant concentrations below that required to significantly denature the protein.

Figure 2B:
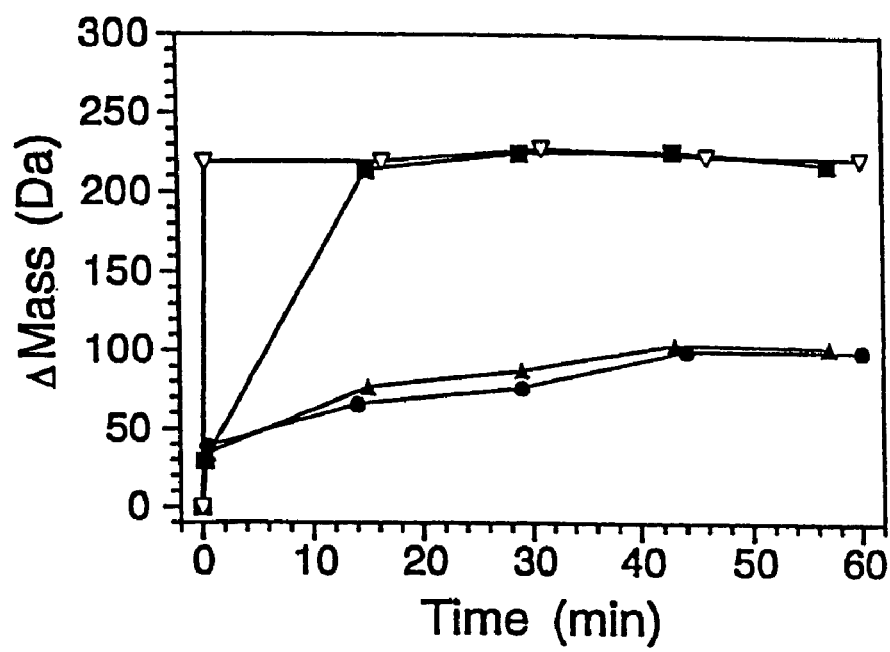
FIG. 2B is a line graph describing the change in mass of MBP as a function of exchange time in the presence of different guanidinium chloride (GdmCl) concentrations: (●)=0M; ( )=1M; (■)=2M; (▽)=6M.
Figure 3A:
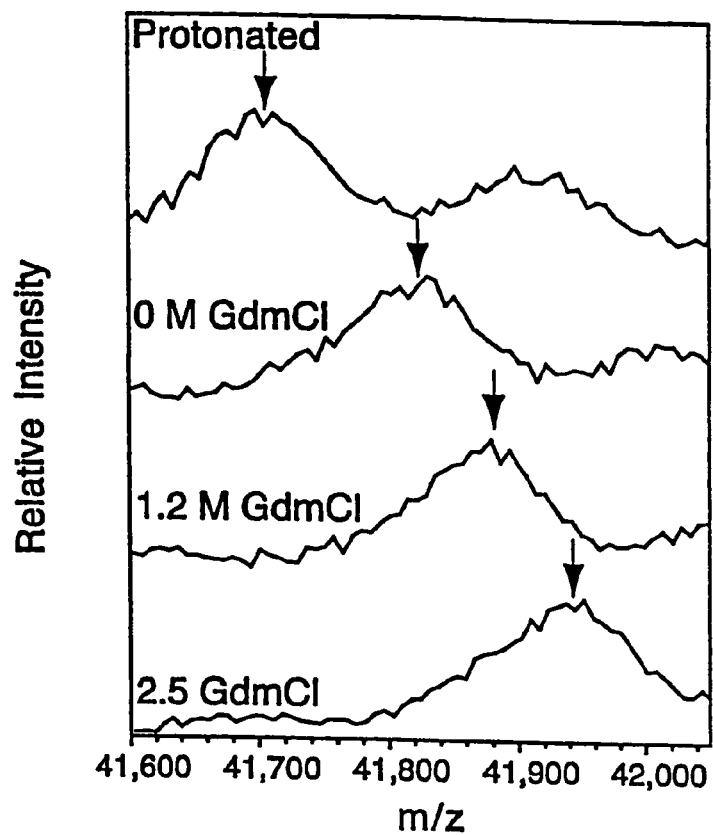
FIG. 3A is a MALDI-TOF mass spectra of MBP obtained by SUPREX and acquired after 60 minutes of exchange in the presence of different guanidinium chloride concentrations, in the absence of maltose. The spectra have been corrected with respect to the internal reference (bovine serum albumin-BSA).
Figure 3B:
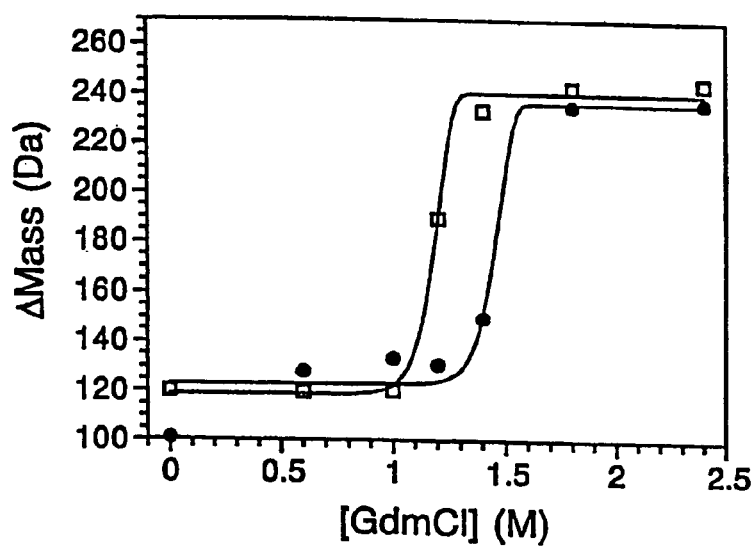
FIG. 3B is a line graph describing the change in mass of MBP as a function of guanidinium chloride concentration.
Figure 4A:
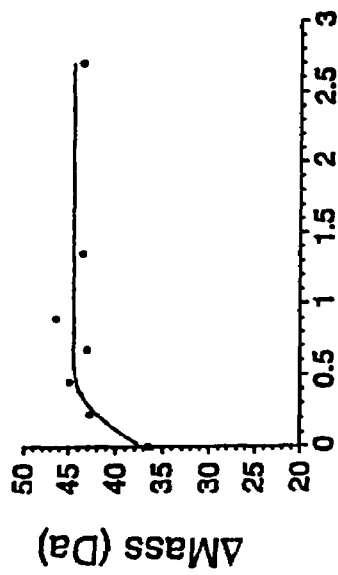
FIGS. 4A-4H are line graphs describing the stability of eight $\lambda_{6-85}$ mutants and represent data acquired by employing the SUPREX technique.
Figure 4B:
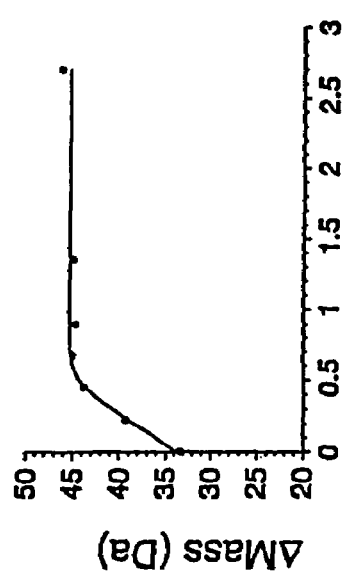
Figure 4C:
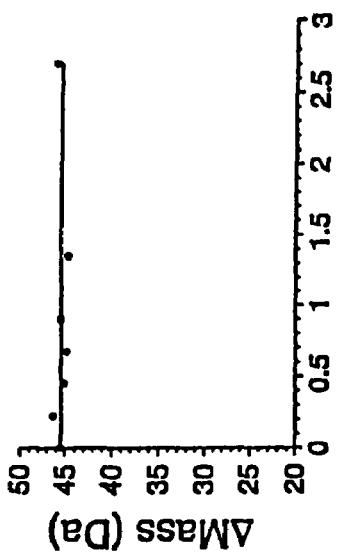
Figure 4D:
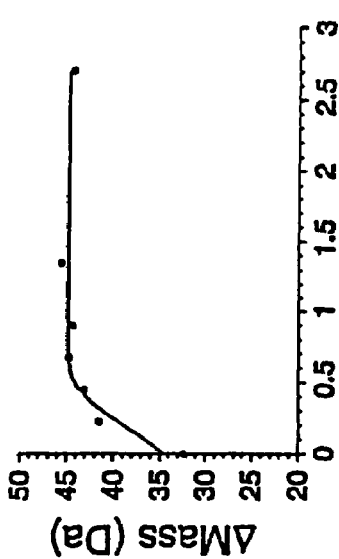
Figure 4E:
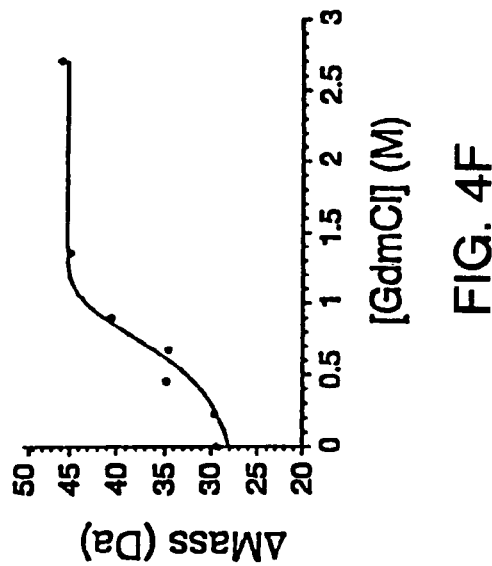
Figure 4F:
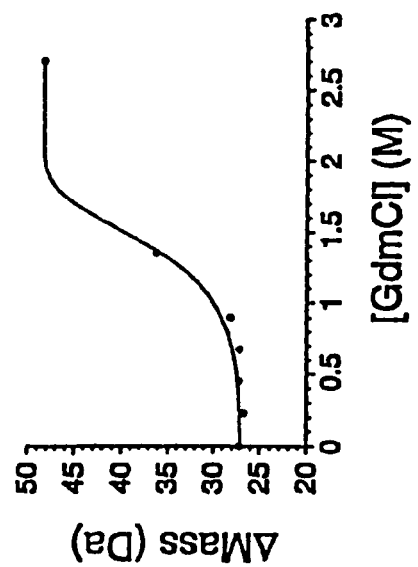
Figure 4G:
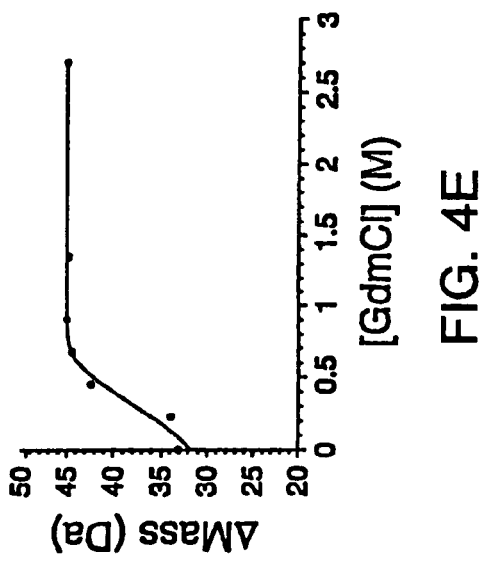
Figure 4H:
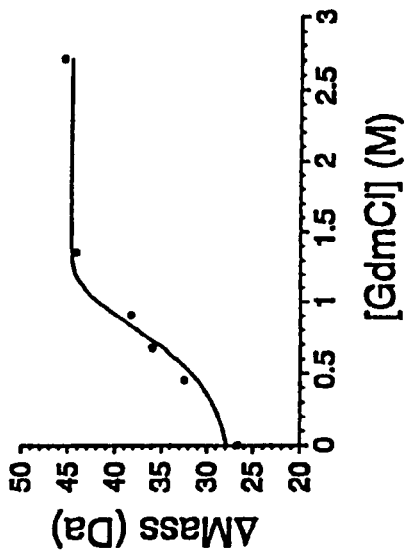

Continuing with the example involving MBP, FIG. 2B shows the exchange of maltose binding protein (MBP) as a function of time in the presence of different guanidinium chloride (GdmCl concentrations. In FIG. 2B, (●)=0M; ( )=1M; (■)=2M; (∇)=6M GdmCl. The amplitude of the 6M GdmCl curve shown in FIG. 2B represents the total number of exchangeable hydrogens observable by SUPREX for MBP. Of these ~230 hydrogens, ~100 exchange within one hour, in the absence of GdmCl. These ~100 protons are not globally protected under these conditions and exchange with deuterons relatively quickly. The remaining mass increase is due to backbone amide hydrogens that are more protected and exchange at a slower rate. The addition of GdmCl dramatically increases the exchange rate of these hydrogens through global unfolding (Mayo & Baldwin, (1993) *Science* 262: 873-76; Bai et al., (1995) *Science* 269: 192-97). FIG. 3A depicts the mass spectra (the arrow indicates the population averaged mass of the singly charged state of MBP) and FIG. 3B depicts the $\Delta_{Mass}$ of MBP after 60 minutes of exchange, as a function of GdmCl concentration in the presence and absence of 100 µM maltose. In FIG. 3B, (□) indicates no maltose present and (●) indicates the presence of 100 µM maltose. Both curves in FIG. 3B indicate the cooperative unfolding of the protein induced by the addition of GdmCl.

XI. Method of Identifying a Protein that Unfolds Through One or More Stable Intermediates As with all denaturation experiments, for the quantitative analysis of MALDI MS-HX data it is preferable that a protein under study unfolds in a cooperative, two-state process (Schellman, (1987) *Annu. Rev. Biophys. Chem.* 16: 115-37). If one or more stable intermediates are present, the data will not easily fit the MALDI MS-HX or SUPREX equations. In such cases, a multi-phasic titration curve is observed or the transition is broadened. Under these conditions, an extrapolated stability measurement is difficult. However, the midpoint of the curve still serves as a good qualitative gauge of stability. Multi-phasic or broadened MALDI MS-HX or SUPREX curves might give poor fits using predicted m values. However, this method can be employed to identify proteins that have stable folding intermediates.

Initially, samples are prepared. Suitable preparation steps are disclosed herein and can comprise overexpressing a test protein suspected of unfolding through one or more intermediates in bacterial cells and lysing the cells. Steps for overexpressing a test protein suspected of unfolding through one or more intermediates or other protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a tests protein suspected of unfolding-through one or more intermediates can be cloned into a expression vector, such as a T7 expression vector, and expressed in cells, such as E. Coli strain BL21-(DE3) cells. Cultures can be conveniently grown on LB or other medium. If desired, the cultures can be disposed on a support such as a plastic 96 well microtiter plate.

Expression of the test protein can be induced by the addition of IPTG or other compound. Cells can then be pelleted and lysed using a lysis solution, such as a BUGBUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 μL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 μL aliquot into the column, waiting five seconds, and expelling the aliquot to waste. The column can then be rinsed with a 2 μL aliquot of an ice-cold, aqueous solution comprising 5% MeOH and 0.1% TFA in order to wash away excess denaturant. Finally, the test protein can be eluted from the column and directly onto a MALDI sample stage using approximately 1 μl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of 0.001 s$^{-1}$ (FIG. 1A). Once the matrix forms a solid crystal, the exchange rate slows to a rate of 0.001 min$^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

Data analysis can comprise a qualitative evaluation of a generated unfolding curve. If the unfolding curve demonstrates multi-phasic attributes, the curve is indicative of the possible presence of stable intermediates. Methods of visual identification of multi-phasic attributes in an unfolding curve are documented will be known to those of skill in the art.

Another consideration in the quantitative analysis of MALDI MS-HX and SUPREX data is the tendency of some proteins to enter the EX1 regime at high denaturant concentrations and/or pH (Clarke & Fersht, (1996) Fold Des. 1: 243-54; Loh et al., (1996) Proc. Natl. Acad. Sci. U.S.A. 93: 1982-87; Yi et al., (1997) Fold Des. 2: 271-80). Under such conditions, the intrinsic exchange rate is greater than the folding rate and the exchange rate becomes the function of the unfolding rate rather the folding equilibrium constant. This situation can cause distortions in the MALDI MS-HX and SUPREX curves and it would be difficult to properly analyze the data without knowledge of and accounting for the denaturant dependence of the unfolding rate. In practice, as is the case with MBP and $\lambda_{6-85}$, MALDI MS-HX and SUPREX measurements will preferably be acquired at lower denaturant concentrations and pH where EX1 conditions usually do not prevail.

XII. Method of Detecting a Disease Characterized by Protein Misfolding

The methods of the present invention can be employed to detect a disease characterized by protein misfolding. Protein misfolding disorders are a common component of numerous genetic disease states including, but not limited to, cystic fibrosis, familial hypercholesterolemia, retinitis pigmentosa, Creutzfeldt-Jakob disease and a1-antitrypsin misfolding. Reduced protein stability can lead to aggregation, amyloid formation, degradation and general lack of function in vivo (McLendon & Radany, (1978) J. Biol. Chem. 253: 6335-37; Jaenicke, (1987) Prog. Biophys. Mol. Biol. 49: 117-237; Parsell & Sauer, (1989) J. Biol. Chem. 264: 7590-95; Betton & Hofnung, (1996) J. Biol. Chem. 271: 8046-52; Dobson, (1-999) Trends Biochem. Sci. 24: 329-32). There is also growing evidence that protein stabilization can also be detrimental to function (Varley & Pain, (1991) J. Mol. Biol. 220: 531-38; Shoichet et al., (1995) Proc. Natl. Acad. Sci. U.S.A. 92: 452-56). These observations suggest that thermodynamic stability is an important regulatory trait that has evolved to an optimal level to fit the functional needs of individual proteins.

In this application of the present invention, protein misfolding is identified by an alteration in stability, which can be detected as a function of a change in mass of a test protein, as compared with a reference, properly folded protein. As more and more disease states characterized by protein misfolding are identified, the present invention will find extensive applicability to identify these problems.

In the context of detecting the presence of a disease characterized by protein misfolding, a test protein will typically be a protein known to misfold, giving rise to the disease state. For example, it is known that the deletion of F508 from the cystic fibrosis transmembrane receptor (CFTR) contributes to the condition cystic fibrosis. In this case, a suitable test protein is CTFR.

In, the method of detecting a disease characterized by protein misfolding of the present invention, a test protein is first provided. Suitable preparation steps are disclosed herein and can comprise overexpressing a test protein suspected of being misfolded in bacterial cells and lysing the cells. Steps for overexpressing a test protein suspected of being misfolded or any protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a test protein can be cloned into a expression vector, such as a T7 expression vector, and expressed in cells, such as *E. Coli* strain BL21-(DE3) cells. Cultures can be conveniently grown on LB or other medium. If desired, the cultures can be disposed on a support such as a plastic 96 well microtiter plate.

Expression of the test protein can be induced by the addition of IPTG or other compound. Cells can then be pelleted and lysed using a lysis solution, such as a BUGBUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 µL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 µL aliquot into the column, waiting five seconds, and expelling the aliquot to waste. The column can then be rinsed with a 2 µL aliquot of an ice-cold, aqueous solution comprising 5% MeOH and 0.1% TFA in order to wash away excess denaturant. Finally, the test protein can be eluted from the column and directly onto a MALDI sample stage using approximately 1 µl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of 0.001 $s^{-1}$ (FIG. 1A). Once the matrix forms a solid crystal, the exchange rate slows to a rate of 0.001 $min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the test protein can then determined employing the reference protein as an internal standard.

Following incubation of the test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

The observed stability is then compared with a known stability of a properly folded test protein. To continue with the example of CFTR, a properly folded test protein could be a CFTR polypeptide wherein the F508 deletion is absent. The stability of a properly folded test protein can be measured using the MALDI MS-HX and SUP REX methods of the present invention, or, if available, the stability of a properly folded test protein can determined by examination of the appropriate literature.

Differences in the known and observed stabilities of a test protein can be indicative of the presence of a disease state. Typically, misfolded proteins can exhibit altered stabilities. If the observed and known stabilities of a test protein are very similar, it is possible that the disease state is not present in the organism that is the source of the test protein.

The SUPREX methods will be particularly useful for this application. The ability of SUPREX to tolerate impure samples makes it amenable to high throughput, automated screening. In this embodiment, SUPREX can be employed to many samples in a short period of time, potentially facilitating early diagnosis of the presence of such a disease condition.

XIII. Method of Detecting an Improperly Folded Mutant Test Protein

The MALDI MS-HX and SUPREX methods of the present invention can be employed to detect a properly folded mutant test protein. Such a detection can be based on an assessment of the stability of a mutant test protein. The methods of the present invention can facilitate a detection of the stability of an improperly (or properly) folded mutant test protein by observing a change in mass of a mutant test protein, which can be detected following H/D exchange in the mutant test protein.

It is known that a protein that is misfolded can exhibit variations in stability, compared with the properly folded form of the protein. Such misfolding can be caused by a mutation (which can be spontaneous or engineered) in the amino acid sequence of the protein. An understanding of this principle, coupled with the methods of the present invention, can therefore be used to detect properly (and improperly) folded mutant proteins. The ability to detect improperly (and properly) folded mutant proteins can be of great benefit to those researchers working the area of protein design as well as those performing basic research.

A method for detecting an improperly folded mutant protein can follow the general steps of the MALDI MS-HX and SUPREX methods. Samples can be prepared as described herein above and in the Laboratory Examples. Suitable preparation steps are disclosed herein and can comprise overexpressing a mutant test protein in bacterial cells and lysing the cells. Steps for overexpressing mutant test protein or any protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a mutant test protein can be cloned into a expression vector, such as a T7 expression vector, and expressed in cells, such as *E. Coli* strain BL21-(DE3) cells. Cultures can be conveniently grown on LB or other medium. If desired, the cultures can be disposed on a support such as a plastic 96 well microtiter plate.

Expression of the mutant test protein can be induced by the addition of IPTG or other compound. Cells can then be pelleted and lysed using a lysis solution, such as a BUG-BUSTER™ solution, available from Novagen, Madison, Wis. Lysates can then be centrifuged and the test protein isolated using protein purification methods known to those of skill in the art. Alternatively, as described further herein below, the SUPREX methods do not require a purification step. Hydrogen exchange can then be initiated.

Hydrogen exchange can be initiated by adding 10-fold excess or other desired amount of deuterated exchange buffer to the lysed cultures or the purified test protein. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 μL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 μL aliquot into the column, waiting five seconds, and expelling the aliquot to waste. The column can then be rinsed with a 2 μL aliquot of an ice-cold, aqueous solution comprising 5% MeOH and 0.1% TFA in order to wash away excess denaturant. Finally, the test protein can be eluted from the column and directly onto a MALDI sample stage using approximately 1 μl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the protein and causes a fixed number of deuterons to re-exchange with protons. Experimental data indicate that the remaining deuterons are relatively stable and re-exchange at a slower rate of 0.001 $s^{-1}$ (FIG. 1A). Once the matrix forms a solid crystal, the exchange rate slows to a rate of 0.001 $min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the mutant test protein can then determined employing the reference protein as an internal standard.

Following incubation of the mutant test protein with the matrix, an aliquot of the solution is then placed on a MALDI target and rapidly dried under an air stream. Preferably, aliquots are placed in the matrix and dried within 1 minute. For a given data point, multiple MALDI spectra can be analyzed and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of protein analyzed using the methods of the present invention. MALDI MS spectra of the sample can then be acquired, providing information regarding the mass of a mutant test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

Stability measurements can be indicative of the folding state of a protein. Thus, to detect an improperly folded mutant test protein, the observed stability of the protein can be compared with the stability of a properly folded unmutated form of the mutant test protein. That is, the observed stability can be compared with the stability of a form of the protein that is not mutated and/or is known to fold properly. The stability of a properly folded form of a mutant test protein can be determined using the methods of the present invention or can be obtained by reviewing the appropriate literature. If a comparison of the known and observed stability values indicates that the two values are significantly different, this observation lends support to the conclusion that the mutant test protein is improperly folded. Conversely, if the two values are not significantly different, this observation lends support to the conclusion that the mutant test protein is properly folded.

XIV. Method of Characterizing the Ligand Binding Profile and/or the Stability of an Uncharacterized Test Protein The time after the completion of the sequencing of the human genome has come to be known as the Proteomic Era. In this phase of post-genomic biology, biomedical research will be primarily focused on the characterization, manipulation and therapeutic development of proteins, the biomolecules for which most genes code. The ability to identify which, if any ligands a given protein associates with is an aspect of protein research. This ability is of particular interest when an unknown protein is studied, such as many of those identified, but not characterized, by the researchers of the human genome project. A critical step in the characterization of an uncharacterized protein is determining which ligands it binds, The ability to fold into a stable three dimensional structure is a crucial property of all functional proteins. Successful protein research also depends upon this fundamental property. Prior to the development of the MALDI MS-HX and SUPREX methods of the present invention, there were no feasible methods available to quantitatively determine the stability of proteins, particularly those that were impure, such as those in unpurified cell lysates, or those that could only be isolated in such small quantities. Another critical step in the characterization of an uncharacterized protein is determining its stability.

When determining the ligand binding profile of an uncharacterized protein, an uncharacterized test protein is initially prepared. Suitable preparation steps are disclosed herein and can comprise overexpressing an uncharacterized protein in bacterial cells and lysing the cells. Steps for overexpressing an uncharacterized test protein or any protein of interest in bacterial or other cell type and lysing of the cell are well known and described in the literature (e.g., Sambrook et al., (1992) *Molecular Cloning: A Laboratory Manual*, Cold Spring Harbor, N.Y.). Generally, a gene encoding a test protein can be cloned into a expression vector, such as a T7 expression vector, and expressed in cells, such as *E. Coli* strain BL21-(DE3) cells. Cultures can be conveniently grown on LB or other medium. If desired, the cultures can be disposed on a support such as a plastic 96 well microtiter plate.

Expression of the uncharacterized test protein can be induced by the addition of IPTG or other compound. Cells can then be pelleted and lysed using a lysis solution, such as a BUGBUSTER™ solution, available from Novagen, Madison, Wis. Lysates can then be centrifuged and the uncharacterized test protein isolated using protein purification methods known to those of skill in the art. Alternatively, as described further herein below, the SUPREX methods do not require a purification step. When determining the ligand binding profile of an uncharacterized test protein, a test ligand is then contacted with the uncharacterized test protein for a selected period of time, such as 30 seconds, 1, 3 or 5 minutes or other desired period of time. Hydrogen exchange can then be initiated. If the stability of an uncharacterized test protein is being determined, no test ligand need be contacted with the uncharacterized test protein.

Hydrogen exchange can be initiated by adding 10-fold excess or other desired amount of deuterated exchange buffer to the lysed cultures, purified test protein or test ligand/test protein mixture. A series of exchange buffers can be made up comprising different concentrations of a denaturant, such as guanidinium chloride (GdmCl). The lysed cultures or purified protein is then allowed to exchange for a desired period of time (e.g. 5, 10, 15, 20, 25, 30, 35, 40, 45, 50, 55, 60, 70, 80, or 120 minutes), the exchange time t.

When particularly high sensitivity is desired, protein samples can be subjected to a micro-concentration step after H/D exchange and prior to MALDI analysis. Such a micro-concentration step can involve a batch chromatography method utilizing small reverse phase chromatography columns, such as 10 μL $C_{18}$ SUPROTIPS™ available from AmiKa (Columbia, Md.). Preferably, the H/D exchange reaction is quenched with TFA (0.25% v/v) prior to binding deuterated protein samples to the columns. This quenching helps to preserve the deuteration state of the protein. Binding of a test protein to the column can be achieved by repeatedly pipetting a 2 μL aliquot into the column, waiting five seconds, and expelling the aliquot to waste. The column can then be rinsed with a 2 μL aliquot of an ice-cold, aqueous solution comprising 5% MeOH and 0.1% TFA in order to wash away excess denaturant. Finally, the test protein can be eluted from the column and directly onto a MALDI sample stage using approximately 1 μl of the ice-cold MALDI matrix solution.

When the exchange period has elapsed, an aliquot of the exchange reaction is added to a volume of a solution comprising a MALDI matrix compound (the matrix solution). A preferred matrix compound in the present invention is sinapinic acid. Although the composition of a matrix solution can vary with the matrix compound itself, a matrix solution for sinapinic acid can comprise a saturated solution of sinapinic acid in 45% acetonitrile, 0.1% trifluoroacetic acid (pH 3.0), which is preferably kept on ice (2° C.) prior to the addition of the protein. The addition of the deuterated sample to the matrix solution unfolds the uncharacterized test protein and causes a fixed number of deuterons to re-exchange with protons. Experimental data indicate that the remaining deuterons are relatively stable and re-exchange at a slower rate of 0.001 $s^{-1}$ (FIG. 1A). Once the matrix forms a solid crystal, the exchange rate slows to a rate of 0.001 $min^{-1}$ (FIG. 1B). By rapidly drying the sample on a MALDI target, the slowly exchanging deuterons are trapped in the time frame of the experiment and their number can be determined from a mass spectrum (FIG. 2A).

A reference protein can also be added to the matrix solution, when highly accurate mass measurements are desired. Suitable reference proteins can be bovine serum albumin (BSA), lysozyme or a biosynthetic nonnatural polypeptide. The mass of the uncharacterized test protein can then determined employing the reference protein as an internal standard.

Following incubation of the uncharacterized test protein (or test ligand/test protein mixture) with the matrix, an aliquot of the solution is then placed on a MALDI target and rapidly dried under an air stream. Preferably, aliquots are placed in the matrix and dried within 1 minute. For a given data point, multiple MALDI spectra can be analyzed (e.g. 1, 3, 5, 10 or any other desired number of spectra) and the results averaged. Protein concentrations in each spot can range between 0.1 and 1 pmol of protein, however as mass spectrometry technology improves, smaller concentrations, such as attomole amounts of sample can be analyzed. Thus, there is effectively no limit on the amount of uncharacterized test protein analyzed using the methods of the present invention. MALDI MS spectra of the sample can then be acquired, providing information regarding the mass of a test protein. Mass spectra can be collected on any mass spectrometer, (the VOYAGER® Biospectrometry Workstation, available from PerSeptive Biosystems Inc. of Framingham, Mass. is a preferred mass spectrometer). Spectra can be acquired in positive ion mode and summed over 32 (or other desired number) laser shots.

The results with MBP show that SUPREX can detect binding through a change in protein stability. The thermodynamic linkage between stability and binding has been established (Schellman, (1975) *Biopolymers* 14: 999-1018; Pace & McGrath, (1980) *J Biol Chem* 255, 3862-5). A large number of potential ligands can be rapidly screened for this effect. These ligands could be small molecules, proteins or nucleic acids. The SUPREX techniques of the present invention provide a convenient alternative in experiments where a binding assay is not available or difficult to employ. This approach can be applied to a method analogous to the yeast two-hybrid screen (Fields & Song, (1989) *Nature* 340: 245-46), in which two proteins of interest (e.g., a target and a library) are co-expressed and the target protein is screened for stability by the SUPREX techniques of the present invention. The methods of the present invention can also be modified to allow screening of large ligand libraries directly on MALDI plates with pre-deposited protein. The method can also be modified to allow screening of ligand bound to a solid support for protein binding.

Using the above general method, the ligand binding profile and/or stability of an uncharacterized test protein can be determined. An advantage of the present inventive methods is that no prior knowledge of an uncharacterized test protein is required. Indeed, a goal of the present invention is to provide such information to researchers. Additionally, the present invention can be employed on unpurified samples, making it particularly suited for automation and high throughput screening.

XV. Advantages of the Method of the Present Invention

As noted herein above, the methods of the present invention can be employed to quantitatively measure binding constants. The methods of the present invention offer a range of advantages over prior art methods. Representative, non-limiting advantages of the present invention over prior art methods for the measurement of binding constants are disclosed herein below.

XV.A. The Presence of a Denaturant Does Not Independently Affect the Binding Interaction One concern regarding the measurement of protein-protein binding constants with denaturation experiments is that the addition of denaturant can independently alter the dissociation constant. For example, the denaturant could unfold the substrate protein and thus nullify the interaction. Even if the denaturant does not unfold the substrate, it could interfere with binding by forming non-specific interactions with the binding site. An advantage of the present invention compared to other denaturation techniques is that stability can be measured without resorting to high enough denaturant concentrations to unfold the protein. Although the plots in FIGS. 6A-6D show a sigmoidal transition, this does not correspond to the full unfolding of the protein as in typical denaturation experiments. As indicated by its stability and m value, B1 domain remains primarily folded in 3 M GdmCl. The Fc fragment, a much larger protein, is also likely to stay primarily folded in up to 3 M GdmCl. The data in Table 2 supports this conclusion. At shorter exchange times, the transition in the MALDI MS-HX curves occurs at higher denaturant concentrations. If the presence of GdmCl was strongly affecting the binding constant it would be expected that at shorter exchange times the binding-induced $\Delta\Delta G^0_{unfold}$ would be lower. The fact that this phenomenon is not observed supports the conclusion that the presence of GdmCl does not independently affect the binding interaction and describes an advantage of the present invention over prior art methodology.

XV.B. The Methods of the Present Invention Can Distinguish Between Stability and Interaction Energy The ability of the techniques of the present invention to distinguish between the two factors that can affect the observed binding (stability and interaction energy) is an asset. The binding affinities of the B1 mutants have been measured by fluorescence (Sloan & Hellinga, (1999) *Protein Sci.* 8: 1643-48) and are presented in FIG. 7A. It can be seen that these mutants that have a dissociation of less than 10 µM do not display a significant ΔFE under these set of conditions. In this aspect of the present invention, increasing the substrate concentration will lower the binding detection threshold. Since the addition of excess amounts of substrate typically will not interfere with mass analysis of the protein, very small binding constants can be measured.

In the experimental setup described above, GdmCl was employed in order to make the exchange rate through the global mechanism more rapid. However, the inclusion of GdmCl might affect the binding constant of some protein systems. In such cases, the techniques of the present invention can be employed in combination with increasing the pH, temperature and exchange time, which will allow the data to be acquired at lower denaturant concentrations and permit distinguishing between these stability and interaction energy. The ability to distinguish between stability and interaction energy by varying these experimental parameters offer an advantage over prior art systems, because such systems do not offer this capability.

XV.C. The Methods of the Present Invention Can be Performed on Crude Samples The methods of the present invention do not require that a protein of interest be purified, because MALDI can tolerate the excess presence of most impurities. In the experiments presented in Laboratory Example 2, for example, recombinant B1 domain was expressed in *E. coli* and was analyzed without any purification. This advantage of the present invention facilitates rapid binding analysis of a large number of recombinant proteins in a short period of time. The ability of the present invention to accommodate crude samples facilitates high-throughput analysis add makes the present invention ideal for large scale screening of protein binding. Additionally, the fact that the presence of other components can be readily tolerated also makes it possible to analyze binding in complex environments. For example, dissociation constants can be analyzed in cell extracts where the effects of tertiary components on binding are of interest.

XV.D. The Methods of the Present Invention Can Measure a Wide Range of Dissociation Constants Another advantage of the methods of the present invention is that the invention makes it possible to measure exceedingly high or low dissociation constants. Very high dissociation constants can be measured because, as stated above, the change in FE can be measured in conditions where the substrate protein is in vast excess of the detected protein. This typically would not be possible if binding-induced stability changes were being detected by prior art spectroscopic techniques, such as fluorescence or circular dichroism. Very low dissociation constants can be measured because the concentration of the detected protein can be much higher than the dissociation constant. In typical titration methods, such as Scatchard analysis, the concentration of the detected protein must be similar or less than the dissociation constant (Segel, (1975) *Enzyme Kinetics*, John Wiley & Sons, New York, N.Y.). For very tight dissociation constants, the detection of the protein often becomes a limiting factor. However, when binding is being detected through stability changes using techniques of the present invention, the protein concentration can far exceed the dissociation constant. Thus, very tight binding can be analyzed without resorting to supersensitive detection methods. For example, in the experiments of Laboratory Example 2, nanomolar dissociation constants were measured, even though the concentration of B1 domain (the subject protein in this illustrative example) was in the micromolar range.

XV.E. The Methods of the Present Invention Do Not Require Derivatization or Prior Knowledge of a Test Protein The methods of the present invention are a very simple, general and economical approach to analyzing binding and stability. In fact, no prior knowledge of the structure or function of the protein is necessary. The method is applicable for small molecule and macromolecular binding and can be used to analyze the binding of ligands to proteins (e.g. maltose to maltose binding protein), small molecule inhibitors to feline immunodeficiency virus (FIV) protease, DNA to arc repressor and other protein-ligand sets.

Additionally, no derivatization of a test protein is required. It is known that derivatization of a protein sample can alter its behavior and can generate misleading experimental results. This problem is obviated by the present inventive methods because no derivatization of a test protein is required. In fact, using the SUPREX methods of the present invention, a test protein can be studied in vivo, thus further limiting misleading experimental results.

As disclosed herein, an application of the present invention is in the characterization of newly identified and/or uncharacterized proteins. As these proteins are uncharacterized, no knowledge of the protein's stability or binding profile is known. The ability to study uncharacterized proteins without derivatization is an advantage over prior art methods.

XV.F. The Present Inventive Methods Require Small Quantities of Sample

A disadvantage of conventional methods of measuring the thermodynamic stability of a protein is that these methods require relatively large amounts of pure protein. This limits the thermodynamic analysis of proteins to those that can be purified in large quantities. NMR- and calorimetry-based approaches typically require millimolar sample concentrations and milliliter sample volumes. Spectroscopy-based approaches that rely on optical techniques such as fluorescence or circular dichroism (CD) spectroscopy generally require the least amount of sample to obtain a protein stability measurement, however, even these spectroscopy-based approaches can require micromolar sample concentrations and milliliter sample volumes. Unlike NMR and other techniques, the present invention is effective with very small amounts of sample. Additionally, very small quantities of protein can be analyzed without manipulation, such as labeling reactions (See Laboratory Example 4).

Thus, the present invention discloses sensitive methods to quantitate the thermodynamic stability of a protein. The methods involve the use of H/D exchange methods, MALDI mass spectrometry, and optionally, a reversed-phase chromatography microconcentration step; therefore, it is generally applicable to proteins that are amenable to reversed-phase chromatography and mass spectral analysis by MALDI. Significantly, the protocol reduces the amount of material required for measuring a protein's thermodynamic stability to the amount of material required to prepare a desired number of MALDI samples. Using standard MALDI sample preparation techniques and commercially available instrumentation this amount of material can be picomole amounts or, as mass spectrometry technology develops, attomole amounts. Several orders of magnitude less material is employed in the present inventive method than is required by conventional techniques that are currently used to measure a protein's thermodynamic stability.

The use of more highly optimized MALDI sample preparation protocols could potentially further lower the amount of material required by the techniques of the present invention. For example, using pre-structured MALDI sample supports, it has recently been shown that it is possible to acquire MALDI mass spectra of proteins using as little as 100 amol of material (Schuerendberg et al., (2000) *Anal. Chem.* 72: 3436-442).

XV.G. The Present Inventive Method Can be Automated

Although the data disclosed in the present invention was obtained by manual methods, the entire methodology of SUPREX can be easily automated and implemented for the analysis of a very large number of samples. For the experiments described in Laboratory Example 1 and herein above, the *E. coli* cultures were grown and induced on 96 well plates. The exchange reaction and dilution into the matrix were also conducted in microtiter plates. The spotting of a sample onto a MALDI target from a microtiter well can also be done robotically and commercially available MALDI instruments can record the mass spectra of all the samples in quick succession. The analysis of the data can also be easily automated, in one aspect, by employing a computer program to analyze generated data. It is likely that a single person, with access to a MALDI instrument, could use the automated SUPREX techniques of the present invention to measure the stability of as many as 1000 proteins per day.

Those of skill in the art will recognize that MBP and $\lambda_{6-85}$, two exemplary proteins described in the present disclosure, are both fairly soluble proteins with high expression levels in *E. coli*, and thus very amenable to analysis. Poorly expressed proteins might be more difficult to visualize on a mass spectrum and might require an initial concentration procedure, such as a microconcentration step involving reverse phase chromatography as disclosed in the Laboratory Examples. Proteins that form aggregates in the lysate might also produce misleading results. Aggregation is likely to protect some hydrogens that are free to exchange in the monomeric soluble form thus creating artificially high observed stability. Complications might also arise if the recombinant protein requires some manipulation, such as reduction or renaturation for its folding. However, these complications can be minimized by the addition of moderate concentrations of denaturant sufficient to disaggregate or encourage proper disulfide bond formation but not high enough to unfold the protein. These are conditions under which SUPREX measurements using the present invention can be made. For this reason, the SUPREX techniques of the present invention can be useful even for proteins that are difficult to study by conventional methods.

XV.H. The Present inventive Methods Can be Employed in High-Throughput Screening Combinatorial and directed-evolution methods have proven to be promising techniques for designing proteins of novel structure and function (Kamtekar et al., (1993) *Science* 262: 1680-85; Pace & McGrath, (1980) *J. Biol. Chem.* 255: 3862-65). These methods systematically generate a large number of sequences and it is imperative to be able to detect successful de novo designs from a large background of unfolded polypeptides. The ability to rapidly screen a large number of sequences for stable folding is crucial to the success of these methods. With its ease of use and high throughput capability, the MALDI MS-HX and SUPREX methods can perform this function and provide a fast convenient way to select for stable designs. High throughput screening preferably takes advantage of the ability to automate the data acquisition and data analysis methods of the present invention.

XII.I. The Present Inventive Methods are Adaptable for Computer-Based Data Analysis An additional advantage of the methods of the present invention includes the ability to easily analyze data generated by the methods. Often, data analysis can be complex, cumbersome and time consuming. The data of the present invention, however, are amenable to analysis by a computer program, thus simplifying the data analysis process and saving a researcher time and eliminating the possibility of human error in data analysis.

When employing the methods of the present invention, a large number of mass spectra might require analysis. In an experiment, for example, it might be necessary to analyze 30 mass spectra collected from three different MALDI spots for each data point on a MALDI MS-HX or SUPREX stability curve. For a typical MALDI MS-HX curve, ten data points (300 spectra) are preferably collected.

A computer program has been developed by the present co-inventors, and has been dubbed Rapid Analysis of Mass Spectrometry Information (RAMSI). The RAMSI program facilitates the rapid analysis of a large number of spectra with a user-friendly interface. As input, the program preferably accepts MALDI data in raw text format and outputs the average, calibrated mass of each data point, plots of the data and a helpful statistical analysis. Preferably, such a program also outputs the worked-up data in a form that is easy to import into other graphing programs. The program is preferably written for MATHEMATICA version 4 (Wolfram Research) and will run on any common platform. The program can also be written in C, C+, C++, FORTRAN or other suitable programming language.

As an example, an experiment where sets of MALDI spectra were collected after exchange in deutrated buffers with varying concentrations of guanidinium hydrochloride (GdmCl) can be considered. The exchange can be conducted in the presence of 0 M, 0.25 M, 0.50 M, 0.75 M, 1.0 M, 1.50 M, 2.0 M, 3.0 M, 6.0 M GdmCl in deutrated buffers and also in protonated water. For each condition, 30 spectra can be collected, for a total of 300 spectra. Each of the 300 spectra are preferably exported as raw text in a two-column format, with the first column (x) representing m/z and the second column (y) representing the intensity. The filenames are preferably sequentially numbered. Documentation for the mass spectrometer which was used to collect the data can be consulted in order to determine the steps for exporting data in raw text.

A RAMSI program preferably excises the regions of the spectrum corresponding to the sample peak and determines the m/z corresponding to the highest point in the peak. It is also preferable that the program allows smoothing of the peaks before the highest point is determined. Preferably, the program is configured so as to permit a user to tell the program to ignore any peak that does not meet a required intensity threshold. For the above example, 300 such graphics can be stored in a MATHEMATICA notebook, when the program is written for use with MATHEMATICA. A table can be produced, which presents the worked up mass of the sample peaks. This mass can be the calibrated or uncalibrated mass of a sample peak, depending on the instructions of the user. The program can be configured such that if the sample or calibration peaks do not meet the threshold requirements set by the user, a zero is inserted in the table. Preferably, a program also produces a statistical summary of the results.

The program is preferably configured to then produce three plots. The first plot plots the masses for each data point separately. Since for each data point, the masses can be plotted in the order in which they were collected, this plot is useful for detecting possible back-exchange in the course of data collection. The second plot shows the range of the masses for each data point as a function of denaturant concentration. The third plot averages all the masses for each denaturant-concentration and subtracts the mass of the water experiment from the rest of the data points. The result is a Δmass vs [denaturant] plot. Preferably, a RAMSI program can also export generated tables for use by other programs.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Example 1

Quantitative, High-Throughput Screen For Protein Stability

1.A. Sample Preparation

The gene encoding maltose binding protein or $\lambda_{6-85}$ was cloned into a T7 expression vector and expressed in *E. Coli* strain BL21-(DE3). 200 μL LB cultures of the recombinant *E. Coli* were grown in 96 well plates and induced by the addition of 0.4 mM isopropylthio-β-D-galactosidase (IPTG). The cells were subsequently pelleted and lysed by suspension in 10 μL BUG BUSTER™ solution (Novagen, Inc., Madison, Wis.). The lysates were centrifuged and the supernatant was used for hydrogen exchange experiments without any further manipulation. SDS-PAGE indicated that the crude samples comprised ~10%-50% expressed protein in a background of cellular impurities. From the gel, the concentrations of the proteins were estimated to range between 50 to 500 μM.

1.B. Hydrogen Exchange

Hydrogen exchange was initiated by adding 10-fold excess deuterated exchange buffet (20 mM sodium phosphate, 20 mM sodium acetate, 100 mM NaCl, pH 6.3 for MBP or pH 6.7 for $\lambda_{6-85}$) to the lysed cultures. The exchange buffers contained different concentrations of guanidinium chloride (GdmCl). At a given exchange time, 0.5 μl of the exchange reaction was added to 50 μl of matrix solution. The matrix used for these experiments was sinapinic acid. It was prepared as a saturated solution in 45% acetonitrile, 0.1% trifluoroacetic acid (pH 3.0) and was kept on ice (2° C.) prior to the addition of the protein. The choice of sinapinic acid as the MALDI matrix was critical because it was more tolerant than other MALDI matrices to the GdmCl used in the described experiments. In order to obtain highly accurate mass measurements, a reference protein was added to the matrix solution. The reference proteins used were bovine serum albumin (BSA) for the MBP experiments and a 10.0 kD biosynthetic non-natural polypeptide for the $\lambda_{6-85}$ experiment. Once the sample protein was added to the matrix, 2 μl of the solution was immediately placed on a MALDI target and rapidly dried under an air stream. Typically, the samples were placed in the matrix and dried within 1 minute. For a given data point, 5 MALDI spectra were analyzed and the results were averaged. No more than 10 minutes passed between matrix formation and data collection. It is estimated that the amount of protein in each spot ranged between 0.1 and 1 pmol.

1.C. Measurement of Back-Exchange in the Protonated Matrix

Control experiments were performed to measure the rate of exchange of protons from the matrix back into deuterated protein sites, both in the matrix solution and in the solid matrix crystals. To examine the exchange in the matrix solution, fully deuterated MBP was placed in a pre-chilled (2° C.) matrix solution. At given time intervals the sample was dried on a MALDI target and processed as described below. To examine the exchange in the solid matrix, fully deuterated MBP was placed in a pre-chilled (2° C.) matrix solution and immediately dried on a MALDI target at room temperature. At given time intervals mass spectra were collected and processed.

1.D. Data Collection

Mass spectra were collected on a Voyager® Biospectrometry Workstation, available from PerSeptive Biosystems Inc. of Framingham, Mass., using the autosampler mode. All spectra were obtained in the positive ion mode and summed over 32 laser shots.

1.E. Analysis of SUPREX Data to Determine Protein Stability

According to the classical hydrogen exchange model (Hvidt & Nielson, (1966) *Adv. Protein Chem.* 21: 287-386):

$$k_{ex}=k_{open}k_{int}/(k_{open}+k_{close}+k_{int}) \quad (1)$$

where $k_{ex}$ is the observed exchange rate for each hydrogen, $k_{open}$ and $k_{close}$ are the rate constants for the conformational changes leading to exchange competent and exchange incompetent states respectively and $k_{int}$ is the exchange rate for the unprotected hydrogen. Under EX2 conditions (where $k_{close}$ (or $k_{open}$) are much greater than $k_{int}$):

$$k_{ex}=K_{open}k_{int}/(K_{open}+1) \quad (2)$$

where $K_{open}$ is the equilibrium constant between the exchange competent and exchange incompetent conformations of the protein ($k_{open}/k_{close}$). For the hydrogens that are exchanging through a global unfolding mechanism, $$K_{open}=1/K_{fold} \quad (3)$$

Substituting (3) into (2):

$$k_{ex}=k_{int}/(1+K_{fold}) \quad (4)$$

Since $k_{int}$ is similar among the majority of the backbone amide hydrogens (Bai et al., (1993) *Proteins* 17: 75-86), the total exchange of the hydrogens that exchange through global unfolding can be estimated by a single rate constant. The increase in mass due to the exchange of globally exchanging protons ($\Delta_{Mass}$) as a function of time can thus be estimated by the following first order rate equation:

$$\Delta Mass=\Delta M_\infty+(\Delta M_0-\Delta M_\infty)e^{-k_{ex}t} \quad (5)$$

$\Delta M_o$ is $\Delta$Mass before global exchange, $\Delta M$ is $\Delta$Mass after complete exchange, t is the exchange time. Substitution of equation 5-4 into equation 5-5 gives an equation for $\Delta$Mass vs. [GdmCl]:

$$\Delta Mass=\Delta M_\infty+(\Delta M_o-\Delta M_\infty)e^{-t^* <k_{int}>/(1+K_{fold})} \quad (6)$$

where (Pace, (1986) *Methods Enzymol.* 131: 266-80):

$$K_{fold}=e^{(\Delta G_f+m[GdmCl])/RT} \quad (7)$$

$\Delta G_f$ is the free-energy of folding in the absence of GdmCl, [GdmCl] is the guanidinium chloride concentration, m is $\delta\Delta G_f/\delta$[GdmCl], R is the gas constant and T is the temperature in Kelvin. The m value determines the sharpness of the transition in the $\Delta_{Mass}$ vs. [GdmCl] plot. Myers et al. have shown that m values can be estimated from the size of the protein (Myers et al., (1995) *Protein Sci.* 4: 2138-48). The average GdmCl m value per residue for the 34 proteins in Table 5-1 of Myers et al. is 26 ($\sigma$=7.2) cal mol$^{-1}$ M$^{-1}$ per residue. According to this analysis, MBP and $\lambda_{6-85}$ are predicted to have m values of 9.7±2.6 and 2.1±0.6 kcal mol$^{-1}$ M$^{-1}$. These measurements are close to the previously reported experimental m values (12±1 and 2.1±0.1 kcal mol$^{-1}$ M$^{-1}$, respectively) measured from CD denaturation curves (Ghaemmaghami et al., (1998) *Biochem.* 37: 9179-85; Sheshadri et al., (1999) *Protein Sci.* 8: 1689-95). In order to assess the error involved in using estimated m values, as would be the case in a high-throughput screen of proteins, the calculated m values were used in this analysis. In equation 5-6, $<k_{int}>$ is the average exchange rate of unprotected amide hydrogens and is a function of pH and temperature. In principle, $<k_{int}>$ can be estimated by averaging the values for all the backbone amide hydrogens using the measurements of Englander et al. (Bai et al., (1993) *Proteins* 17: 75-86). However, for the described experiments, the simple relationship $<k^{int}>=10^{pH-5}$ min$^{-1}$ as used to estimate the rate at room temperature and pH>4.

Referring now to the figures, FIGS. 1A and 1B demonstrate the effect of drying MBP, the test protein in this Laboratory Example, in an MS matrix, such as sinipanic acid, upon an H/D exchange rate. FIG. 1B demonstrates that, upon fixation in an MS matrix, H/D exchange in the test protein effectively stops, in contradistinction to the data of FIG. 1A which indicates that there is a slow exchange occurring. Once the exchanging deuterons are "trapped" in the MS matrix, a MALDI MS spectrum can be acquired, as depicted in FIG. 2A. FIGS. 1A-2B are representative of the MALDI MS-HX and SUPREX processes. For these figures, SUPREX was employed, as the samples were unpurified. FIG. 2B provides an indication of the number exchangeable hydrogens, as a function of the mass of the test protein, MBP.

Turning next to FIGS. 3A and 3B, FIG. 3A depicts the mass of the test protein when the test protein is incubated with various concentrations of denaturant. In this case, the denaturant is guanidinium hydrochloride. As the test protein unfolds thereby exposing a greater number of hydrogens, (with greater unfolding observed at higher denaturant concentrations) the mass of the test protein is seen to increase. In FIG. 3B, the mass of the test protein is plotted as a function of denaturant concentration. Data was acquired for two cases: first, the test protein was incubated in the absence of ligand (maltose, a known ligand of MBP, in the present experiments) and second, the test protein was incubated in the presence of a ligand. The observed sigmoidal curves are indicative of a cooperative unfolding process. The unfolding curve is seen to shift to higher denaturant concentrations in the presence of maltose. Fitting the data to the equations derived herein above generates quantitative stability measurements, which are presented in Table 1.

Finally, FIGS. 4A-4H show unfolding curves for a series of $\lambda_{6-85}$ variants known to have different stabilities. Stability measurements for this set of test proteins is presented in Table 1.

Laboratory Example 2

SUPREX as a Tool for Measuring Protein-Protein Binding

2.A. Mutagenesis And Protein Expression

The genes for the B1 domain (Q32C) and its mutants were constructed as previously described (Sloan & Hellinga, (1999) *Protein Sci.* 8: 1643-48) and cloned in the pKK223 expression vector (Pharmacia, Peapack, N.J.). Mutations were constructed in the Q32C (WT*) background. The plasmids were transformed into XL1-Blue *E coli* and grown in 10 mL cultures of LB media containing 100 μg/mL ampicillin. Expression was induced by the addition of 0.4 mM isopropy-lthio-β-D-galactosidase (IPTG). The cells were subsequently pelleted and lysed by suspension in 500 μL of BUG BUSTER™ solution (Novagen, Inc., Madison, Wis.). The lysates were centrifuged and the supernatant was used for hydrogen exchange experiments without any further manipulation. SDS-PAGE indicated that the crude samples consisted of ~30%-40% expressed protein in a background of cellular impurities. The exact protein concentration in the crude extracts was determined by gel densitometry using pure samples of B1 domain (Q32C), purified as previously described (Sloan & Hellinga, (1999) *Protein Sci.* 8: 1643-48), for calibration.

2.B. Binding Analysis by Hydrogen Exchange

The crude extracts of B1 domain were mixed with pure, proteolytically prepared Fc fragments of goat IgG (Jackson Immunoresearch, West Grove, Pa.) to obtain the desired concentrations of the two components. The mixture was allowed to equilibrate for one hour on ice. Hydrogen exchange was initiated by adding 10-fold excess deuterated exchange buffer (20 mM sodium phosphate, 20 mM sodium acetate, 100 mM NaCl, pH 6.0) to the mixture. The exchange buffers contained different concentrations of deuterated guanidinium chloride (GdmCl). At a given exchange time, 1 μl of the exchange reaction was added to 50 μl of matrix solution. The matrix used for these experiments was sinapinic acid. It was prepared as a saturated solution in 45% acetonitrile 0.1% trifluoroacetic acid (pH 3.0) and was kept on ice (2° C.) prior to the addition of the protein. In order to obtain accurate mass measurements, a reference protein ($\lambda_{6-85}$ (Huang & Oas, 1995)) was added to the matrix solution. Once the sample protein was added to the matrix, 2 μl of the solution was immediately placed on a MALDI target and rapidly dried under an air stream. Typically, the samples were placed in the matrix and dried within 1 minute. Mass spectra were collected on a VOYAGER® Biospectrometry Workstation from PerSeptive Biosystems, Inc., of Framingham, Mass., using the autosampler mode. All spectra were obtained in the positive ion mode and summed over 32 laser shots. For a given data point, 30 MALDI spectra were analyzed and the results were averaged. No more than 10 minutes passed between matrix formation and data collection.

2.C. Data Analysis

According to the classical hydrogen exchange model (Hvidt & Nielson, (1966) *Adv. Protein Chem.* 21: 287-386):

$$k_{ex}=k_{open}k_{int}/(k_{open}+k_{close}+k_{int}) \quad (1)$$

where $k_{ex}$ is the observed exchange rate for each hydrogen, $k_{open}$ and $k_{close}$ are the rate constants for the conformational changes leading to exchange competent and exchange incompetent states respectively and $k_{int}$ is the exchange rate for the unprotected hydrogen. Under EX2 conditions where $k_{close}$ (or $k_{open}$) are much greater than $k_{int}$:

$$k_{ex}=K_{open}k_{int}/(K_{open}+1) \quad (2)$$

where $K_{open}$ is the equilibrium constant between the exchange competent and exchange incompetent conformations of the protein ($k_{open}/k_{close}$). For the hydrogens that are exchanging through a global unfolding mechanism, $$K_{open}=K_{unfold} \quad (3)$$

Where $K_{unfold}$ is the global unfolding equilibrium constant. Substituting (3) into (2):

$$k_{ex}=K_{unfold}k_{int}/(1+K_{unfold}) \quad (4)$$

Since $k_{int}$ is similar among the majority of the backbone amide hydrogens (Bai et al., (1993) *Proteins* 17: 75-86), the total exchange of the hydrogens that exchange through global unfolding can be estimated by a single rate constant. The increase in mass due to the exchange of globally exchanging protons as a function of time can thus be estimated by the following first order rate equation:

$$\text{Mass}=M_{deut}-A*e^{-t*kex} \quad (12)$$

$M_{deut}$ is the mass of the fully deuterated protein, A is the amplitude of the mass increase, t is the exchange time. The change in mass can be normalized to obtain fraction exchanged (FE):

$$FE=(\text{Mass}-M_{prot})/(M_{deut}-M_{prot}) \quad (13)$$

Where $M_{prot}$ is the mass of the fully protonated protein. Equation (12) can be transformed to:

$$FE=1-A_{FE}*e^{-t*kex} \quad (14)$$

where $A_{FE}$ is the fraction of the protein that remains unexchanged. Substitution of Equation (4) into Equation (14) gives an equation for FE vs. denaturant concentration:

$$FE=1-A_{FE}*e^{-t*<kint>/1+1/Kunfold)} \quad (15)$$

where (Pace, (1986) *Method Enzymol.* 131: 266-80):

$$K_{unfold}=e^{(\Delta G0unfold-m[denaturant])/RT} \quad (16)$$

$\Delta G_{unfold}^0$ is the free energy of unfolding in the absence of denaturant, R is the gas constant and T is the temperature in Kelvin. The global stabilities were determined by fitting. FE vs. [denaturant] plots to Equation (15). The m value determines the sharpness of the transition in the FE vs. [denaturant] plot. Myers et al. have shown that m values can be estimated from the size of the protein (Myers et al., (1995) *Protein Sci.* 4: 2138-48). According to their analysis, B1 domain is predicted to have an m value of 1.6±0.4 kcal mol$^{-1}$ M$^{-1}$.

The stability of a protein in the event of single site substrate binding is (Schellman, (1975) *Biopolymers* 14: 999-1018; Pace & McGrath, (1980) *J. Biol. Chem.* 255: 3862-65):

$$\Delta G^0_{unfold(bound)}=\Delta G^0_{unfold(unbound)}+RT \ln(1+S_{free}/Kd) \quad (17)$$

where $\Delta G^0_{unfold(unbound)}$ and $\Delta G^0_{unfold(bound)}$ are the folding free energies in the absence and presence of substrate, $S_{free}$ is the concentration of unbound substrate in the solution and $K_d$ is the dissociation constant for binding. In some of the experiments conducted, the concentration of the substrate (Fc fragment) was not in great excess of the B1 domain. Therefore, depletion of substrate was taken into consideration (Segel, (1975) *Enzyme Kinetics*, John Wiley & Sons, New York, N.Y.):

$$S_{free} = S_{total} - \frac{E_{total} + S_{total} + K_d - \sqrt{(E_{total} + S_{total} + K_d)^2 - 4E_{total}S_{total}}}{2} \quad (18)$$

where $S_{total}$ and $E_{total}$ are the total concentrations of the Fc fragment and B1 domain respectively. Combining equations (15) to (18) provides the relationship between FE, substrate concentration and the dissociation constant and was used to fit the binding curve in FIG. 5.

FIG. 5 demonstrates that as additional ligand is added, the amount of H/D exchange decreases, due to stability imparted by ligand binding. This change in stability was detected using the MALDI MS-HX methods of the present invention. Specifically, the test protein in this experiment, the B1 domain of streptococcal protein G, is incubated with various concentrations of a ligand, the Fc fragment. It is seen that FE decreases as ligand is added, indicative of increased stability. Thus, FIG. 5 shows the FE of B1 domain in the presence of 0.75 M GdmCl. As ligand is added, the extent of exchange decreases due to protein stabilization. The dissociation constant was determined by least square analysis of the binding curve as described in the materials and methods section. The measured binding constant, 500 nM, is close to the expected value.

FIGS. 6A-6D depict the extent of H/D exchange in the B1 domain, occurring over three different time periods. These figures indicate that complete exchange occurs at 10 minutes. The sigmoidal shape of the curves again-indicates a cooperative unfolding event. Data was acquired in the presence and absence of ligand (Fc fragment).

FIG. 7A is a bar graph summarizing a comparison of the FE of a series of B1 domain mutants acquired in the presence and absence of ligand (Fc fragment). FIG. 7B summarizes the difference in FE between the two conditions. The various stability measurements acquired from the data of FIGS. 5, 6A-6D and 7 were quantitated using the equations and relationships disclosed herein.

Laboratory Example 3

SUPREX as a Tool for Measuring Protein Stabilities in Vivo

The G46A/G48A thermostable variant of monomeric lambda repressor ($\lambda_{6-85}$) (Burton et al., (1996) *J. Mol. Biol.* 263: 311-22) was over-expressed using a T7 vector in *E. coli* in $H_2O$-based media. To initiate hydrogen exchange, the bacteria were transferred to a deuterated media. Time-course studies indicated that under these conditions the $D_2O$ freely diffuses across the cell membrane and the solvent deuterons exchange with labile protons of the protein within the cytoplasm of the cell. Chloramphenicol was added to the deuterated media in order to inhibit further protein synthesis during the course of the exchange reaction, thereby preventing deuteration during synthesis. The *E. Coli* cells were then lysed and the extent of exchange determined using MALDI mass spectrometry to measure the increase in mass, as generally depicted in the schematic of FIG. 8.

3.A. Sample Preparation

Figure 8:
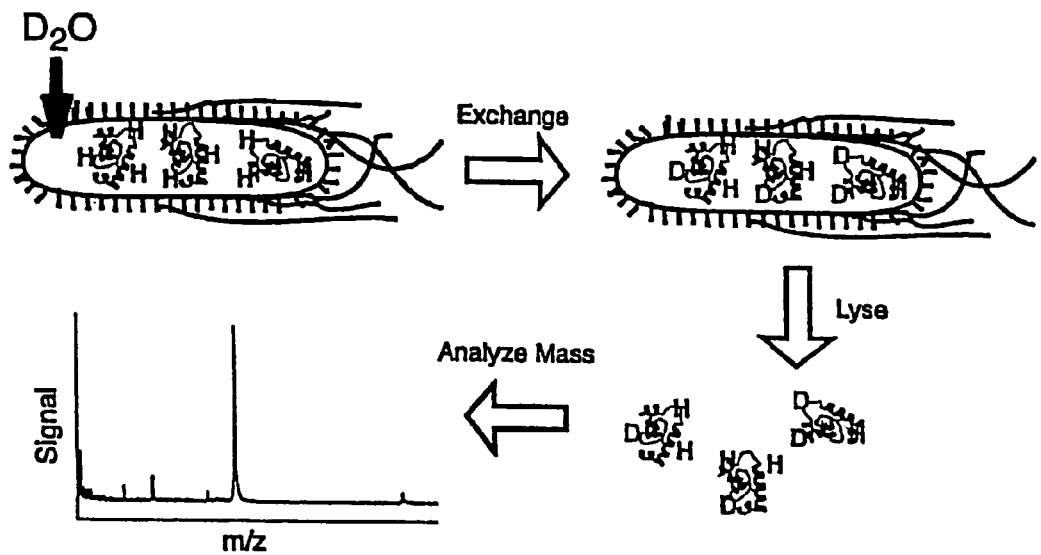
FIG. 8 is a schematic depicting the general approach to the in vivo methods of the present invention.

In vivo experiments were conducted as depicted schematically in FIG. 8. Specifically, for the in vitro experiments, 1 ml cell cultures were pelleted and lysed in 50 μl LB media containing 1× BUG BUSTER™ (Novagen, Madison, Wis.). The lysed cultures were centrifuged and 2 μl of the supernatant was mixed with 18 μl of the deuterated LB media to initiate exchange. After exchange for 20 minutes, 0.5 ml of the solution was mixed with 50 μl of the matrix solution and the MALDI was performed as described in FIG. 8. Because there was more residual $H_2O$ during the in vitro exchange reaction, the effective mass of the fully deuterated protein (determined by conducting exchange at 37° C. for 1 hr) was lower than the in vivo experiments. For the exchange experiment conducted in hyperosmotic media, the cells were grown and induced in normal LB, pelleted and resuspended in LB media containing 1.2 M NaCl. The bacteria were allowed to equilibrate for 2 hours before pelleting and resuspending in the deuterated media that also contained 1.2 M NaCl.

3.B. The Protocol for Stability Measurements in Vivo

The gene encoding the protein of interest was cloned into a T7 expression vector and transformed into *E. coli* strain BL21 (DE3). The cultures were grown in LB media and induced by 0.4 mM isopropylthio-B-D-galactosidase for 2 hours at 37° C. 100 μl volumes of the cultures were then centrifuged and the media was removed. Deuterated LB media was made by dissolving the tryptone, yeast extract and NaCl in 99% $D_2O$ (Cambride Isotopes of Andover, Mass.) and 100 μl volumes were used to resuspend the cell pellet and initiate exchange. The $D_2O$ is freely permeable across the membrane and enters the cytoplasm where H/D exchange of the protein occurs. The exchange buffer also contained 10 μg/ml chloramphenicol in order to inhibit protein synthesis during the course of the exchange reaction. The cultures were exchanged for given amounts of time and then immediately pelleted. The supernatant was removed and the cells were resuspended in 500 μL of a saturated solution of sinapinic acid in 50% acetonitrile (matrix solution) that was kept at 2° C. 2 μL of the samples were then rapidly dried on a MALDI target and the mass was analyzed using a VOYAGER® Biospectrometry Workstation from Perseptive Biosystems (Framingham, Mass.) by averaging 30 spectra in autosampler mode. A standard protein (lysozyme) was placed in the matrix solution and all the mass measurements were internally calibrated.

3.C. Time Dependence of Amide Hydrogen Exchange in Vivo

The mass of $\lambda_{6-85}$ versus H/D exchange time in vivo was determined at temperatures 15° C. (represented by open diamonds in FIG. 9), room temperature (represented by closed circles in FIG. 9), and 37° C. (represented by open squares in FIG. 9). The exchange was conducted in LB media at pH 7. The mass at time t=0 was determined by measuring the mass in an all-protonated media. The dashed line in FIG. 9C shows the effective mass of the fully exchanged protein. The left y-axis of FIG. 9 shows the measured mass and the right y-axis shows the calculated fraction exchanged.

3.D. Stability of $\lambda^*_{6-85}$ and Viability of *E. Coli* Cultures as a Function of Urea Concentration FIGS. 10A-10C depict a conventional denaturation curve by CD with purified protein in 0.15 M NaCl, 20 mM $Na_2HPO_4$, 20 mM $CH_3COONa$, pH 8. The curve represents the best fit of the data using the linear extrapolation method (Pace, 1986), yielding a stability of 6.16+−0.13 kcal/mol.

FIG. 10B shows the viability of *E. coli* when placed in various concentrations of urea for 30 minutes at 23° C. (closed circles) and 15° C. (open circles). 1 ml cultures of BL21-(DE3) *E. coli* were pelleted and resuspended in LB media containing various urea concentrations and incubated for 30 minutes at 15° C. and 23° C. The cells were then pelleted and resuspended in 1 ml of LB media, diluted 1000, plated on LB-agar plates, incubated at 37° C. overnight and the number of colonies were counted.

FIG. 10C shows SUPREX data for λ*$_{6-85}$ at 15° C. in: (●) cell lysates at pH 8; (♦) cytoplasm of viable *E. coli* cells grown in normal LB media; and (▼) SUPREX of viable *E. coli* cells equilibrated in hyperosmotic (1.2 M NaCl) LB media. The circle (●) and diamond (♦) curves represent the best fits of the data to Eq. 1 & 2, yielding stabilities of 6.7+−0.13 and 6.7+−0.2 kcal/mol in lysates and cells, respectively.

The difference in the midpoints of the SUPREX and CD curves results from the ability of SUPREX to detect small populations of denatured protein and is not indicative of a large stability change.

Laboratory Example 4

High Sensitivity Measurements of Protein Stability by H/D Exchange and Matrix-Assisted Laser Desorption/Ionization (MALDI) Mass Spectrometry 4.A. Reagents Deuterium oxide (99.9 atom % D), sodium deuteroxide, and deuterium chloride were purchased from Aldrich (St. Loius, Mo.). Deuterated phosphoric acid was obtained from Cambridge Isotope Laboratories (Andover, Mass.), and GdmCl (OMNIPUR™) was from EM Science. Bovine ubiquitin, hen egg lysozyme, and bovine pancreatic ribonuclease A (type I-A) were from Sigma (St. Louis, Mo.). Sinapinic acid (SA) was from Acros Organics. Trifluoroacetic acid (TFA) was obtained from Halocarbon (North Augusta, S.C.), and acetonitrile (MeCN) and methanol (MeOH) were from Fisher Scientific, Pittsburgh, Pa.).

4.B. General Methods and Instrumentation

MALDI mass spectra were acquired on a VOYAGER® DE Biospectrometry Workstation (PerSeptive Biosystems, Inc., Framingham Mass.) in the linear mode using a nitrogen laser (337 nm). SUPREX samples were prepared for MALDI analysis as described below. All mass spectra were collected in the positive-ion mode using an acceleration voltage of 25 kV, a grid voltage of 23 kV, a guide wire-voltage of 75 V, and a delay time of 225 ns. Each spectrum obtained was the sum of either 16 or 32 laser shots. The raw intensity versus time data in each mass spectrum was smoothed using a Savitsky-Golay smoothing routine prior to mass calibration using internal standards.

Fluorescence measurements were made on a Fluorolog-3 manufactured by Jobin Yvon-SPEX (Jobin Yvon Ltd., Middlesex, England) using a quartz cuvette (10×10 mm) and using excitation and emission slit widths of 4 and 8 mm, respectively. The excitation wavelength was set at 278 nm and the emission wavelength was scanned from 250 to 400 nm in 0.2 nm steps with a 500 ms dwell time.

RNase A protein concentrations were determined spectrophotometrically using a molar extinction coefficient of 9800 $M^{-1}$ $cm^{-1}$ at 278 nm (Sela & Anfinsen, (1957) *Biochim. Biophys. Acta* 24: 229-235); UV/V is absorbance data were collected using a Hewlett Packard 8452A Diode Array UV/V is Spectrophotometer (Hewlett-Packard, Palo Alto, Calif.). All GdmCl concentrations were determined using a Bausch & Lomb (Rochester, N.Y.) refractometer by the method of Nozaki (Nozaki, (1972) *Methods Enzymol.*, 26: 43-50). All pH measurements were recorded using a Jenco 6072 pH meter equipped with a Futura™ calomel pH electrode from Beckman Instruments (Fullerton, Calif.). Buffer pD values were determined from pH measurements by adding 0.4 to the measured pH according to Glascoe & Long (Glascoe & Long, (1959) *Anal. Chem.* 64: 188-190).

4.C. SUPREX Data Collection and Analysis

Two different experimental protocols were employed for the SUPREX analysis of RNase A including one for normal analyses and one for high sensitivity analyses. H/D exchange reactions were initiated by combining 1 µL aliquots of a 100 µM solution of RNase A (fully protonated) in 20 mM sodium phosphate buffer (pH 7.4) with 9 µL volumes of 10 different deuterated exchange buffers containing 20 mM sodium phosphate (pD=7.4) and concentrations of GdmCl that varied between 0.5 and 4 M. After a specified exchange time (typically 65 minutes), a 1 µL aliquot of each exchange reaction was combined with 19 µL of a MALDI matrix solution. The MALDI matrix solution, which comprised an ice-cold, saturated, aqueous solution of SA containing 63% MeCN and 0.1% TFA (pH=3.0), effectively quenched the H/D exchange reaction and prepared the sample for MALDI analysis. This matrix solution also included two internal mass standards, bovine ubiquitin (8566.1 Da) and hen egg lysozyme (14, 303.7 Da). Subsequently, 1 µL of the quenched exchange reaction was spotted on a stainless steel MALDI plate and the solvent was evaporated under a gentle flow of air. Solvent evaporation was typically complete within one minute.

Figure 11:
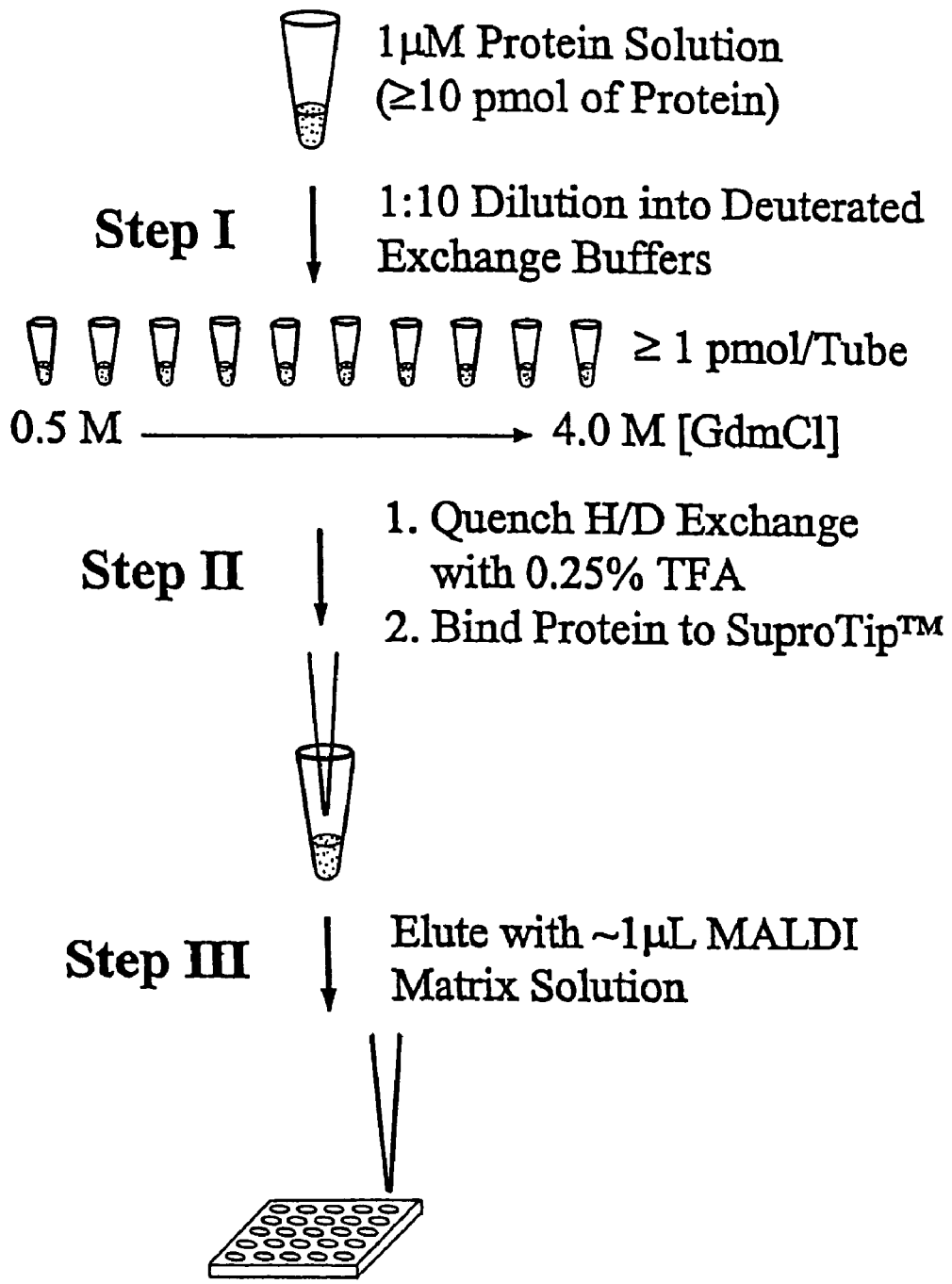
FIG. 11 is a schematic depicting an embodiment of the SUPREX methods disclosed herein below.

High sensitivity SUPREX analyses of RNase A were performed according to the experimental protocol shown in FIG. 11. The high sensitivity SUPREX protocol outlined in FIG. 11 is similar to the SUPREX protocol disclosed above, with the exception that protein samples were subjected to a micro-concentration step after H/D exchange and prior to MALDI analysis. This micro-concentration step involved the use of a batch chromatography method utilizing 10 µL $C_{18}$ SUPROTIPS™ from AmiKa (Columbia, Md.). It was preferred to quench the H/D exchange reaction with TFA (0.25% v/v) prior to binding the deuterated protein samples to the SUPROTIPS™. This facilitated preservation of the deuteration state of the protein. Binding of RNase A to the tip was achieved after five cycles of pipetting a 2 µL aliquot into the tip, waiting five seconds, and expelling the aliquot to waste. The tip was rinsed with a 2 µL aliquot of an ice-cold, aqueous solution containing 5% MeOH and 0.1% TFA in order to wash away excess GdmCl. Finally, RNase A was eluted from the reversed-phase coating in the SUPROTIPS™ and directly onto a MALDI sample stage using approximately 1 µl of the ice-cold MALDI matrix solution described above.

For both normal and high sensitivity analyses 10 replicate MALDI mass spectra were collected and analyzed to determine an average change in mass relative to the fully protonated sample (ΔMass) at each [GdmCl]. These spectra were generated by sampling different regions of a single MALDI sample preparation. Ultimately, ΔMass values were plotted as a function of [GdmCl] and the data were fit to the SUPREX equation:

$$\Delta Mass = \Delta M_\infty + (\Delta M_0 - \Delta M_\infty)e^{-(<k_{int}>/(1+K_{fold}))t} \quad (6)$$

where $$K_{fold} = e^{-(\Delta G_f + m[GdmCl]/RT)} \quad (7)$$

$\Delta M_0$ was ΔMass before global exchange, $\Delta M_\infty$ was ΔMass after complete exchange, t was the time of exchange, $<k_{int}>$ was the average intrinsic H/D exchange rate for an amide proton, $\Delta G_f$ was the free energy of folding in the absence of GdmCl, [GdmCl] was the GdmCl concentration, m was $\delta\Delta G_f/\delta[GdmCl]$, R was the gas constant, and T was the temperature in Kelvin.

Values for $\Delta M_0$, $\Delta M_\infty$ and $\Delta G_f$ were obtained by fitting the ΔMass versus [GdmCl] data to equation 1 using SigmaPlot and a nonlinear least squares analysis. $<k_{int}>$ value of 8.47 $s^{-1}$ was used, which was calculated based on the data of Bai et al., (Bai et al., (1993) *Proteins* 17: 75-86), using the program SPHERE (Zhang, *Ph.D. Thesis*, Structural Biology and Molecular Biophysics, University of Pennsylvania); and an m value of 3.1 kcal mol$^{-1}$ M$^{-1}$ was used, which was previously determined in other GdmCl-induced equilibrium unfolding experiments on RNase A (Pace et al., (1990)*Biochem.* 29: 2564-72). The quantitative analysis of the SUPREX data in this Example assumed that RNase A unfolded in a cooperative, two-state process and that the protein was under EX2 exchange conditions (i.e. the unfolding and refolding rate of the protein is faster than the intrinsic rate of H/D exchange). Previous work on the RNase A system indicates that these assumptions are valid (Pace et al., (1990) *Biochem.* 29: 2564-72; Huyghues-Despointes et al., (1999) *Nat. Struct. Biol.* 6: 910-12.)

4.D. Summary of Results

Figure 12A:
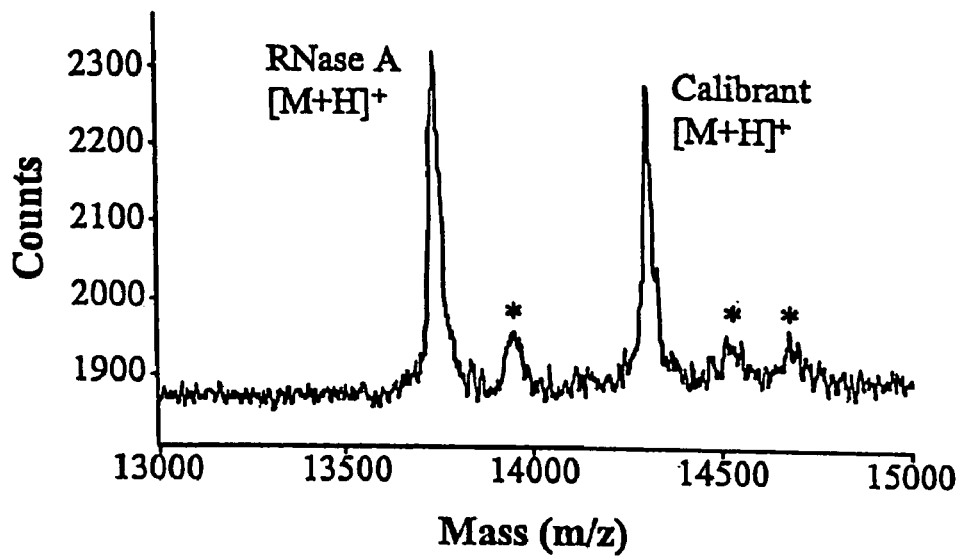
FIG. 12A is a MALDI mass spectrum acquired in one embodiment of the SUPREX method without a chromatography step, as applied to RNase A. The ion signal detected for RNase A at m/z 13,732.6 indicates a mass gain of 49.5 over the fully protonated molecule.
Figure 12B:
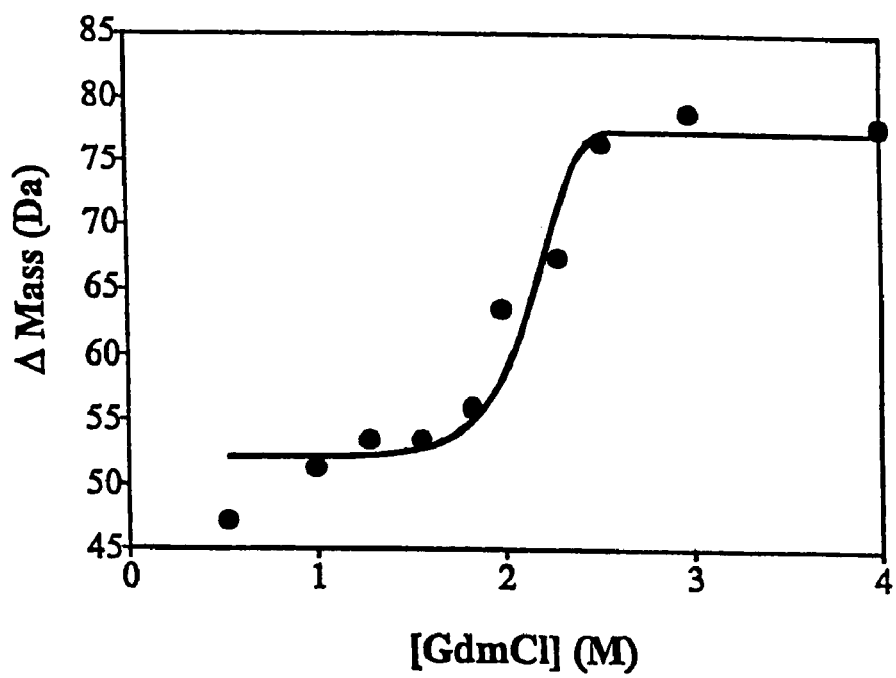
FIG. 12B is a line graph describing typical SUPREX data obtained M for RNase A using an embodiment of the SUPREX method without a chromatography step.

Typical results from the normal SUPREX analysis of RNase A are shown in FIGS. 12A and 12B. The MALDI mass spectrum in FIG. 12A is typical in quality (i.e. signal intensity and resolution) to those that were used to generate the SUPREX curve shown in FIG. 12B. Thus, FIG. 12A is a representative MALDI mass spectrum acquired in the normal SUPREX analysis of RNase A. The ion signal detected for RNase A at m/z 13,732.6 indicates a mass gain of 49.5 over the fully protonated molecule. The resolution, full width half maximum (FWHM), for the RNase A and calibrant peaks were 375 and 587, respectively. The peaks labeled with a are attributed to impurities in the sample.

The SUPREX curve in FIG. 12B yielded a $\Delta G_f$ value for RNase A of $-12.9$ kcal mol$^{-1}$ with a standard error of 0.2 kcal mol$^{-1}$. FIG. 12B is a typical SUPREX curve obtained for RNase A using a normal SUPREX protocol. The average $\Delta G_f$ value and standard deviation that was obtained from three replicate SUPREX analyses of RNase A was $-12.4\pm0.4$ kcal mol$^{-1}$. The $\Delta G_f$ value for RNase A that was determined by SUPREX is in relatively good agreement with the $\Delta G_f$ value of $-9.24\pm0.64$ kcal mol$^{-1}$ that was determined by Pace et. al. using conventional fluorescence denaturation methods (Pace et al., (1986) 131: 266-280). The difference between the two measurements is likely due to inherent difficulties with SUPREX that are associated with obtaining an accurate measure of <$k_{int}$>. The <$k_{int}$> value that was utilized in the SUPREX analysis of RNase A was based on model peptide studies (Bai et al., (1993) *Proteins* 17: 75-86).

Figure 13:
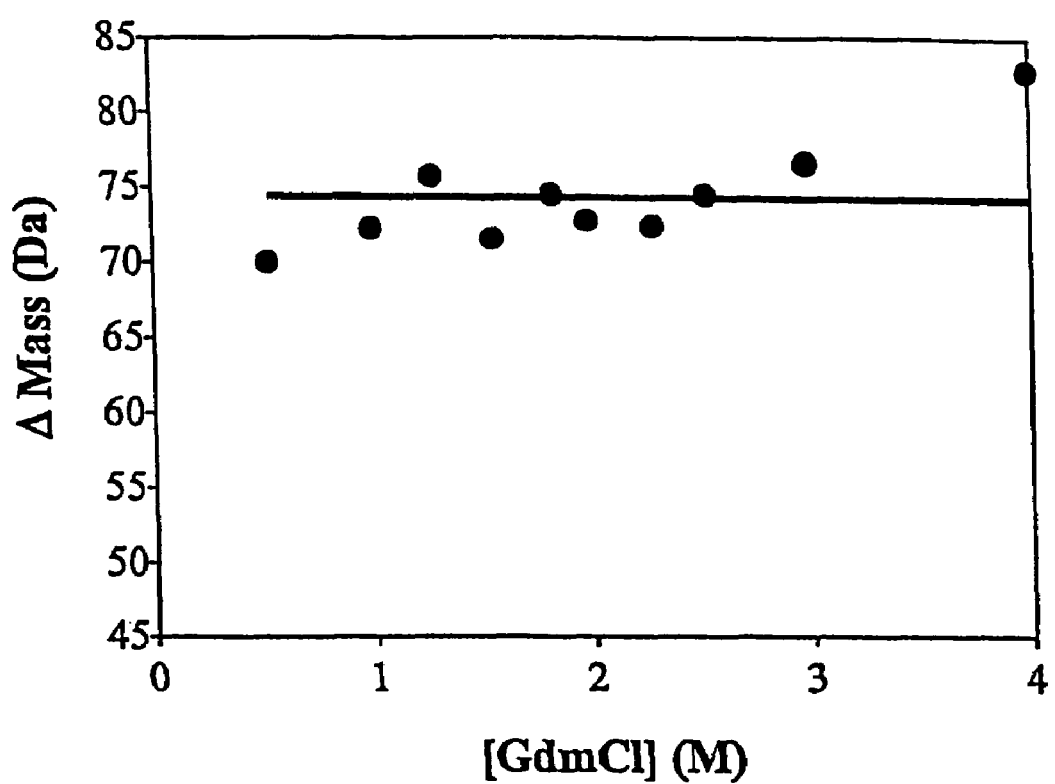
FIG. 13 is SUPREX data obtained for RNase A using a high sensitivity SUPREX protocol that did not include a step quenching the H/D exchange reactions with TFA (0.25% v/v) prior to subjecting them to a batch chromatography step for micro-concentration.

The protocol includes a batch chromatography step for the micro-concentration and desalting of protein samples after H/D exchange and prior to MALDI analysis. In the development of the protocol in FIG. 11 it was observed that it was preferable to quench the H/D exchange reactions with TFA (0.25% v/v) prior to subjecting them to a batch chromatography step using reversed-phase $C_{18}$ media. FIG. 13 represents SUPREX data obtained for RNase A using a high sensitivity SUPREX protocol that did not include a step quenching the H/D exchange reactions with TFA (0.25% v/v) prior to subjecting them to a batch chromatography step for micro-concentration.

Shown in FIG. 12B are the SUPREX data obtained on RNase A using the high sensitivity protocol outlined in FIG. 11. The MALDI mass spectrum in FIG. 12A is typical in quality (i.e. signal intensity and resolution) to those that was used to generate the SUPREX curve shown in FIG. 12B. Analysis of the SUPREX data in FIG. 12B yielded a $\Delta G_f$ value for RNase A of $-12.4$ kcal mol$^{-1}$ with a standard error of 0.2 kcal mol$^{-1}$. The average $\Delta G_f$ value and standard deviation that was obtained from 3 replicate SUPREX analyses of RNase A using the high sensitivity SUPREX protocol was $-12.0\pm0.5$ kcal mol$^{-1}$. This $\Delta G_f$ value for RNase A is in very close agreement with the $\Delta G_f$ value of $-12.4\pm0.4$ kcal mol$^{-1}$ that was determined using the normal SUPREX protocol described above.

Figure 14A:
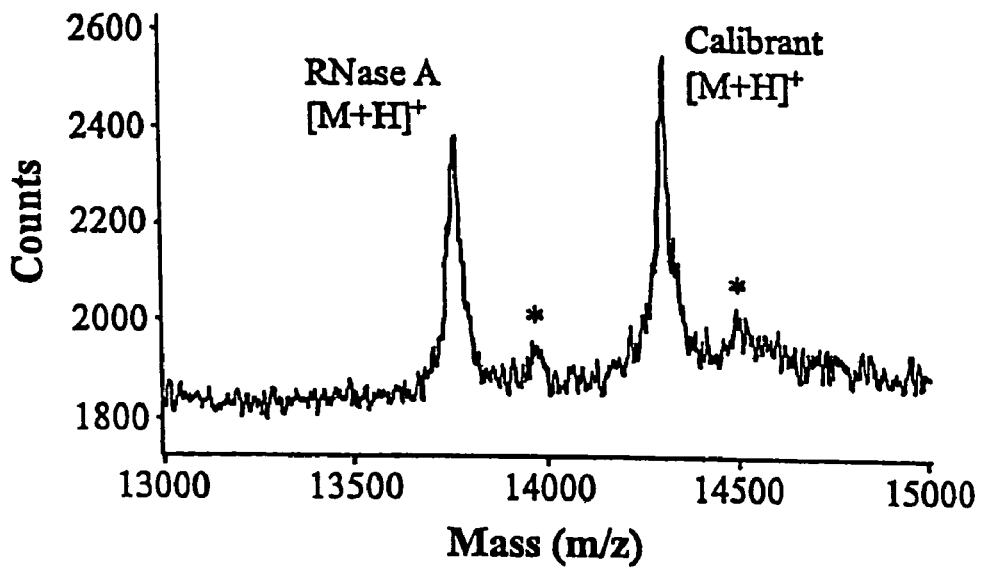
FIG. 14A is a representative MALDI mass spectrum acquired in the high sensitivity SUPREX analysis of RNase A. The ion signal detected for RNase A at m/z 13,757.2 indicates a mass gain of 74.1 Da over the fully protonated molecule.
Figure 14B:
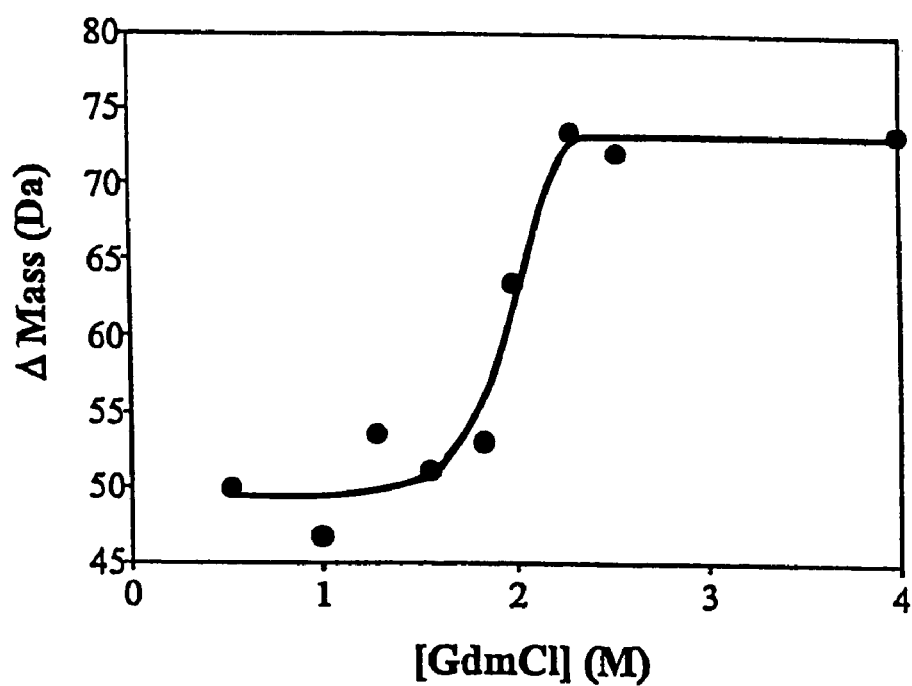
FIG. 14B is a line graph describing typical SUPREX data obtained for RNase A using the high sensitivity SUPREX protocol presented in FIG. 11.

FIG. 14A is a representative MALDI mass spectrum acquired in the high sensitivity SUPREX analysis of RNase A. The ion signal detected for RNase A at m/z 13,757.2 indicates a mass gain of 74.1 Da over the fully protonated molecule. The resolution, full width half maximum (FWHM), for the RNase A and calibrant peaks were 327 and 472, respectively. The peaks labeled with a * are attributed to impurities in the sample. In FIG. 14B, a typical SUPREX data obtained for RNase A using the high sensitivity SUPREX protocol in FIG. 11 is presented. The data in FIGS. 14A and 14B were generated using a total of 10 pmol of RNase A (i.e. 10 μl of a 1 μM solution). This amount of material is 100-fold less than that required in the normal SUPREX protocol. It is also several orders less material than that required by conventional spectroscopy-based methods. The SUPREX curve in FIG. 14B was generated using only 10 pmol of RNase A.

Laboratory Example 5

SUPREX Analysis of Multimeric Proteins

Figure 15:
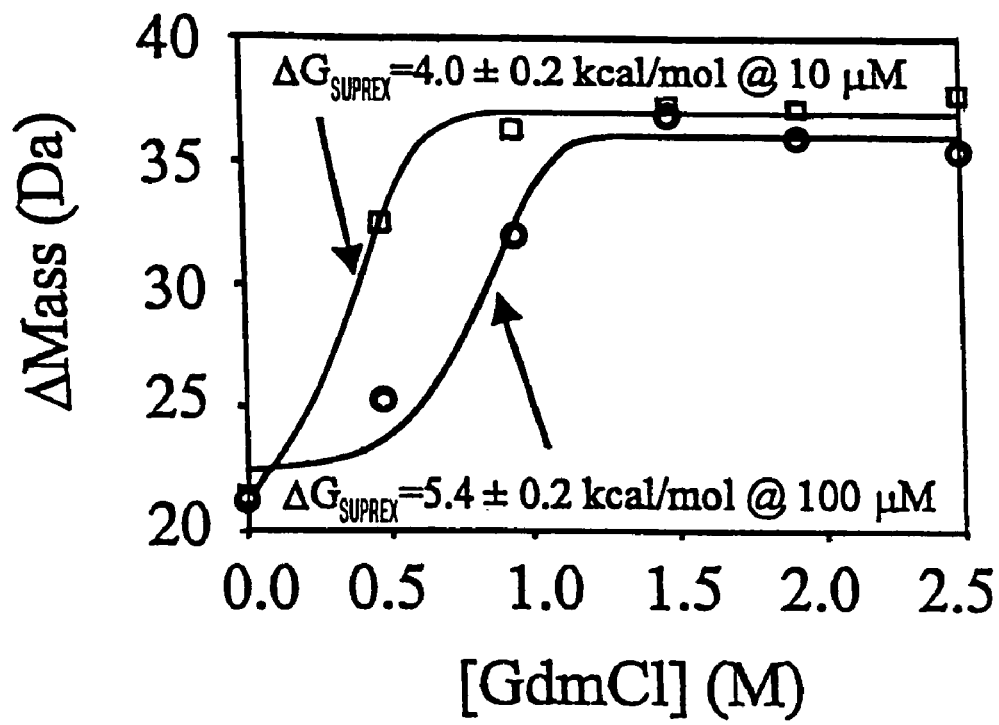
FIG. 15 is a line graph depicting the results from the SUPREX analysis of P22 Arc repressor, a homo-dimeric protein, are shown.

Referring to FIG. 15, results from the SUPREX analysis of P22 Arc repressor, a homo-dimeric protein, are shown. The line represents the best fit of the data to the SUPREX equation (i.e. Equation (6)). As expected for a multimeric protein, the measured $\Delta G$ value increased with increasing protein concentration. If the $\Delta G_{SUPREX}$ values recorded at each protein concentration are adjusted to standard conditions (1 M dimer) then the data at each protein concentration yields a standard $\Delta G$ value of $11.3\pm0.2$ kcal/mol which is consistant with the previously reported value of 11.0 kcal/mol that was obtained in conventional CD denaturation studies (Bowie et al., (1989) *Biochemistry* 28: 7139-7143).

Laboratory Example 6

Figure 16:
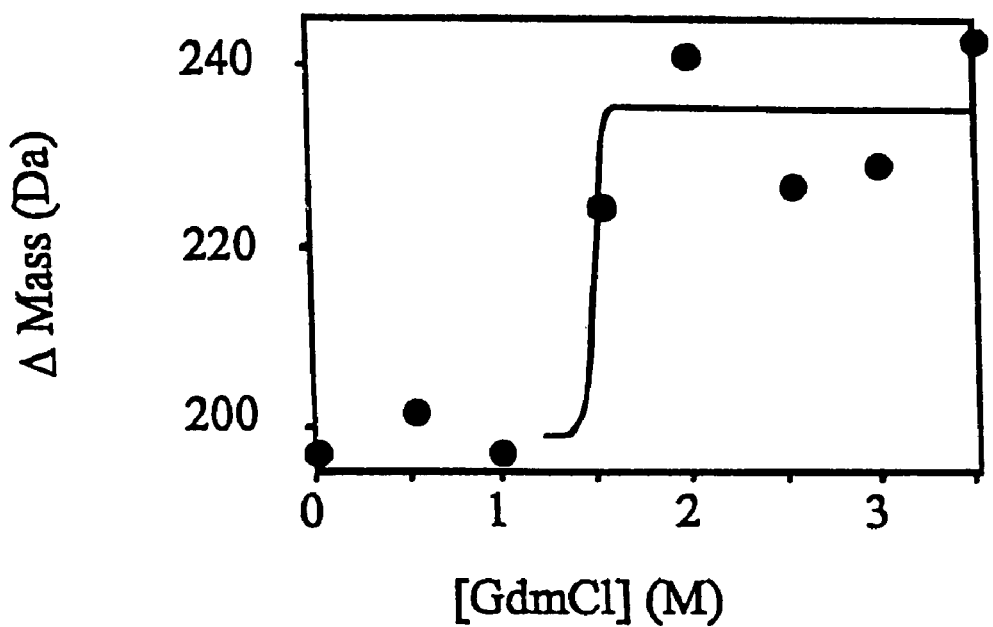
FIG. 16 is a line graph depicting results from the SUPREX analysis of bovine serum albumin, a high molecular weight protein.

FIG. 16 depicts the results of a SUPREX analysis of bovine serum albumin, a high molecular weight protein. The line represents the best fit of the data to the SUPREX equation (i.e. Equation(6)) when m=15 kcal/mol M and $k_{int}$=52.7 sec$^{-1}$.

Laboratory Example 7

Figure 17A:
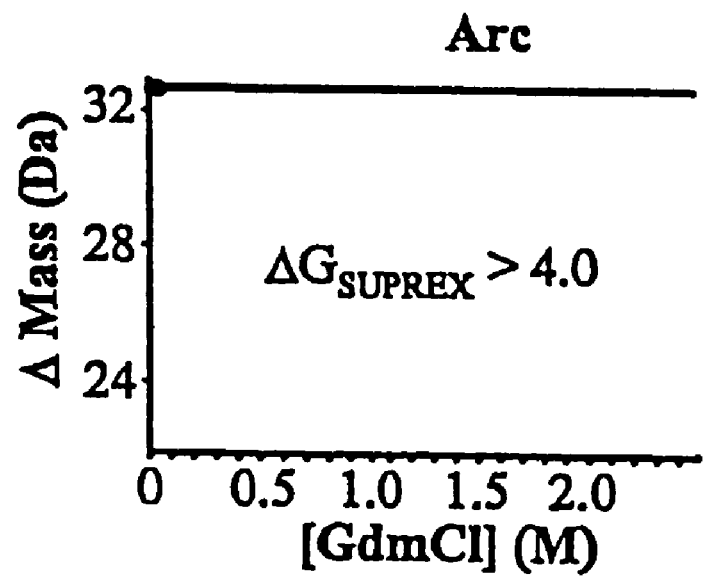
FIG. 17A is a line graph depicting the results from a SUPREX analysis of P22 Arc repressor in the absence of cognate DNA.
Figure 17B:
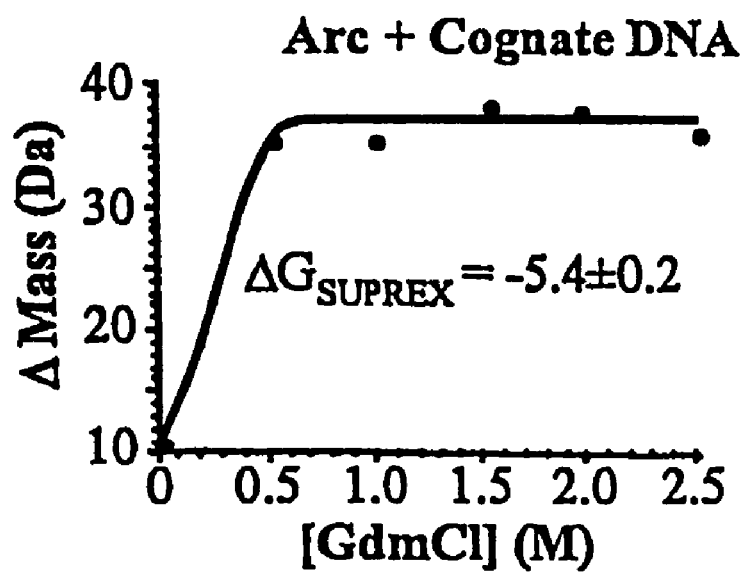
FIG. 17B is a line graph depicting the results from a SUPREX analysis of P22 Arc repressor in the presence of cognate DNA.

FIGS. 17A and 17B depict the results of a SUPREX analysis of P22 Arc repressor in the absence (FIG. 17A) and the presence (FIG. 17B) of cognate DNA. The data was generated using an Arc dimer concentration of 12 μM in deuterated exchange buffers containing 20 mM phosphate (pH=7.4) and varying concentrations of GdmCl. At this concentration the stability of the Arc dimer is less than that detectable by SUPREX. Even with exchange times of several minutes, there is no transition detected in the SUPREX curve. The transition midpoint is shifted off scale to the left; and only a maximum $\Delta G_{SUPREX}$ value (<4.0 kcal/mol) can be calculated. The addition of Arc repressor's cognate DNA (a double stranded 27mer of sequence ATC GAT GAT AGA AGC ACT CTA CTA TCG (SEQ ID NO: 1) to the exchange buffer significantly stabilized the Arc dimer to the point that the its stability could be measured by SUPREX. The addition of 6.3 μM DNA to the exchange buffer resulted in an apparent stabilization, $\Delta G_{Binding}$, of at least 1.4 kcal/mol.

Laboratory Example 8

Figure 18A:
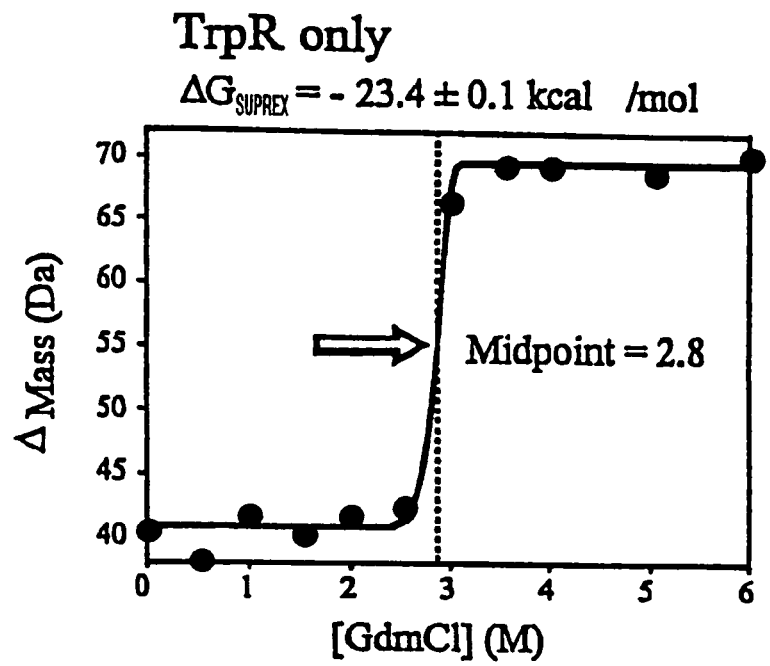
FIG. 18A is a line graph depicting the results' from a SUPREX analysis of the Trp repressor protein in the absence of a tight binding ligand, L-tryptophan.
Figure 18B:
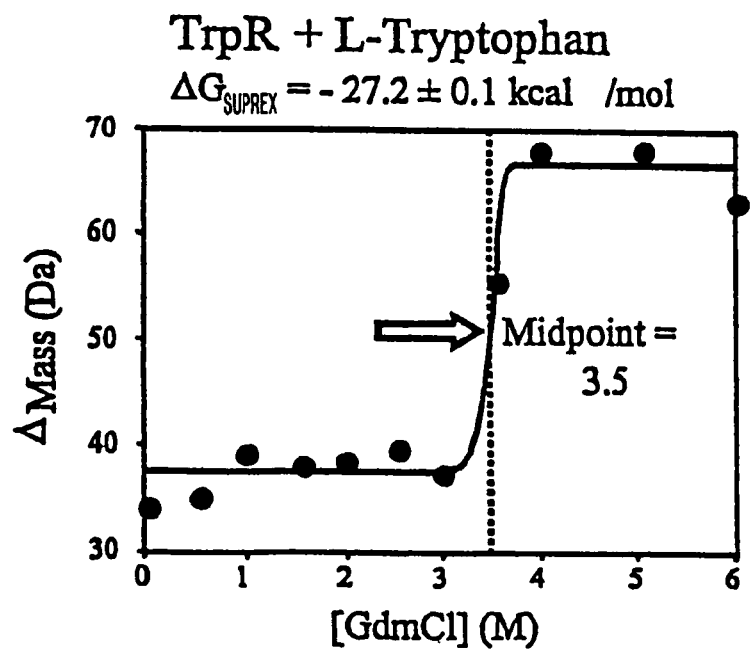
FIG. 18B is a line graph depicting the results from a SUPREX analysis of the Trp repressor protein in the presence of a tight binding ligand, L-tryptophan.

FIGS. 18A and 18B depict the results of a SUPREX analysis of the Trp repressor protein in the absence (FIG. 18A) and the presence (FIG. 18B) of a tight binding ligand, L-tryptophan. A fit of each data set to the SUPREX equation yielded folding free energies of −23.4±0.1 and −27.2±0.1 kcal/mol for the Trp repressor protein in the absence and presence of L-tryptophan, respectively. The concentration of Trp repressor in these experiments was 20 µM; and in (B) the concentration of L-tryptophan in each SUPREX buffer was 200 µM. At these concentrations of protein and ligand the data indicate that the $\Delta G_{Binding}$ for the Trp repressor and L-tryptophan system is −3.8 kcal/mol.

Laboratory Example 9

Figure 19:
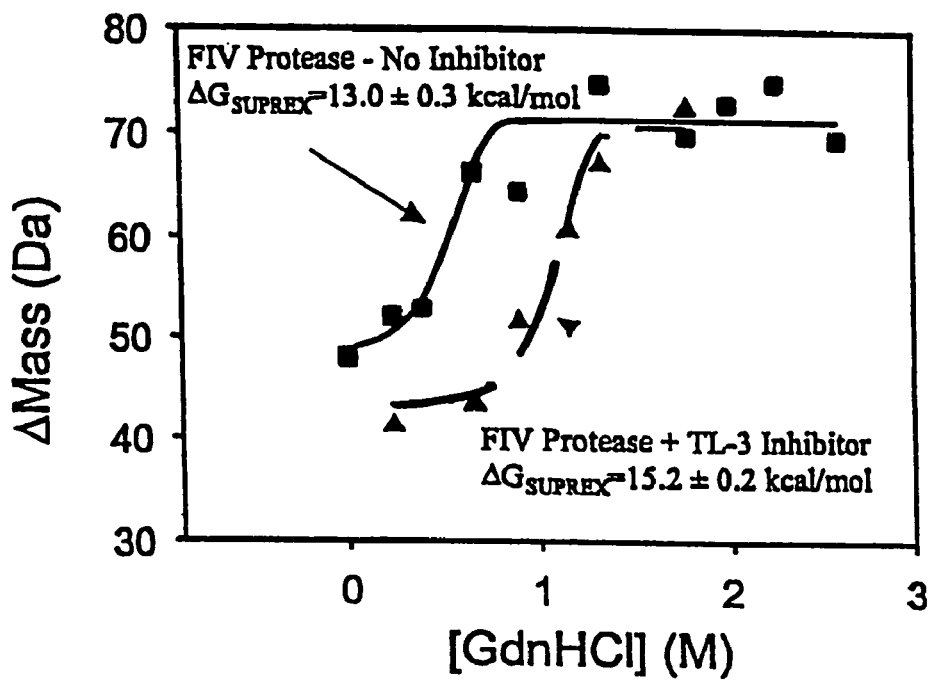
FIG. 19 is a line graph depicting the results of a SUPREX analysis of the feline immunodeficiency virus (FIV) protease in the absence and presence of the tight binding inhibitor, TL-3.

FIG. 19 depicts a SUPREX analysis of the feline immunodeficiency virus (FIV) protease in the absence (circles) and presence (triangles) of the tight binding inhibitor, TL-3. A fit of each data set to the SUPREX equation yielded-folding free energies of −13.0±0.3 and −15.2±0.2 kcal/mol for the FIV protease in the absence and presence of the TL-3 inhibitor, respectively. The concentration of the FIV protease in these experiments was 8 µM; and in (B) the concentration of the TL-3 inhibitor in each SUPREX buffer was 100 µM. At these concentrations of protein and ligand the data indicate that the $\Delta G_{Binding}$ for the this enzyme-inhibitor system is, −2.2 kcal/mol.

Laboratory Example 10

Figure 20:
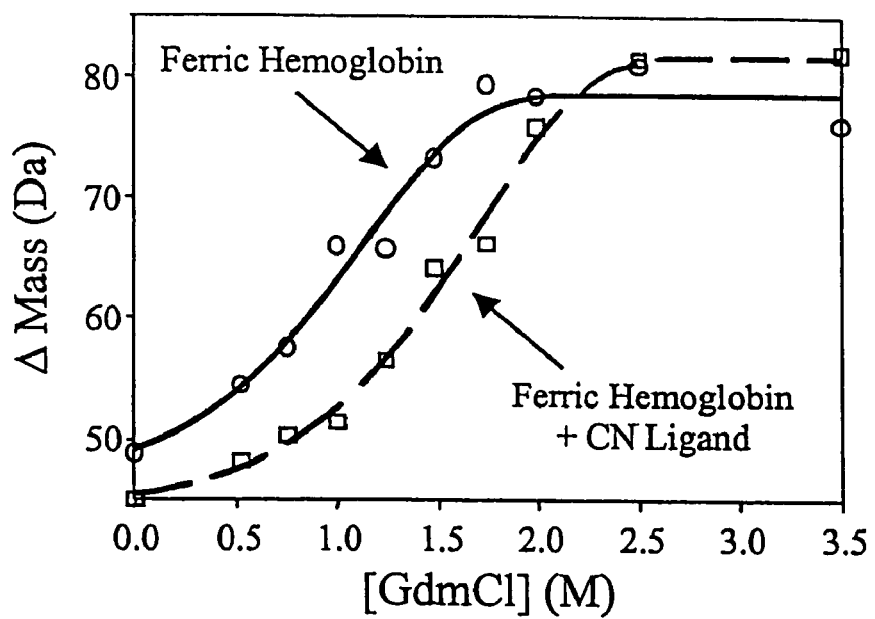
FIG. 20 is a line graph depicting the results of a SUPREX analysis of ferrous and ferric hemoglobin in the presence of cyanide ion, which selectively binds to ferric hemoglobin.

FIG. 20 depicts a SUPREX analysis of ferric hemoglobin (squares) and ferrous hemoglobin (circles) in the presence of cyanide ion. The lines represent the best fit of each data set to the SUPREX equation (i.e. Equation (6)). In this analysis of the data $k_{int}$ was set at 4.2 sec$^{-1}$, t=65 min$^{-1}$, and all other parameters in the SUPREX equation (i.e. $\Delta M_0$, $\Delta M_\infty$, and $\Delta G_f$, and m) were allowed to float. In this case an m-value of 1.1 kcal/mol was obtained. This m-value is significantly smaller than would be predicted for hemoglobin if it unfolded in a two-state process (i.e. 4.0 kcal mol$^{-1}$ M$^{-1}$). The relatively small m-value that was recorded for hemoglobin in the SUPREX experiment is consistent with a multi-state unfolding mechanism for this protein. Such multi-state unfolding behavior for hemoglobin's protein folding reaction has been previously noted. Thus, a meaningful folding free energy cannot be extracted from the SUPREX analysis of hemoglobin. However, it is noteworthy that a measurable shift (approximately 0.5 M) in the SUPREX transition midpoint to a higher [GdmCl] concentration is detected for the ferric hemoglobin SUPREX curve recorded in the presence of cyanide ion. This shift in the transition midpoint for ferric hemoglobin in the presence of cyanide is consistent with the tight binding interaction (affinity constant 100 nM$^{-1}$) of this ligand with hemoglobin.

REFERENCES

The references listed below as well as all references cited in the specification are incorporated herein by reference to the extent that they supplement, explain, provide a background for or teach methodology, techniques and/or compositions employed herein.

Bai & Englander, (1996) *Proteins* 24: 145-51
Bai et al., (1993) *Proteins* 17: 75-86
Bai et al., (1994) *Proteins* 20: 4-14
Bai et al., (1995) *Science* 269: 192-97
Beavis & Chait, (1996) *Method Enzymol.* 270: 519-51
Betton & Hofnung, (1996) *J. Biol. Chem.* 271: 8046-52
Blackstock & Weir, (1999) *Trends Biotechnol.* 17: 121-27
Brandts & Lin, (1990) *Biochem.* 29: 6927-40
Burton et al., (1996) *J. Mol. Biol.* 263: 311-22
Burton et al., (1997) *Nat. Struct. Biol.* 4: 305-10
Citri, (1973) *Adv. Enzymol. Relat. Areas Mol. Biol.* 37: 397-648
Clarke & Fersht, (1996) *Fold Des.* 1: 243-54
Clarke & Itzhaki, (1998) *Curr. Opin. Struct. Biol.* 8: 112-18
Deng & Smith, (1999) *Anal. Biochem.* 276: 150-60
Derrick & Wigley, (1992) *Nature* 359: 752-54
Derrick & Wigley, (1994) *J. Mol. Biol.* 243: 906-18
Dobson, (1999) *Trends Biochem. Sci.* 24: 329-32
Englander et al. (1996) *Curr. Opin. Struct. Biol.* 6: 18-23
Fahnestock et al., (1986) *J. Bacteriol.* 167: 870-80
Fields & Song, (1989) *Nature* 340: 245-46
Frand et al., (2000) *Trends Cell. Biol.* 10: 203-10
Frick et al., (1992) *Proc. Natl. Acad. Sci. U.S.A.* 89: 8532-36
Gallagher et al., (1994) *Biochem.* 33: 4721-29
Ghaemmaghami et al., (1998) *Biochem.* 37: 9179-85
Ghaemmaghami et al., (2000) *Proc. Natl. Acad. Sci. U.S.A.* 97: 8296-301
Glascoe & Long, (1959) *Anal. Chem.* 64: 188-93
Goldberg & Dice, (1974) *Annu. Rev. Biochem.* 43: 835-69
Graziano et al., (1996) *Biochem.* 35: 13386-92
Huang & Oas, (1995) *Biochem.* 34: 3884-92
Huang & Oas, (1995) *Proc. Natl. Acad. Sci. U.S.A.* 92: 6878-82
Huyghues-Despointes et al., (1999) *Nat. Struct. Biol.* 6: 910-12
Hvidt & Nielson, (1966) *Adv. Prot. Chem.* 21: 287-386
Inouye et al., (1985) *Nucleic Acids Res.* 13: 3101-09
Jaenicke, (1987) *Prog. Biophys. Mol. Biol.* 49: 117-237
Kamtekar et al., (1993) *Science* 262: 1680-85.
Kanaya et al., (1996) *J. Biol. Chem.* 271: 32729-36
Kwon et al. (1996) *Protein Eng.* 9(12): 1197-202
Li & Woodward, (1999) *Protein Sci.* 8: 1571-90
Loh et al., (1996) *Proc. Natl. Acad. Sci. U.S.A.* 93: 1982-87
Martineau et al., (1990) *J. Mol. Biol.* 214: 337-52
Mayo & Baldwin, (1993) *Science* 262: 873-76
McLendon & Radany, (1978) *J. Biol. Chem.* 253: 6335-37
Miller & Dill, (1995) *Protein Sci.* 4: 1860-73
Miranker et al., (1996) *FASEB J.* 10: 93-101
Moore et al., (19997) *J. Mol. Biol.* 272: 336-47
Myers et al., (1995) *Protein Sci.* 4: 2138-48
Neurath et al., (1944) *Chem. Rev.* 34: 157-265
Nozaki, (1972) *Methods Enzymol.*, 26: 43-50
Orban et al., (1994) *Biochem.* 33: 5702-10
Pace & Grimsley, (1988) *Biochem.* 27: 3242-46
Pace & McGrath, (1980) *J. Biol. Chem.* 255: 3862-65
Pace et al., (1986) 131: 266-280
Pace et al., (1990) *Biochem.* 29: 2564-72
Pace, (1986) *Method Enzymol.* 131: 266-80.
Padan et al., (1976) *Eur. J. Biochem.* 63: 533-41
Parsell & Sauer, (1989) *J. Biol. Chem.* 264: 7590-95.
Raschke & Marqusee, (1997) *Nat. Struct. Biol.* 4: 298-304
Record et al., (1998) *Trends Biochem. Sci.* 23: 190-94
Record et al., (1998) *Trends Biochem. Sci.* 23: 143-48
Reidhaar-Olson et al., (1990) *Biochem.* 29: 7563-71
Rosenbaum et al., (1999) *J. Am. Chem. Soc.* 121: 9509-13
Ruther et al., (1983) *EMBO J* 2: 1791

Sambrook et al., (1992) *Molecular Cloning: A Laboratory Manual*, Cold Spring Harbor, N.Y.
Sandberg et al., (1995) *Biochem.* 34: 11970-78
Sauer-Eriksson et al., (1995) *Structure* 3: 265-78
Schellman, (1975) *Biopolymers* 14: 999-1018
Schellman, (1987) *Annu. Rev. Biophys. Bio.* 16: 115-37
Schuerendberg et al., (2000) *Anal. Chem.* 72: 3436-442
Schwartz, (1988) *Biochem.* 27: 8429-36
Segel, (1975) *Enzyme Kinetics*, John Wiley & Sons, New York, N.Y.
Sela & Anfinsen, (1957) *Biochim. Biophys. Acta* 24: 229-235
Sheshadri et al., (1999) *Protein Sci.* 8: 1689-95
Shoichet et al., (1995) *Proc. Natl. Acad. Sci. U.S.A.* 92: 452-56
Sloan & Hellinga, (1998) *Protein Eng.* 11: 819-23
Sloan & Hellinga, (1999) *Protein Sci.* 8: 1643-48
Straume & Freire, (1992) *Anal. Biochem.* 203: 259-68
Van den Burg et al., (1998) *Proc. Natl. Acad. Sci. U.S.A.* 95(5): 2056-60
Van Heeke et al., (1989) *J. Biol. Chem.* 264: 5503-9
Varley & Pain, (1991) *J. Mol. Biol.* 220: 531-38
Walker et al., (1995) *Biochem. J.* 310: 177-84
Warren et al., (1964) *Biochem. J.* 93: 409-19
Wright & Dyson, (1999) *J. Mol. Biol.* 293: 321-31
Xie et al., (2000) *J. Am. Chem. Soc.* 122: 11533-34
Yancey et al., (1982) *Science* 217: 1214-22
Yi et al., (1997) *Fold. Des.* 2: 271-80
Zhang, Ph.D. Thesis, Structural Biology and Molecular Biophysics, University of Pennsylvania
U.S. Pat. No. 5,679,582.

TABLE 1

STABILITY OF PROTEINS BY SUPREX AND CIRCULAR DICHROISM DENATURATION.

| Protein (with note amino acid mutations) | $\Delta G_f$(kcal/mol) SUPREX[a] | $\Delta G_f$(kcal/mol) CD | $\Delta\Delta G_f$(kcal/mol) SUPREX[a] | $\Delta\Delta G_f$(kcal/mol) CD |
|---|---|---|---|---|
| $\lambda_{6\text{-}85}$ | $-5.0 \pm 0.4$ | $-4.4 \pm 0.2$[b] | — | — |
| $\lambda_{6\text{-}85}$ (A66G) | $>-4.0$ | | $>1.0$ | $1.5$[c] |
| $\lambda_{6\text{-}85}$ (A63G) | $-4.8 \pm 0.4$ | | $0.2$ | $0.4$[c] |
| $\lambda_{6\text{-}85}$ (G46A/G48A/A66G) | $-5.2 \pm 0.4$ | | $-0.2$ | $-0.4$[c] |
| $\lambda_{6\text{-}85}$ (G46A/G48A/A49G) | $-5.6 \pm 0.4$ | | $-0.6$ | $-1.0$[c] |
| $\lambda_{6\text{-}85}$ (Q33Y) | $-6.5 \pm 0.4$ | | $-1.5$ | $-1.5$[d] |
| $\lambda_{6\text{-}85}$ (G46A/G48A) | $-6.7 \pm 0.4$ | $-6.1 \pm 0.2$[b] | $-1.7$ | $-1.7$ |
| $\lambda_{6\text{-}85}$ (G46A/G48A/Q33Y) | $-7.9 \pm 0.7$ | | $-2.9$ | $-3.4$[d] |
| MBP | $-16 \pm 3$ | $-14.5 \pm 0.4$[e], $-12.5 \pm 0.2$[f] | | |
| MBP + 100 μM maltose | $-19 \pm 3$ | — | $-3.0$ | $-2.9$[g] |

[a]Stabilities measured at 23° C.
[b]Stabilities measured at 25° C.
[c]$\Delta\Delta G_f$ ($\Delta G_f^{variant} - \Delta G_f^{wild\,type}$) were measured at 37° C. (Burton et al., (1997) Nat. Struct. Biol. 4: 305-10).
[d]$\Delta\Delta G_f$ measured at 25° C.
[e]Stability measured at 25° C. by urea titration (Sheshadri et al., (1999) Protein Sci. 8: 1689-95).
[f]Stability measured at 25° C. by GdmCl titration (Sheshadri et al., (1999) Protein Sci. 8: 1689-95).
[g]A dissociation constant of 1 μM (Martineau et al., (1990) J. Mol. Biol. 214: 337-52) and an estimated protein concentration of 5 μM were used to calculate the expected change in stability (Schellman, (1975) Biopolymers 14: 999-1018).

TABLE 2

DISSOCIATION CONSTANTS OF B1 DOMAIN FOR FC FRAGMENT BASED ON BINDING-INDUCED STABILITY CHANGES AS DETECTED BY MALDI MS-HX AT 22° C., PH 6

| Protein[a] | Exchange Time (min) | Protonated Mass (Da) | Deuterated Mass (Da)[b] | $\Delta G_{unfold}°$ (kcal/mol) | $\Delta\Delta G_{unfold}°$ (kcal/mol) | Kd (μM) |
|---|---|---|---|---|---|---|
| WT* | 10 | 6040 | 6073 | $5.1 \pm 0.1$ | | |
| WT* + Fc | 10 | 6040 | 6077 | $6.3 \pm 0.1$ | 1.2 | 0.1 |
| WT* | 90 | 6040 | 6071 | $5.6 \pm 0.1$ | | |
| WT* + Fc | 90 | 6040 | 6072 | $6.4 \pm 0.1$ | 0.8 | 1.1 |
| WT* | 180 | 6040 | 6068 | $5.8 \pm 0.1$ | | |
| WT* + Fc | 180 | 6040 | 6069 | $6.7 \pm 0.1$ | 0.9 | 0.6 |
| E27A | 90 | 5982 | 6014 | $5.7 \pm 0.2$ | | |
| E27A + Fc | 90 | 5982 | 6017 | $5.8 \pm 0.1$ | 0.1 | >100 |

[a]The concentration of B1 domain variants were 25 μM, + Fc represents the addition of 24 μM Fc fragment
[b]The effective fully deuterated mass taking into account MALDI MS-HX back-exchange measured after exchange in the presence of 3 M GdmCl

TABLE 3

FRACTION EXCHANGED AFTER 20' AT 23° C.

| Protein | Sample | pH[1] | Additive | Protonated mass | Deuterated mass[4] | Mass after 20'exchange | Fraction exchanged |
|---|---|---|---|---|---|---|---|
| $\lambda^*_{6\text{-}85}$ | intact cells | 7 | | 8752 | 8807 | $8794 \pm 1.5$ | $0.76 \pm 0.03$ |
| $\lambda^*_{6\text{-}85}$ | intact cells | 8 | | 8752 | 8807 | $8795 \pm 1.9$ | $0.78 \pm 0.03$ |
| $\lambda^*_{6\text{-}85}$ | cell lysate | 7 | | 8752 | 8802 | $8776 \pm 3.3$ | $0.44 \pm 0.06$ |
| $\lambda^*_{6\text{-}85}$ | cell lysate | 8 | | 8752 | 8802 | $8792 \pm 2.8$ | $0.73 \pm 0.05$ |

TABLE 3-continued

FRACTION EXCHANGED AFTER 20' AT 23° C.

| Protein | Sample | pH[1] | Additive | Protonated mass | Deuterated mass[4] | Mass after 20'exchange | Fraction exchanged |
|---|---|---|---|---|---|---|---|
| $\lambda^*_{6-85}$ | cell lysate | 7 | urea[2] | 8752 | 8807 | 8803 ± 1.7 | 0.93 ± 0.03 |
| $\lambda^*_{6-85}$ | intact cells | 7 | NaCl[3] | 8752 | 8807 | 8785 ± 1.5 | 0.59 ± 0.03 |
| $\lambda^*_{6-85}$ (Q33Y) | intact cells | 7 | | 8787 | 8842 | 8818 ± 1.5 | 0.55 ± 0.03 |

[1]For intact cells, pH is given for external medium.
[2]3M urea added only during exchange interval.
[3]1.2 M NaCl in medium during protein expression.
[4]Effective fully exchanged mass, not equivalent to the mass when all exchangeable hydrogens are deuterated because the most labile deuterons re-exchange with protons during preparation of MALDI samples.

What is claimed is:

1. A method of detecting a disease characterized by protein misfolding, the method comprising:
   (a) providing a test protein suspected of being misfolded;
   (b) contacting the protein with an exchange buffer comprising a denaturant and deuterium, the exchange buffer having a denaturant concentration;
   (c) contacting the test protein with a mass spectrometry matrix medium;
   (d) determining a change in mass of the test protein resulting from hydrogen-deuterium exchange by mass spectrometry;
   (e) varying the denaturant concentration of the exchange buffer;
   (f) repeating steps (a)-(e) a desired number of times to generate a denaturation curve of the tested protein; and
   (g) analyzing the change in mass of the test protein as a function of the denaturant concentration to determine a stability of the test protein; and
   (h) comparing the stability of the test protein suspected of being misfolded with a known stability of a properly folded test protein, wherein a change in stability of the test protein when compared with the known stability of the properly folded test protein is indicative of a disease characterized by protein misfolding.

2. The method of claim 1, wherein the test protein is disposed in a crude cell lysate.

3. The method of claim 1, wherein the test protein has a mass of less than 1,000,000 daltons.

4. The method of claim 1, wherein the test protein is a multimeric protein.

5. The method of claim 1, wherein the test protein is disposed on a microtiter plate.

6. The method of claim 5, wherein a plurality of test proteins are disposed on the microtiter plate.

7. The method of claim 6, wherein the method further comprises the step of repeating steps (a)-(h) for each test protein disposed on the microtiter plate.

8. The method of claim 1, wherein the test protein is provided in picomolar or greater amounts.

9. The method of claim 1, wherein the test protein is in vivo.

10. The method of claim 1, wherein the denaturant is a chemical denaturant.

11. The method of claim 10, wherein the denaturant is selected from the group consisting of detergents, guanidinium chloride and urea.

12. The method of claim 1, wherein the mass spectrometry matrix material is a MALDI mass spectrometry matrix material and the mass spectrometry is MALDI mass spectrometry.

13. The method of claim 12, wherein the MALDI mass spectrometry matrix material is selected from the group consisting of sinapinic acid, α-cyano-4-hydroxycinnamic acid, 2,5-dihydroxybenzoic acid, 2,5-dihydroxyacetophenone and 3-amino-4-hydroxybenzoic acid.

14. The method of claim 1, wherein the analyzing comprises fitting data comprising a change in mass of the mutant test protein as a function of denaturant to the equation $\Delta Mass = \Delta M\infty + (\Delta M_0 - \Delta M_4)e^{-(<kin>/(1+Kfold))t}$, wherein $K^{fold} = e^{-(\Delta Gf + m[Denat.])/RT)}$ and $\Delta G_f$ is the stability of the mutant test protein.

15. The method of claim 1, wherein the analyzing is performed using a computer program.

16. The method of claim 1, wherein the step of analyzing the change in mass of the test protein to determine a stability of the mutant test protein comprises determining a free energy of folding from a denaturation curve based on the change of mass of the protein, the free energy of folding being indicative of the stability of a test protein.

17. The method of claim 1, wherein the step of analyzing the change in mass of the test protein to determine a stability of the mutant test protein comprises determining a change in mass of the test protein based on the exchange of deuterium for hydrogen, the exchange being dependent on slow-exchanging hydrogens in the test protein.

18. The method of claim 1, further comprising providing a reference protein with the test protein.

19. The method of claim 1, further comprising:
   (a) contacting the test protein with a reverse phase chromatography matrix; and
   (b) eluting the test protein from the chromatography matrix.

20. The method of claim 19, further comprising contacting the test protein with an acid before contacting the test protein with the reverse phase chromatography matrix.

* * * * *